(12) United States Patent
Moutafis et al.

(10) Patent No.: US 7,717,685 B2
(45) Date of Patent: May 18, 2010

(54) HIGH PRESSURE PUMPING CARTRIDGES FOR MEDICAL AND SURGICAL PUMPING AND INFUSION APPLICATIONS

(75) Inventors: Timothy E. Moutafis, Gloucester, MA (US); David M. Fischer, Waltham, MA (US)

(73) Assignee: HydroCision, Inc., North Billerica, MA (US)

( * ) Notice: Subject to any disclaimer, the term of this patent is extended or adjusted under 35 U.S.C. 154(b) by 1215 days.

(21) Appl. No.: 10/754,905

(22) Filed: Jan. 9, 2004

(65) Prior Publication Data
US 2004/0234380 A1    Nov. 25, 2004

Related U.S. Application Data

(63) Continuation of application No. 10/134,970, filed on Apr. 29, 2002, now abandoned.

(60) Provisional application No. 60/287,219, filed on Apr. 27, 2001.

(51) Int. Cl.
*F04B 53/12* (2006.01)
*F16J 9/00* (2006.01)
*F16J 9/02* (2006.01)

(52) U.S. Cl. .................. 417/547; 417/555.1; 92/240; 277/439

(58) Field of Classification Search ............... 417/547, 417/555.1; 92/240, 241; 277/436–444
See application file for complete search history.

(56) References Cited

U.S. PATENT DOCUMENTS

| | | |
|---|---|---|
| 1,773,629 A | 8/1930 | Millmine |
| 2,648,288 A | 8/1953 | Marks |
| RE24,329 E | 6/1957 | Booth |
| 2,808,302 A | 10/1957 | Bowerman |

(Continued)

FOREIGN PATENT DOCUMENTS

DE    3320076 A1    12/1984

(Continued)

OTHER PUBLICATIONS

Baer et al., "Jet-cutting—an alternative to the ultrasonic aspirator?" Chirurg, 61:735, 1990 and Reply to commentary.

(Continued)

*Primary Examiner*—Charles G Freay
(74) *Attorney, Agent, or Firm*—McCarter & English, LLP; David R. Burns

(57) ABSTRACT

Pumping cartridges useful for medical and surgical pumping and infusion procedures. In one aspect, a series of pumping cartridges include cylinders and pistons which have a sealing component including a circumferential, flared sealing flange and can be configured to enable the pumping cartridge to generate high liquid pumping pressures. Many of the pumping cartridges can be configured to be detachable from a pump drive unit and disposable after a single use. Some pistons include or at least partially form a valve and/or are relatively movable with respect to a connected piston rod. Valves include a valve seat and a movable sealing element able to create a seal capable of withstanding differences in fluid pressures thereacross of at least about 1,000 psi. The movable sealing element is concave in shape, and may be curved for improved sealing performance. Methods for pumping or infusing a liquid for delivery to the body of a patient or a surgical or medical instrument.

23 Claims, 21 Drawing Sheets

U.S. PATENT DOCUMENTS

| | | |
|---|---|---|
| 2,885,227 A | 5/1959 | Burger |
| 3,310,283 A | 3/1967 | Carlton |
| 3,456,915 A | 7/1969 | Smolen |
| 3,496,874 A | 2/1970 | Findlay |
| 3,583,710 A | 6/1971 | Burelle |
| 3,590,813 A | 7/1971 | Roszyk |
| 3,620,653 A | 11/1971 | Gaylord et al. |
| 3,771,907 A | 11/1973 | Neumann et al. |
| 3,818,913 A | 6/1974 | Wallach |
| 3,874,826 A | 4/1975 | Lundquist et al. |
| 3,930,505 A | 1/1976 | Wallach |
| 3,994,208 A | 11/1976 | Boyer |
| 4,009,645 A | 3/1977 | Freimuth |
| 4,111,490 A | 9/1978 | Liesveld |
| 4,116,452 A | 9/1978 | Schanz |
| 4,116,952 A | 9/1978 | Beffa et al. |
| 4,137,804 A | 2/1979 | Gerber et al. |
| 4,142,524 A | 3/1979 | Jassawalla et al. |
| 4,155,559 A | 5/1979 | Sieghartner |
| 4,165,084 A | 8/1979 | Kempf |
| 4,196,909 A * | 4/1980 | Porsch et al. ............... 277/452 |
| 4,199,307 A | 4/1980 | Jassawalla |
| 4,214,507 A | 7/1980 | Hock et al. |
| 4,216,906 A | 8/1980 | Olsen et al. |
| 4,267,862 A | 5/1981 | Neff et al. |
| 4,270,440 A | 6/1981 | Lewis, II |
| 4,270,990 A | 6/1981 | Fong |
| 4,281,590 A | 8/1981 | Weaver |
| 4,304,531 A | 12/1981 | Fisher |
| 4,336,800 A | 6/1982 | Pastrone |
| 4,336,946 A | 6/1982 | Wheeler |
| 4,410,322 A | 10/1983 | Archibald |
| 4,435,902 A | 3/1984 | Mercer et al. |
| 4,465,438 A | 8/1984 | Brauer et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,517,977 A | 5/1985 | Frost |
| 4,521,027 A | 6/1985 | Marshall |
| 4,557,725 A | 12/1985 | Heyne et al. |
| 4,560,373 A | 12/1985 | Sugino et al. |
| 4,573,883 A | 3/1986 | Noon et al. |
| 4,601,235 A | 7/1986 | Roberts |
| 4,614,481 A | 9/1986 | Vanderjagt |
| 4,635,621 A | 1/1987 | Atkinson |
| 4,637,551 A | 1/1987 | Seeger, Jr. et al. |
| 4,657,490 A | 4/1987 | Abbott |
| 4,662,829 A | 5/1987 | Nehring |
| 4,690,672 A | 9/1987 | Veltrup |
| 4,730,550 A | 3/1988 | Bramstedt et al. |
| 4,735,129 A | 4/1988 | Sjoberg |
| 4,741,678 A | 5/1988 | Nehring |
| 4,743,033 A | 5/1988 | Guess |
| 4,749,337 A | 6/1988 | Dickinson et al. |
| 4,754,929 A | 7/1988 | Struve et al. |
| 4,761,039 A | 8/1988 | Hilaris |
| 4,776,616 A | 10/1988 | Umehara et al. |
| 4,776,769 A | 10/1988 | Hilaris |
| 4,795,217 A | 1/1989 | Hilaris |
| 4,798,339 A | 1/1989 | Sugino et al. |
| 4,798,589 A | 1/1989 | Tseo |
| 4,811,902 A | 3/1989 | Nagata |
| 4,813,343 A | 3/1989 | Schaefer |
| 4,818,190 A | 4/1989 | Pelmulder et al. |
| 4,827,679 A | 5/1989 | Earle, III |
| 4,842,584 A | 6/1989 | Pastrone |
| 4,857,048 A | 8/1989 | Simons et al. |
| 4,872,813 A | 10/1989 | Gorton et al. |
| 4,896,085 A | 1/1990 | Jones |
| 4,898,574 A | 2/1990 | Uchiyama et al. |
| 4,898,579 A | 2/1990 | Groshong et al. |
| 4,913,698 A | 4/1990 | Ito et al. |
| 4,921,409 A | 5/1990 | Besic |
| 4,927,411 A | 5/1990 | Pastrone et al. |
| 4,932,114 A | 6/1990 | Morse et al. |
| 4,937,985 A | 7/1990 | Boers et al. |
| 4,940,399 A | 7/1990 | Gorton et al. |
| 4,950,238 A | 8/1990 | Sullivan |
| 4,958,963 A | 9/1990 | Perrault |
| 5,002,316 A | 3/1991 | Chohan |
| 5,006,043 A | 4/1991 | Katsumata et al. |
| 5,006,050 A | 4/1991 | Cooke et al. |
| 5,011,468 A | 4/1991 | Lundquist et al. |
| 5,018,670 A | 5/1991 | Chalmers |
| 5,027,792 A | 7/1991 | Meyer |
| 5,037,431 A | 8/1991 | Summers et al. |
| 5,052,624 A | 10/1991 | Boers et al. |
| 5,056,992 A | 10/1991 | Simons et al. |
| 5,074,862 A | 12/1991 | Rausis |
| 5,087,056 A | 2/1992 | Baglin |
| 5,092,744 A | 3/1992 | Boers |
| 5,098,262 A | 3/1992 | Wecker et al. |
| 5,111,652 A | 5/1992 | Andre |
| 5,125,582 A | 6/1992 | Surjaatmadja et al. |
| 5,133,687 A | 7/1992 | Malloy |
| 5,135,482 A | 8/1992 | Neracher |
| 5,154,589 A | 10/1992 | Ruhl et al. |
| 5,162,016 A | 11/1992 | Malloy |
| 5,163,692 A * | 11/1992 | Schofield et al. ............ 277/436 |
| 5,171,045 A | 12/1992 | Pasbrig |
| 5,186,615 A | 2/1993 | Karliner |
| 5,195,754 A | 3/1993 | Dietle |
| 5,197,955 A | 3/1993 | Stephens et al. |
| 5,201,643 A | 4/1993 | Hirosawa et al. |
| 5,205,779 A | 4/1993 | O'Brien et al. |
| 5,211,633 A | 5/1993 | Stouder, Jr. |
| 5,217,465 A | 6/1993 | Steppe |
| 5,230,443 A | 7/1993 | Du |
| 5,237,309 A | 8/1993 | Frantz et al. |
| 5,250,065 A | 10/1993 | Clement et al. |
| 5,252,044 A | 10/1993 | Raines et al. |
| 5,259,842 A | 11/1993 | Plechinger et al. |
| 5,261,883 A | 11/1993 | Hood et al. |
| 5,281,108 A | 1/1994 | Brooke |
| 5,284,084 A * | 2/1994 | Pippert et al. ................. 92/241 |
| 5,290,245 A | 3/1994 | Dennis |
| 5,314,375 A | 5/1994 | O'Brien et al. |
| 5,322,504 A | 6/1994 | Doherty et al. |
| 5,339,715 A | 8/1994 | Coleman et al. |
| 5,344,292 A | 9/1994 | Rabenau et al. |
| 5,364,234 A | 11/1994 | Eickmann |
| 5,368,452 A | 11/1994 | Johnson et al. |
| 5,370,609 A | 12/1994 | Drasler et al. |
| 5,378,126 A | 1/1995 | Abrahamson et al. |
| 5,392,694 A * | 2/1995 | Muller et al. ................. 99/295 |
| 5,415,528 A | 5/1995 | Ogden et al. |
| 5,429,485 A | 7/1995 | Dodge |
| 5,449,369 A | 9/1995 | Imran |
| 5,464,392 A | 11/1995 | Epstein et al. |
| 5,476,368 A | 12/1995 | Rabenau et al. |
| 5,480,163 A | 1/1996 | Miser et al. |
| 5,482,297 A | 1/1996 | Burns et al. |
| 5,490,680 A | 2/1996 | Patel et al. |
| 5,496,267 A | 3/1996 | Drasler et al. |
| 5,505,729 A | 4/1996 | Rau |
| 5,509,911 A | 4/1996 | Cottone, Sr. et al. |
| 5,511,464 A | 4/1996 | Cezanne et al. |
| 5,533,879 A | 7/1996 | Chen |
| 5,540,568 A | 7/1996 | Rosen et al. |
| 5,542,918 A | 8/1996 | Atkinson |
| 5,554,013 A | 9/1996 | Owens et al. |
| 5,558,646 A | 9/1996 | Roche |
| 5,562,186 A | 10/1996 | Osenbaugh |
| 5,562,692 A | 10/1996 | Bair |

| | | | |
|---|---|---|---|
| 5,586,868 A | 12/1996 | Lawless et al. | |
| 5,591,184 A | 1/1997 | McDonnell et al. | |
| 5,607,391 A | 3/1997 | Klinger et al. | |
| 5,620,414 A | 4/1997 | Campbell, Jr. | |
| 5,626,072 A | 5/1997 | Mirand et al. | |
| 5,632,606 A * | 5/1997 | Jacobsen et al. | 417/415 |
| 5,647,852 A | 7/1997 | Atkinson | |
| 5,667,102 A | 9/1997 | Keller | |
| 5,674,226 A | 10/1997 | Doherty et al. | |
| 5,711,151 A | 1/1998 | Engfer | |
| 5,713,878 A | 2/1998 | Moutafis et al. | |
| 5,735,815 A | 4/1998 | Bair | |
| 5,749,885 A | 5/1998 | Sjostrom et al. | |
| 5,842,701 A | 12/1998 | Cawthorne et al. | |
| 5,845,749 A * | 12/1998 | Moretz et al. | 188/281 |
| 5,849,023 A | 12/1998 | Mericle | |
| 5,865,442 A | 2/1999 | Iwashita | |
| 5,865,992 A | 2/1999 | Edmondson | |
| 5,871,462 A | 2/1999 | Yoder et al. | |
| 5,899,915 A | 5/1999 | Saadat | |
| 5,941,162 A | 8/1999 | Kiesel | |
| 5,944,686 A | 8/1999 | Patterson et al. | |
| 5,960,700 A | 10/1999 | Staggs et al. | |
| 6,017,354 A | 1/2000 | Culp et al. | |
| 6,027,502 A | 2/2000 | Desai | |
| 6,045,564 A | 4/2000 | Walen | |
| 6,066,150 A | 5/2000 | Gonon | |
| 6,083,189 A | 7/2000 | Gonon et al. | |
| 6,085,631 A | 7/2000 | Kownacki | |
| 6,096,001 A | 8/2000 | Drasler | |
| 6,142,484 A | 11/2000 | Valls, Jr. et al. | |
| 6,161,834 A | 12/2000 | Pollack et al. | |
| 6,216,573 B1 | 4/2001 | Moutafis et al. | |
| 6,280,302 B1 | 8/2001 | Hashish et al. | |
| 6,322,533 B1 | 11/2001 | Gonon | |
| 6,375,635 B1 | 4/2002 | Moutafis et al. | |
| 6,402,715 B2 | 6/2002 | Manhes | |
| 6,419,654 B1 | 7/2002 | Kadan | |
| 6,423,028 B1 | 7/2002 | Gonon | |
| 6,451,017 B1 | 9/2002 | Moutafis et al. | |
| 6,464,567 B2 | 10/2002 | Hashish et al. | |
| 6,491,660 B2 | 12/2002 | Guo et al. | |
| 6,508,823 B1 | 1/2003 | Gonon | |
| 6,511,493 B1 | 1/2003 | Moutafis et al. | |
| 6,544,220 B2 | 4/2003 | Shuman et al. | |
| 6,669,710 B2 | 12/2003 | Moutafis et al. | |
| 6,899,712 B2 | 5/2005 | Moutafis et al. | |
| 6,923,792 B2 | 8/2005 | Staid et al. | |
| 6,960,182 B2 | 11/2005 | Moutafis et al. | |
| 2001/0002562 A1 | 6/2001 | Moutafis et al. | |
| 2002/0050197 A1 | 5/2002 | Moutafis et al. | |
| 2002/0176788 A1 | 11/2002 | Moutafis et al. | |
| 2002/0177802 A1 | 11/2002 | Moutafis et al. | |
| 2003/0009166 A1 | 1/2003 | Moutafis et al. | |
| 2003/0040763 A1 | 2/2003 | Moutafis et al. | |
| 2003/0055404 A1 | 3/2003 | Moutafis | |
| 2003/0083681 A1 | 5/2003 | Moutafis et al. | |
| 2003/0125660 A1 | 7/2003 | Moutafis et al. | |
| 2004/0228736 A1 | 11/2004 | Moutafis et al. | |
| 2004/0230211 A1 | 11/2004 | Moutafis et al. | |
| 2004/0234380 A1 | 11/2004 | Moutafis et al. | |
| 2004/0243157 A1 | 12/2004 | Connor et al. | |

FOREIGN PATENT DOCUMENTS

| | | |
|---|---|---|
| DE | 225 618 A1 | 8/1985 |
| DE | 3421 390 A1 | 12/1985 |
| DE | 4201992 A1 | 11/1993 |
| DE | 19734890 C1 | 7/1999 |
| EP | 0 411 170 A1 | 2/1991 |
| EP | 0 420 781 A2 | 4/1991 |
| EP | 0 485 133 A1 | 5/1992 |
| EP | 0 489 496 A1 | 6/1992 |
| EP | 0 551 920 A1 | 7/1993 |
| EP | 0 555 549 A1 | 8/1993 |
| EP | 0 636 345 A1 | 2/1995 |
| EP | 0 855 507 A2 | 7/1998 |
| FR | 1 241 277 A | 9/1960 |
| FR | 2 094 507 A | 2/1972 |
| GB | 199057 A | 6/1923 |
| GB | 651836 A | 4/1951 |
| WO | WO 94/14584 A1 | 7/1994 |
| WO | WO 96/40476 A1 | 12/1996 |
| WO | WO 99/33510 A1 | 7/1999 |
| WO | WO 02/095234 A1 | 11/2002 |
| WO | WO 03/013645 A1 | 2/2003 |
| WO | WO 03/024340 A2 | 3/2003 |

OTHER PUBLICATIONS

Baer et al., "New water-jet dissector: initial experience in hepatic surgery," Br. J. Surg., vol. 78, pp. 502-503, Apr. 1991.

Baer et al., "Water-jet dissection in hepatic surgery," Minimally Invasive Therapy, vol. 1, pp. 169-172, 1992.

Baer et al., "Hepatic Surgery Facilitated by a New Jet Dissector," HPB Surgery, vol. 4, pp. 137-146, 1991.

Drasler et al., "A rheolytic system for percutaneous coronary and peripheral plaque removal," Angiology—The Journal of Vascular Diseases, Feb. 1991, vol. 42, No. 2, pp. 90-98.

Drasler et al., "Rheolytic catheter for percutaneous removal of thrombus," Radiology, Jan. 1992, vol. 182, pp. 263-267.

Field, J.E, "The physics of liquid impact, shock wave interactions with cavities, and the implications to shock wave lithotripsy," Phys. Med. Biol., vol. 36, No. 11, pp. 1475-1484, 1991.

Giraud et al., "Bone cutting," Clin. Phys. Physiol. Meas., vol. 12, No. 1, pp. 1-19, 1991.

Izumi et al., "Hepatic resection using a water jet dissector," Surgery Today Jpn. J. Surg., vol. 23, pp. 31-35, 1993.

Papachristou et al., "Resection of the liver with a water jet", Br. J. Surg., 1982, vol. 69, pp. 93-94.

Terzis et al., "A new system for cutting brain tissue preserving vessels: water jet cutting," British Journal of Neurosurgery, vol. 3, pp. 361-366, 1989.

Water Jet Dissector, Hepatotom® Supersonic Microjet Dissector brochure, Medical Exports AG.

Official Communication from corresponding Canadian Patent Application No. 2,484,061, dated Aug. 19, 2005.

Official Communication from corresponding Canadian Patent Application No. 2,484,061, dated Apr. 10, 2006.

Official Communication from corresponding European Patent Application No. 02729070.9, dated Sep. 16, 2004.

Official Communication from corresponding European Patent Application No. 02729070.9, dated Feb. 14, 2006 and Claims as Pending.

Tikhomirov, R.A., et al "High-Pressure Jet Cutting TJ840 G5313" 1992.

International Search Report Oct. 8, 2001 of U.S. PCT 2001/00785.

International Search Report Nov. 4, 2002 of U.S. PCT 2002/13608.

International Search Report Dec. 10, 2002 of U.S. PCT 2002/25133.

Communication pursuant to Article 96(2) EPC, dated Aug. 29, 2005 for corresponding European patent application serial No. 02768451.3-2310.

Communication for corresponding Canadian patent application serial No. 2,493,238, dated Jun. 15, 2005.

Communication for corresponding Australian patent application serial No. 2002331012, dated Feb. 14, 2005.

* cited by examiner

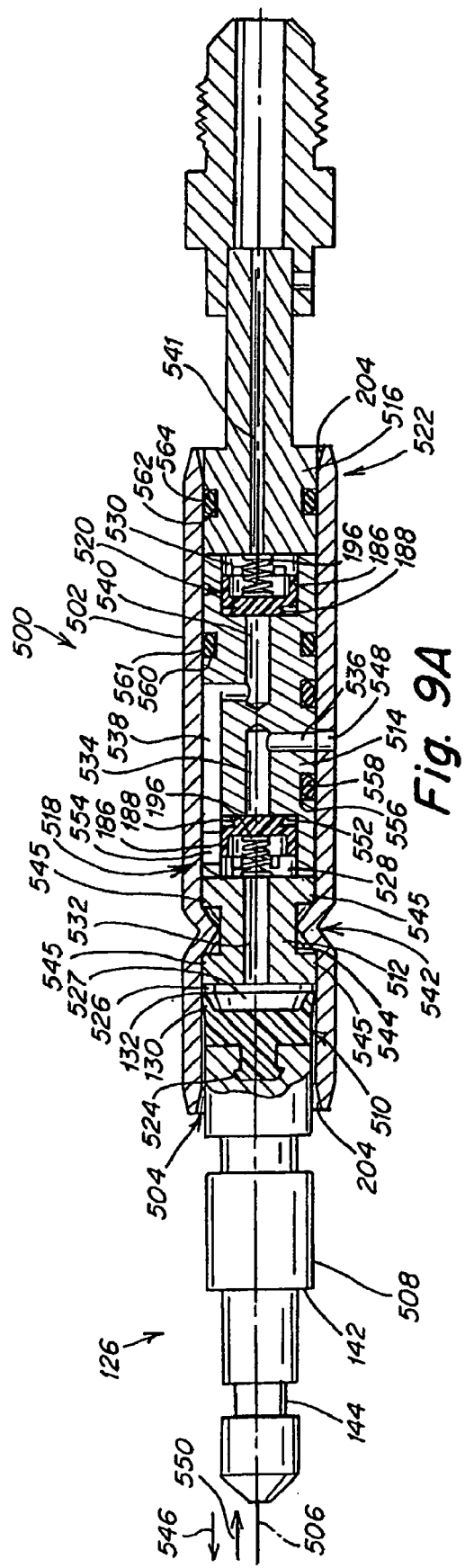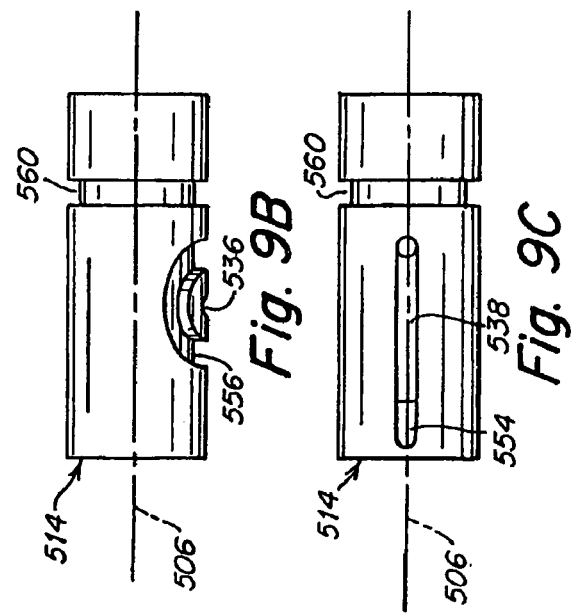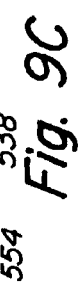
Fig. 9A
Fig. 9B
Fig. 9C

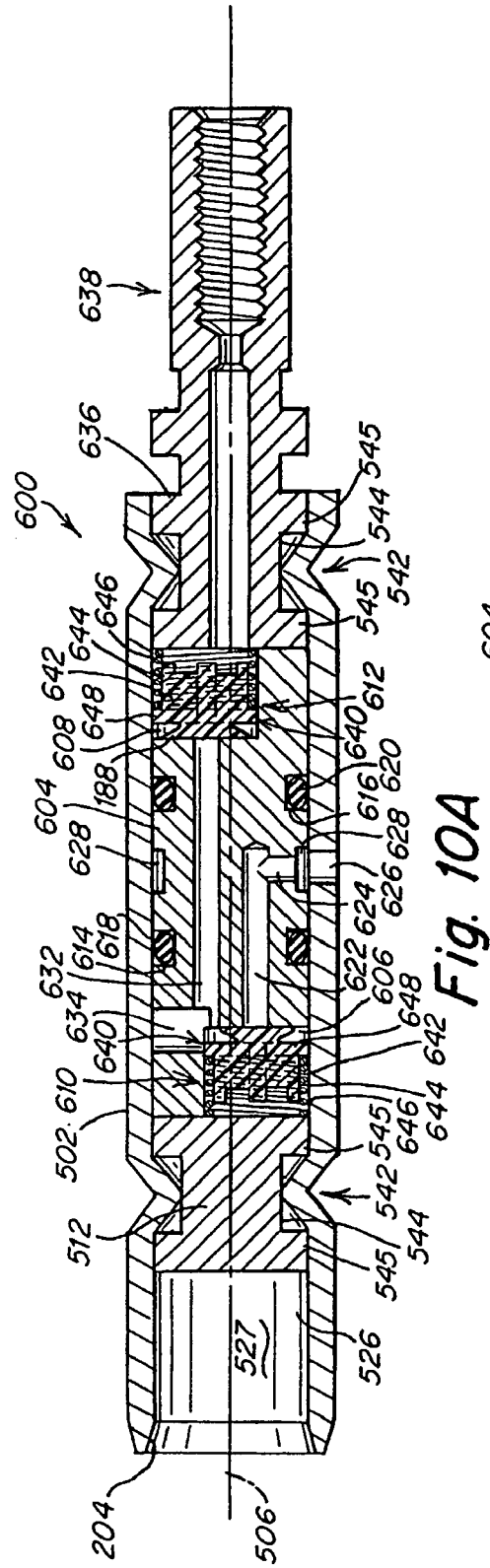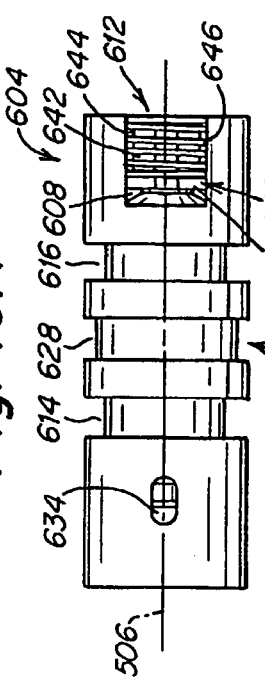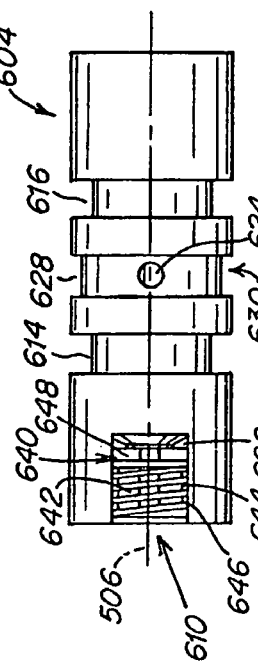

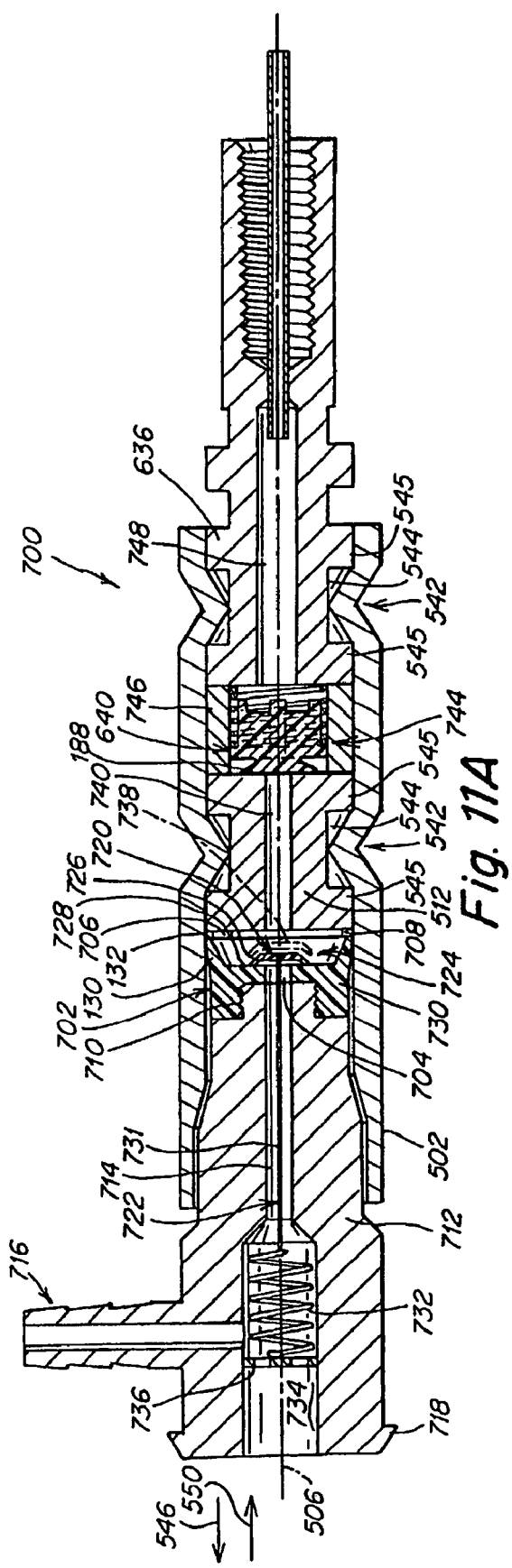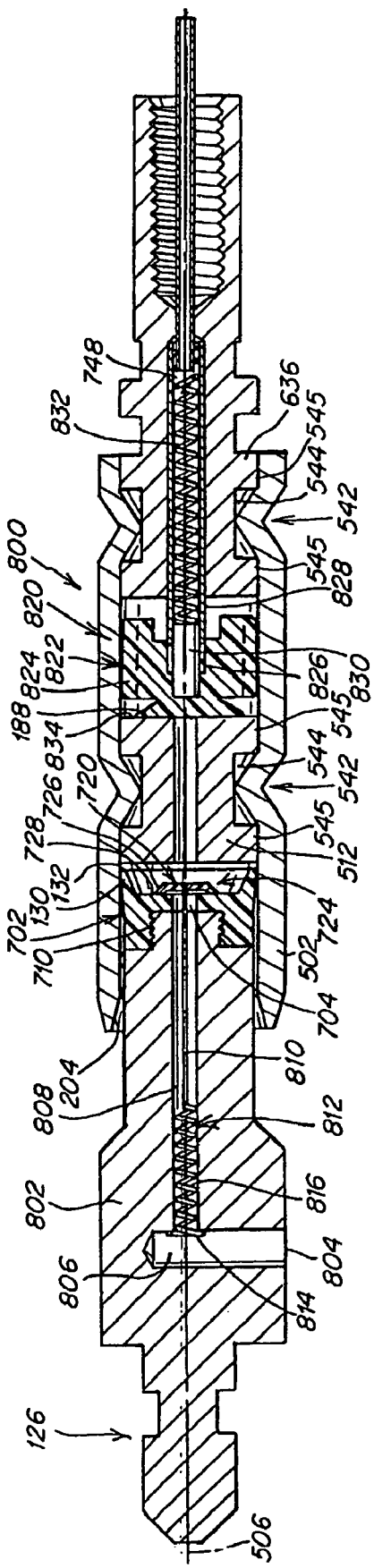

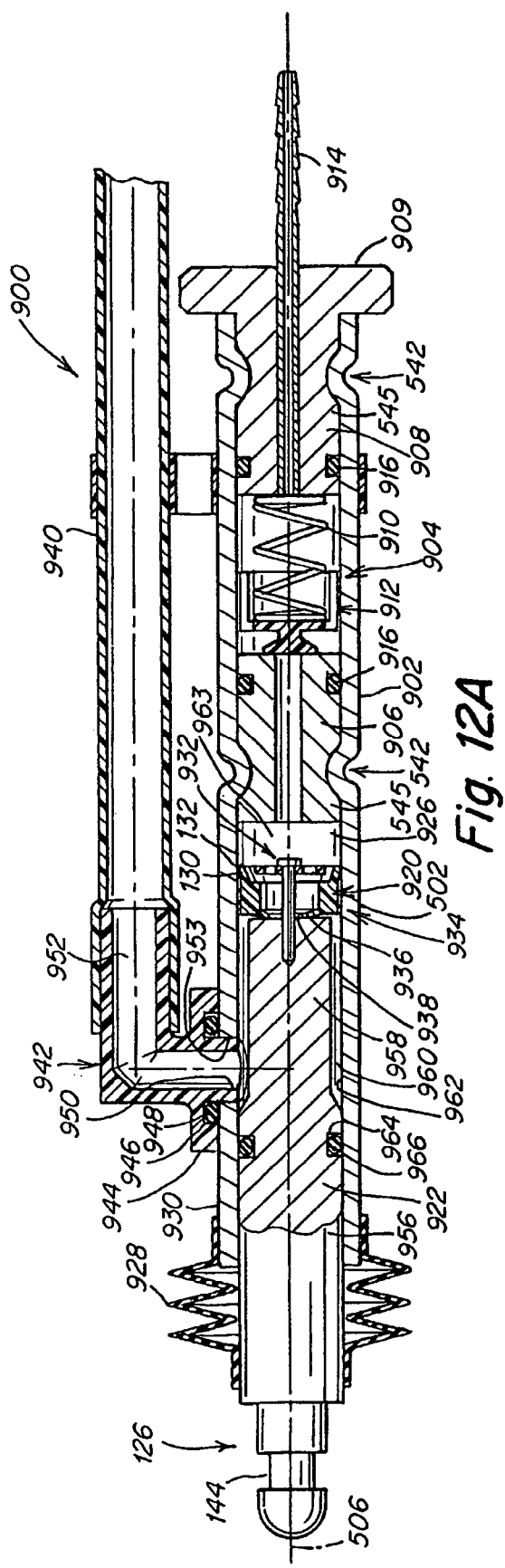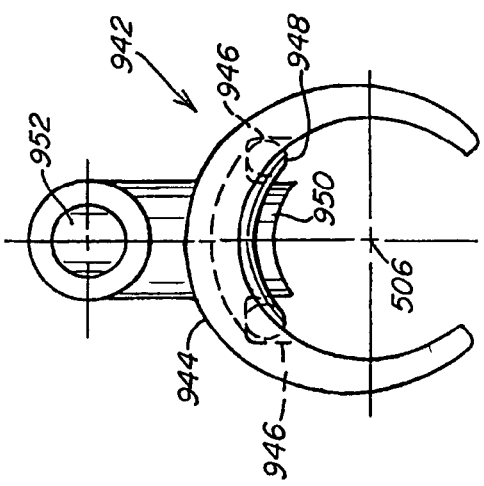

HIGH PRESSURE PUMPING CARTRIDGES FOR MEDICAL AND SURGICAL PUMPING AND INFUSION APPLICATIONS

CLAIM OF PRIORITY

This application is a continuation of U.S. application Ser. No. 10/134,970 filed Apr. 29, 2002 which claims priority to U.S. Patent Application Ser. No. 60/287,219 filed Apr. 27, 2001, each of which is incorporated by reference herein.

FIELD OF THE INVENTION

The invention relates to high pressure pumping cartridges and methods for manufacturing and utilizing the pumping cartridges, more specifically to pumping cartridges and methods for pumping or infusing a liquid for delivery to the body of a patient or a surgical or medical instrument to perform a medical treatment.

BACKGROUND

Traditionally, typical medical and surgical procedures requiring infusion or pumping of liquids to the body of a patient or to a medical or surgical instrument to perform a medical procedure utilized relatively low liquid pressure, for example liquid pressures below 100 psig. Accordingly, typical medical and surgical liquid infusion or pumping devices are not configured for or capable of generating very high liquid pressures, for example liquid pressures above 1,000 psig and up to as high as about 50,000 psig. Such traditional medical infusion and pumping applications include, for example, infusion of medications to a body of a patient, pumping of saline or other solutions to irrigation instruments for surgical lavage, pumping of blood and other physiological fluids during surgical or medical procedures, etc. A wide variety of pumping and infusions systems designed and configured for such applications, many including detachable and disposable pumping cartridges, are well known and readily available. Such pumping systems and cartridges include those employing peristaltic or tubing pumps, a variety of diaphragm and collapsible chamber pumps, and low pressure piston pumps.

Pumping systems utilized for generating very high fluid pressures, for example in the above-mentioned high pressure range, have typically been restricted primarily to industrial pumping applications. Such pumping systems typically employ fluid pumps that are not well suited for medical or surgical use because, for example, they are mechanically complex and/or expensive or difficult to manufacture and assemble, are constructed from materials or employ working fluids that are not physiologically or biologically compatible, employ pumping components that are not disposable or detachable from an expensive reusable pump drive system, employ pumping components and that are not easily cleanable and/or sterilizable.

Typical pumping systems from neither of the above-mentioned categories (i.e., relatively low pressure medical infusion and pumping systems, and high pressure industrial pumping systems) is particularly well suited for applications involving medical or surgical liquid pumping requiring high pumped liquid pressures, for example above 1,000 psig up to about 50,000 psig. Such applications include the pumping of liquids to surgical handpieces for performing high pressure liquid jet cutting and/or ablation in performing minimally invasive or open surgical procedures for example as described in the Applicants' U.S. Pat. Nos. 5,871,462; 5,944,686; 6,216,573, and 6,375,635, and for delivering a high pressure liquid to a surgical instruments employing a liquid jet powered motor for powering surgical cutting and other surgical tools, for example as described in the Applicants' co-pending U.S. patent application Ser. No. 09/480,500.

Accordingly, there remains a need in the art for pumping systems and methods for pumping and infusing high pressure liquids and fluids for performing medical and surgical treatments, which employ pumping cartridges with improved disposability, sterilizability, mechanical simplicity, ease of manufacture, and/or low per-unit cost. The present invention provides, in many embodiments, such improved pumping systems and cartridges, and further provides methods for their use in medical or surgical pumping or infusing procedures.

SUMMARY

The present invention provides, in one aspect, a number of embodiments of pumping cartridges useful for medical and surgical pumping and infusion procedures. The invention also provides methods for manufacturing and utilizing such pumping cartridges and methods for pumping or infusing liquids for delivery to the body of a patient or a surgical or medical instrument for performing a medical treatment. The invention includes, in one aspect, a series of pumping cartridges comprising cylinders and pistons constructed and arranged for sliding or reciprocating motion within the cylinders. The pistons can comprise a sealing component including a circumferential, flared sealing flange and can, in preferred embodiments, be configured to enable the pumping cartridge to generate high liquid pumping pressures, for example above 1,000 psig. Preferred embodiments of the pumping cartridges can be relatively easily manufactured at a low cost per unit and can be configured to be detachable from the pump drive unit and, most preferably, disposable after a single use.

Various compact flow path configurations are provided in the pumping cartridge embodiments described, including a Y-shaped configuration, a T-shaped configuration, and an axial configuration. Some preferred embodiments include pistons including or at least partially forming a valve and/or pistons that are relatively movable with respect to a piston rod to which they are connected. In another aspect, the invention provides valves including a valve seat and a movable sealing element able to create a seal capable of withstanding differences in fluid pressures thereacross of at least about 1,000 psi, and in some embodiments up to in excess of 10,000 psi, without substantial fluid leakage therethrough. In some embodiments the movable sealing element is concave in shape, and may be curved, to create a mechanical advantage for improved sealing performance. In yet another aspect, the invention provides methods for manufacturing axially configured pumping cartridges from thin-walled tubing. And in yet another aspect, the invention provides a series of methods for pumping or infusing a liquid for delivery to the body of a patient or a surgical or medical instrument for performing a medical treatment, for example, using the above-mentioned pumping cartridges and systems.

In one aspect, a series of methods for pumping or infusing a liquid for delivery to the body of a patient or a surgical or medical instrument are described. One method comprises delivering a liquid to a pumping cartridge comprising therein a cylinder and a piston, which is constructed and arranged for sliding motion relative to the cylinder. The pumping cartridge comprises a sealing component shaped to include a flared sealing flange portion, which is constructed and arranged to create a fluid-tight seal within the pumping cartridge during operation. The method further comprises sliding the piston relative to the cylinder so as to increase the pressure of liquid within the cylinder to a pressure of at least about 1,000 psig, and flowing the pressurized liquid from the pumping cartridge to the body of a patient or a surgical or medical instrument to perform a medical treatment. In one embodiment, the sealing component is positioned on the piston, and in another embodiment the sealing component is positioned on the cylinder. In still another embodiment, the pumping cartridge comprises a valve including a poppet comprising the sealing component thereon.

Another method for pumping or infusing a liquid for delivery to the body of a patient or a surgical or medical instrument comprises providing a pumping cartridge that comprises therein a cylinder and a piston, which is constructed and arranged for sliding relative to the cylinder. The piston includes or at least partially forms a valve and is coupled to a piston rod, which is constructed and arranged for operative association with a mechanical pump drive unit. The method further comprises detachably coupling the pumping cartridge to the pump drive unit so that the pump drive unit supports and immobilizes the pumping cartridge during operation of the pump drive unit. The method further comprises delivering a liquid to the cylinder of the pumping cartridge, sliding the piston within the cylinder to increase the pressure of the liquid within the cylinder and flowing the pressurized liquid out of the cylinder and to the body of a patient or the surgical or medical instrument to perform a medical treatment.

Yet another method for pumping or infusing a liquid for delivery to the body of a patient or a surgical or medical instrument comprises delivering a liquid to a pumping cartridge comprising therein a cylinder and a piston, which is constructed and arranged for sliding motion within the cylinder. The piston includes or at least partially forms a valve. The method further involves, with the valve in a closed position, increasing the pressure of the liquid within the cylinder to at least about 1,000 psig, without substantial leakage of the liquid through the valve, and flowing the pressurized liquid from the pumping cartridge to the body of a patient or the surgical or medical instrument to perform a medical treatment.

Another method for pumping or infusing a liquid for delivery to the body of a patient or a surgical or medical instrument comprises delivering a liquid to a pumping cartridge comprising therein a cylinder and a piston, which is constructed and arranged for sliding motion within the cylinder. The piston is coupled to a piston rod, which is drivable in reciprocating motion by a mechanical pump drive unit, such that the piston is moveable relative to the piston rod during operation. The method further comprises sliding the piston within the cylinder so as to fill a region of the cylinder with the liquid, sliding the piston within the cylinder so as to increase the pressure of the liquid within the cylinder, and flowing the pressurized liquid from the pumping cartridge to the body of a patient or the surgical or medical instrument to perform a medical treatment.

Yet another method for pumping or infusing a liquid for delivery to the body of a patient or a surgical or medical instrument comprises delivering a liquid to a pumping cartridge comprising therein a cylinder and a piston, which is constructed and arranged for sliding motion within the cylinder. The piston is coupled to a piston rod, which is drivable in reciprocating motion. The method further involves flowing the liquid through the piston to fill a region of the cylinder downstream of the piston with the liquid, sliding the piston within the cylinder to increase the pressure of the liquid within the cylinder, and flowing the pressurized liquid from the pumping cartridge to the body of a patient or the surgical or medical instrument to perform a medical treatment.

Another method for pumping or infusing a liquid for delivery to the body of a patient or a surgical or medical instrument comprises delivering a liquid to a pumping cartridge comprising therein a cylinder and a piston, which is constructed and arranged for sliding motion within the cylinder. The piston comprises a sealing component, which is constructed and arranged to contact an inner surface of the cylinder. The method further involves reciprocating the piston within the cylinder to effect pumping of the liquid by the pumping cartridge such that for a first interval of time after commencement of the pumping, a seal created by contact between the sealing component of the piston and the inner surface of the cylinder leaks liquid therethrough at a leakage rate within a first range of values, for a second, subsequent interval of time leaks liquid therethrough at a leakage rate within a second range of values, each value therein being less than the values within the first range, and for a third, subsequent interval of time leaks liquid therethrough at a leakage rate within a third range of values, each value therein being greater than the values within the second range. During at least part of the reciprocating step, liquid pumped by the pumping cartridge is flowed to the body of a patient or the surgical or medical instrument to perform a medical treatment.

In another aspect, a series of pumping cartridges is described. One pumping cartridge comprises a cylinder, a piston rod, and a piston coupled to the piston rod, which is constructed and arranged for reciprocating motion within the cylinder. The piston comprises a sealing component shaped to include a circumferential, flared sealing flange portion extending axially away from the portion, to which it is attached, of a main body of the piston. The sealing flange portion is constructed and arranged to make contact with an inner surface of the cylinder thereby creating a seal between the sealing flange portion and the inner surface able to withstand a pressure differential of at least about 1,000 psi without substantial leakage of fluid therethrough during operation of the pumping cartridge. The sealing flange portion of the piston is constructed of a non-elastomeric polymeric material and has a maximum outer diameter large enough to enable at least a portion of the sealing flange portion to be in essentially continuous contact with the inner surface of the cylinder during reciprocation of the piston. The piston is also shaped and positioned within the cylinder so that all fluid-contacting surfaces oriented essentially perpendicular to the longitudinal axis of the cylinder that are not directly supported by the piston rod have a minimum cross-sectional thickness exceeding the minimum cross-sectional thickness of the sealing flange portion of the piston.

Another pumping cartridge comprises a cylinder and a piston, which are constructed and arranged for reciprocating motion relative to each other. The pumping cartridge comprises a sealing component shaped to include a circumferential, flared sealing flange portion extending away from a portion, to which it is attached, of a main body, such that a first surface of the flared sealing flange portion adjacent to and facing a surface with which it is in sliding contact forms a first angle with respect to the longitudinal axis of the cylinder, and a second surface of the flared sealing flange portion facing away from the surface with which it is in sliding contact forms a second angle with respect to the longitudinal axis of the cylinder. The first angle exceeds 0 degrees. The second angle does not exceed 90 degrees. The second angle exceeds the first angle, and the sealing flange portion of the piston is constructed of a non-elastomeric material.

Yet another pumping cartridge comprises a cylinder, a piston rod, and a piston coupled to the piston rod, which is constructed and arranged for reciprocating motion within the cylinder. The piston comprises an integrally formed, circumferential, flared sealing flange portion extending axially away from a portion, to which it is attached, of a main body of the piston. The piston has a maximum, fluid-wetted diameter essentially equal to an inner diameter of the cylinder, when the piston is installed in operative association within the cylinder. The piston is constructed of a non-elastomeric material, and the flared sealing flange portion of the piston has a maximum outer diameter, when relaxed prior to installation of the piston within the cylinder, at least as great as the inner diameter of the cylinder.

Another pumping cartridge comprises a cylinder and a piston, which is constructed and arranged for reciprocating motion within the cylinder. The piston comprises a sealing component shaped to include a circumferential, flared sealing flange portion. The sealing flange portion is constructed and arranged to make contact with an inner surface of the cylinder thereby creating a seal between the sealing flange portion and the inner surface able to withstand a pressure differential of at least about 10,000 psi without substantial leakage of fluid therethrough during operation of the pumping cartridge. The sealing flange portion of the piston is constructed of a non-elastomeric polymeric material. The sealing flange portion of the piston has a maximum outer diameter large enough to enable at least a portion of the sealing flange portion to be an essentially continuous contact with the inner surface of the cylinder during reciprocation of the piston. The piston is shaped and positioned within the cylinder so that all fluid-contacting surfaces oriented essentially perpendicular to the longitudinal axis of the cylinder that are not directly supported by the piston rod have a minimum cross-sectional thickness exceeding the minimum cross-sectional thickness of the sealing flange portion of the piston.

Yet another pumping cartridge comprises a cylinder, a piston rod, and a piston coupled to the piston rod, which piston is constructed and arranged for reciprocating motion within the cylinder. The piston comprises a sealing component shaped to include a circumferential flared sealing flange portion. The sealing flange portion is constructed and arranged to make contact with an inner surface of the cylinder, thereby creating a seal between the sealing flange portion and the inner surface able to withstand a pressure differential of at least about 1,000 psi without substantial leakage of fluid therethrough during operation of a pumping cartridge. The sealing flange portion of the piston is constructed of a non-elastomeric polymeric material. The sealing flange portion of the piston has a maximum outer diameter large enough to enable at least a portion of the sealing flange portion to be in essentially continuous contact with the inner surface of the cylinder during reciprocation of the piston. Inner, piston rod-facing surfaces of the piston are shaped and arranged such that upon coupling of the piston to the piston rod, essentially all of the inner surfaces of the piston are in direct contact with the piston rod or a securing member that is in contact with the piston rod. The piston is shaped and positioned within the cylinder so that all fluid-contacting surfaces oriented essentially perpendicular to the longitudinal axis of the cylinder that are not directly supported by the piston rod have a minimum cross-sectional thickness exceeding the minimum cross-sectional thickness of the sealing flange portion of the piston.

Another pumping cartridge comprises a cylinder and a piston, which is constructed and arranged for reciprocating motion within the cylinder. The piston comprises a sealing component shaped to include a circumferential, flared sealing flange portion extending axially away from a portion, to which it is attached, of a main body of the piston. The sealing flange portion is constructed and arranged to make contact with an inner surface of the cylinder thereby creating a seal between the sealing flange portion and the inner surface of the cylinder. The sealing flange portion of the piston is constructed of a non-elastomeric polymeric material having a tensile strength of between about 5,000 psi and about 50,000 psi, and a flexural modulus of between about 100,000 psi and about 700,000 psi at the temperature of operation of the pumping cartridge. The piston is shaped and positioned within the cylinder so that all fluid-contacting surfaces oriented essentially perpendicular to the longitudinal axis of the cylinder that are not directly supported by the piston rod have a minimum cross-sectional thickness exceeding the minimum cross-sectional thickness of the sealing flange portion of the piston.

Yet another pumping cartridge comprises a cylinder, piston rod, and a piston coupled to the piston rod, which piston is constructed and arranged for reciprocating motion within the cylinder. The piston comprises a sealing component shaped to include a circumferential flared sealing flange portion, which is constructed and arranged to make contact with an inner surface of a cylinder thereby creating a seal between the sealing flange portion and the inner surface of the cylinder. The sealing flange portion of the piston is constructed of a non-elastomeric polymeric material having a tensile strength of between about 5,000 psi and about 50,000 psi, and a flexural modulus of between about 100,000 psi and about 700,000 psi at the temperature of operation of the pumping cartridge. Inner, piston rod-facing surfaces of the piston are shaped and arranged such that upon coupling of the piston to the piston rod, essentially all of the inner surfaces of the piston are in direct contact with the piston rod or a securing member that is in contact with the piston rod. The piston is shaped and positioned within the cylinder so that all fluid-contacting surfaces oriented essentially perpendicular to the longitudinal axis of the cylinder that are not directly supported by the piston rod have a minimum cross-sectional thickness exceeding the minimum cross-sectional thickness of the sealing flange portion of the piston.

Another pumping cartridge comprising a cylinder and a piston rod, where the cylinder and piston rod are constructed and arranged for reciprocating motion with respect to each other is disclosed. The pumping cartridge also comprises a sealing ring coupled to or integral with an inner wall of the cylinder. The sealing ring comprises a sealing component shaped to include a circumferential flared sealing flange portion extending axially away from a portion, to which it is attached, of a sealing component support element. The sealing flange portion is constructed and arranged to make contact with an outer surface of the piston rod thereby creating a seal between the sealing portion and the outer surface of the piston rod, wherein the sealing flange portion of the sealing ring is constructed of a non-elastomeric polymeric material having a tensile strength of between about 5,000 psi and about 50,000 psi, and a flexural modulus of between about 100,000 psi and about 700,000 psi at the temperature of operation of the pumping cartridge.

Another pumping cartridge comprises a pump chamber and at least one valve comprising a valve seat and a sealing element. The sealing element comprises a concave occluding surface positioned to face the valve seat when the valve is assembled in an operative configuration.

Yet another pumping cartridge comprises a pump chamber and at least one valve comprising a valve seat and a sealing element. The sealing element comprises a valve seat-facing occluding surface including a circumferential sealing lip projecting away from a portion of the occluding surface. The sealing lip is constructed and positioned to make sealing contact with the valve seat thereby creating a seal, when the valve is positioned in a closed configuration. The seal is capable of withstanding a pressure differential of at least about 1,000 psi without substantial fluid leakage therethrough.

Another pumping cartridge comprises a length of thin-walled tubing forming a main body portion of the pumping cartridge. An axial bore of the tubing defines a cylinder, at least part of which cylinder comprises a pump chamber. The pumping cartridge further comprises a piston constructed and arranged for sliding motion within the cylinder. The pumping cartridge further comprises an inlet check valve and an outlet check valve. The inlet and outlet check valves are constructed and positioned to control the direction of flow of a fluid being pumped within the pumping cartridge. Each check valve is at least partially disposed within the cylinder such that essentially all of the moving parts of each check valve are essentially completely contained within the cylinder. The pumping cartridge is configured to be removably coupled to a re-useable, reciprocating pump drive system. The pumping cartridge is constructed and arranged to generate fluid pressures of the pumped fluid in the pump chamber of at least about 1,000 psig during operation.

Yet another pumping cartridge comprises a cylinder and a piston, which is constructed and arranged for reciprocating motion within the cylinder. The piston includes or forms at least part of a valve, which is constructed and positioned to act as an inlet valve to the cylinder of a fluid being pumped by the pumping cartridge when it is in operation. The pumping cartridge is shaped and configured to be removably coupled to a reusable, reciprocating pump drive unit, such that, upon coupling, the pumping cartridge is supported and immobilized by the pump drive unit.

Another pumping cartridge comprises a cylinder, a piston rod, and a piston coupled to the piston rod, which piston is constructed and arranged for reciprocating motion within the cylinder. The piston rod is constructed and positioned to apply a force to the piston to drive the motion of the piston during operation. The piston is coupled to the piston rod via a coupling permitting relative motion between the piston and the piston rod during at least a part of the reciprocating motion of the piston within the cylinder. The piston includes a sealing component, which is constructed and arranged to make contact with an inner surface of the cylinder thereby creating a sliding seal between the sealing component and the inner surface of the cylinder. The seal is capable of generating a differential in pressure within the cylinder of the fluid being pumped of least about 1,000 psi, when the pumping cartridge in operation.

Yet another pumping cartridge comprises a cylinder and a piston, which is constructed and arranged for reciprocating motion within the cylinder. An inner surface of the cylinder, at least one end thereof, is beveled.

Another pumping cartridge comprises a cylinder and a piston, which is constructed and arranged for reciprocating motion within the cylinder. An inner surface of the cylinder includes a piston storage region positioned proximal to a pump chamber portion of the cylinder. The piston storage region comprises a circumferential indent having a shape and contour complimentary to the shape and contour of an outer, cylinder wall-facing surface of the piston and having a maximum inner diameter exceeding a maximum outer diameter of the piston, when the piston is in a relaxed configuration prior to insertion in the cylinder.

In another aspect, a pumping system is described. The pumping system comprises a removable pumping cartridge comprising a main body portion comprising a pump chamber therein and at least one valve in fluid communication with the pump chamber, when the pumping cartridge is assembled and configured for operation. The main body portion of the pumping cartridge comprises an outer surface including at least a first bore therein. The first bore contains at least a portion of a body portion of the valve, when the pumping cartridge is assembled and configured for operation. The pumping system further comprises a support nest structure, which is constructed and arranged to be coupled to a re-usable pump drive unit. The support nest structure has a shape and configuration selected to couple the pumping cartridge in operative association with a pump drive unit. The support nest structure includes at least one valve securing component, which is constructed and arranged to secure at least one valve to the main body portion of the pumping cartridge, when the pumping cartridge is coupled in operative association with the support nest structure, such that a fluid-tight seal, capable of withstanding a difference in pressure across the seal of at least about 1,000 psi, without substantial fluid leakage therethrough, is created between the body portion of the valve and the bore of the main body portion of the pumping cartridge containing the valve only upon coupling of the pumping cartridge in operative association with the support nest structure.

In another aspect, a device comprising a cylinder, a piston rod and a piston coupled to the piston rod, which piston is constructed and arranged for sliding motion within the cylinder, is described. The piston rod is constructed and positioned to apply a force to the piston to drive the motion of the piston during operation. The piston is coupled to the piston rod via a coupling permitting relative motion between the piston and the piston rod during at least part of the motion of the piston within the cylinder. The piston comprises an integral sealing component, which is constructed and arranged to make contact with an inner surface of the cylinder thereby creating a sliding seal between the sealing component and the inner surface of the cylinder. The piston is formed of a polymeric material.

In another aspect, a pumping cartridge comprising a cylinder, a piston rod, and a sealing ring coupled to or integral with an inner wall of the cylinder is disclosed. The sealing ring comprises a sealing component shaped to include a circumferential, flared sealing flange portion extending axially away from a portion, to which it is attached, of a sealing component support element. The sealing flange portion is constructed and arranged to make contact with an outer surface of the piston rod thereby creating a seal between the sealing flange portion and the outer surface able to with stand a pressure differential of at least about 1000 psi without substantial leakage of fluid therethrough during operation of the pumping cartridge.

In another aspect, a series of valves are described. One valve comprises a valve seat and a movable sealing element comprising an occluding surface, facing the valve seat, which occluding surface is concave in shape.

Another valve comprises a valve seat and a movable sealing element comprising a valve seat-facing occluding surface including a circumferential sealing lip projecting away from a portion of the occluding surface. The sealing lip is constructed and positioned to make sealing contact with the valve seat thereby creating a seal, when the valve is positioned in a closed configuration. The seal is capable of withstanding a pressure differential of at least about 1,000 psi without substantial leakage therethrough. In one such embodiment, an O-ring may comprise the circumferential sealing lip.

In another aspect, a method for fabricating a pump cartridge from a length of thin-walled tubing is disclosed. The method comprises inserting at least a portion of a body portion of a valve at least partly into the tubing and securing the valve within the tubing by crimping the tubing onto the body portion of the valve, thereby creating a circumferential, essentially leak-tight seal between the tubing and the body of the valve, without the need for any supplemental seals.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 9A is a schematic, cross-sectional illustration of one embodiment of an axially configured pumping cartridge;

FIG. 9B is a schematic illustration of an insert of the axially configured pumping cartridge of FIG. 9A, in a first orientation;

FIG. 9C is a schematic illustration of the insert of FIG. 9B, as viewed from above;

FIG. 10A is a schematic, cross-sectional illustration of a portion of another embodiment of an axially configured pumping cartridge;

FIG. 10B is a schematic illustration of an insert of the pumping cartridge of FIG. 10A, as viewed from above;

FIG. 10C is a schematic illustration of the insert of FIG. 10B, as viewed from below;

FIG. 11A is a schematic, cross-sectional illustration of an axially configured pumping cartridge including a valved piston;

FIG. 11B is a schematic, cross-sectional illustration of another embodiment of an axially configured pumping cartridge including a valved piston;

FIG. 12A is a schematic, cross-sectional illustration of an axially configured pumping cartridge including a floating piston forming an inlet valve to the pumping cartridge;

FIG. 12B is a schematic illustration of an inlet line clamp component of the pumping cartridge of FIG. 12A;

DETAILED DESCRIPTION

Figure 1:
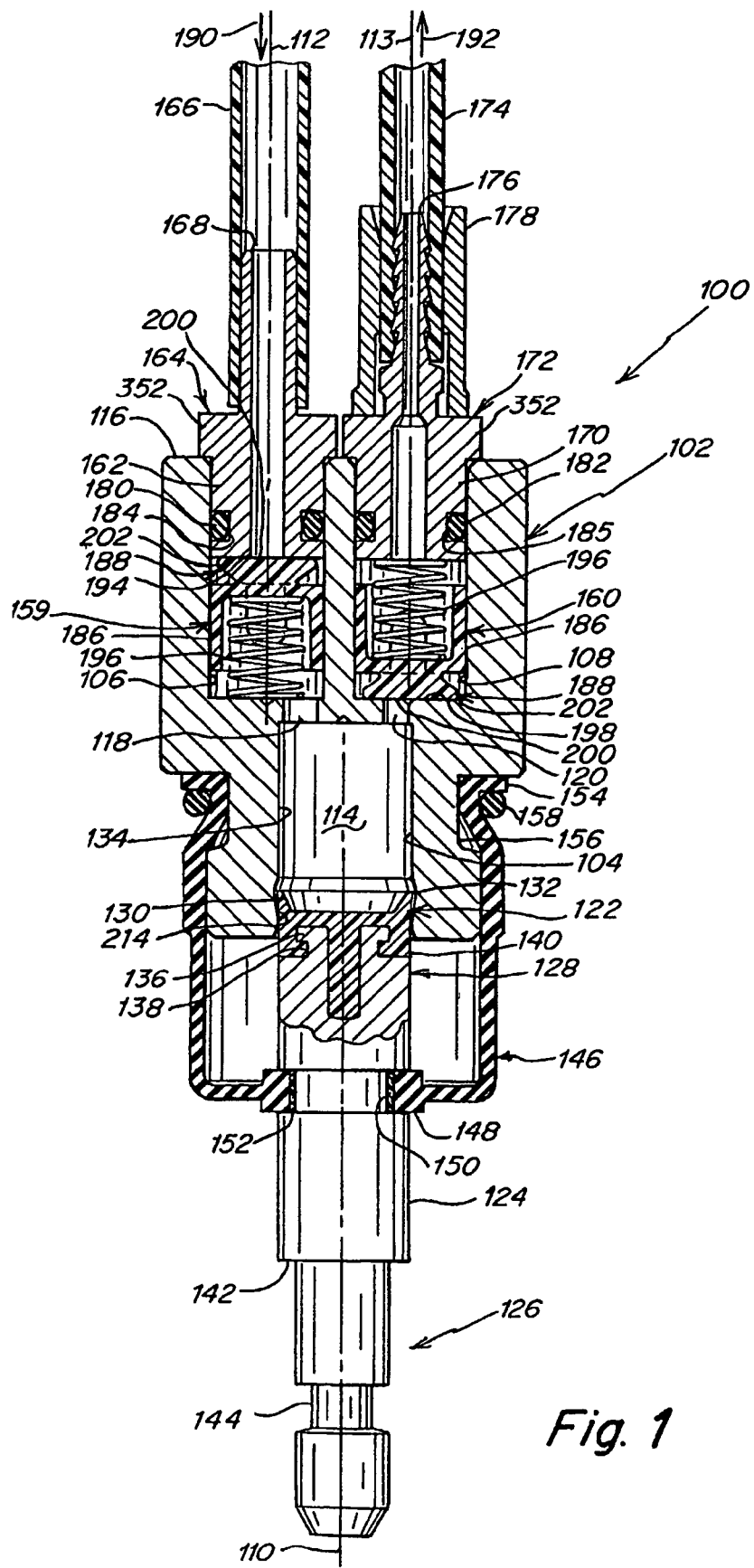
FIG. 1 is a schematic, cross-sectional illustration of a pumping cartridge having a Y-shaped configuration.

The present invention provides a variety of pumping systems that can be useful in a variety of fluid pumping, fluid delivery, or fluid infusion applications. The pumping systems provided by the present invention, in preferred embodiments, are designed, constructed, and configured to include replaceable and/or disposable pumping cartridges that can be detachably coupled to a reusable mechanical pump drive unit. The pumping cartridges are also preferably constructed of low-cost, easily sterilizable materials and components. As such, the pumping cartridges provided according to the invention can be advantageously utilized in pumping, infusion, fluid delivery, etc. systems wherein sterile or pure fluid handling is important and wherein disposability and/or replaceability of the process fluid-wetted pumping components is mandated or desirable. Accordingly, the pumping systems and pumping cartridges described herein are especially well suited for applications involving, for example, pumping and delivery of food items, and especially for methods involving the pumping or infusing of a liquid for delivery to the body of a patient or a surgical or medical instrument.

As discussed in the Background, pumping systems including disposable pumping cartridges designed for use in medical or surgical pumping or infusing applications are known, generally, in the art. However, as previously mentioned, such systems are generally limited to relatively low pressure pumping or infusion applications (e.g. less than 100 psig). As discussed in more detail below, preferred embodiments of pumping cartridges provided according to the present invention enable generation of fluid pumping pressures of at least about 1000 psig, and in some preferred embodiments of at least about 5000 psig, in other preferred embodiments of at least about 8000 psig, in other preferred embodiments of at least about 15,000 psig, in other embodiments of at least about 20,000 psig, in other embodiments of at least about 30,000 psig, and yet in other embodiments of at least about 50,000 psig, while still being readily detachable and replaceable from a mechanical pump drive unit/counsel and while being constructed of materials and utilizing construction methods enabling a low enough cost per unit to allow the pumping cartridges to be configured and designed for disposal after a single use.

The pumping systems and pumping cartridges provided according to the present invention are particularly well suited for methods involving the pumping of liquids at high pressure to instruments creating or utilizing a fluid or liquid jet for performing a medical or surgical procedure. For example, the pumping systems and pumping cartridges described herein can be well suited for use in delivering high pressure liquids to surgical or medical instruments, for example surgical handpieces positioned remote from the pumping cartridge and connected in fluid communication thereto via a length of flexible tubing, that can include at least one nozzle for forming a liquid cutting jet and/or a liquid jet forming part of a hydrodynamic motor for driving a surgical tool, for example a cutting or abrading tool. In some such embodiments, the pumping cartridges can be employed in a method for pumping liquids to a liquid jet-forming surgical handpiece and directing the liquid jet formed by the handpiece onto tissue of a patient to cut, ablate, delaminate, abrade, emulsify, and/or macerate the tissue. In other embodiments, the pumping cartridges can be employed in a method for pumping liquids to a liquid jet-powered surgical handpiece utilizing a liquid jet to power a rotating cutting or abrading tool of the handpiece. Exemplary surgical instruments utilizing and/or creating liquid jets for use in various surgical procedures that are particularly well adapted for use with the pumping systems and cartridges provided according to the present invention are described in detail in the applicants' U.S. Pat. Nos. 5,944,686; 6,216,573; and 6,375,635 and in the applicants' co-pending U.S. patent application Ser. Nos. 09/480,500 and 09/480,762.

It should be understood that although the pumping cartridges and systems described herein are particularly well suited for the above-described surgical or medical applications involving high pressure liquid jets, the systems and pumping cartridges provided according to the present invention can be used for other purposes, especially where delivery of high pressure fluids is desired and where it is desirable to utilize a replaceable and/or disposable pumping cartridge for clean/sterile fluid handling that can have a relatively low per-unit cost. Those of ordinary skill in the art will readily envision many applications in the food, pharmaceutical, and other industries where such pumping systems and pumping cartridges can be advantageously utilized.

Preferred embodiments of the pumping cartridges provided according to the invention are configured as piston pumping cartridges including therein a cylinder and a piston, which is constructed and arranged for sliding motion and/or reciprocation within the cylinder. The term "piston" as used herein refers to a component of a pumping cartridge having a surface that is wetted by the liquid or fluid being pumped by the pumping cartridge and that is configured for sliding motion within the cylinder, whereby the component applies a force to the fluid/liquid within the cylinder thereby increasing its pressure and/or kinetic energy. A "fluid" when used in the present context can comprise a liquid, gas, supercritical fluid, slurry, suspension, or any mixture of the above, and refers to a thermodynamic state of the material present in the regions of the cylinder at the temperature and pressure at which a pumping cartridge is used in operation. In typical embodiments, for example those involving the pumping or infusing of materials to the body of a patient or a surgical or medical instrument, the fluid being pumped or infused will be a liquid at the temperature and pressure of operation of the pumping cartridge. Typically, when the pumping cartridge is utilized for surgical or medical uses, the liquid will comprise a medically, biologically, and/or physiologically compatible liquid, such as, for example, normal saline, phosphate buffered saline, sterile water, etc. "Constructed and arranged for sliding motion within the cylinder," as used in the above context describing the configuration of the piston and cylinder refers to the piston being slidably moveable within the cylinder upon installation of the piston within the cylinder of the pumping cartridge.

In certain preferred embodiments, as described in more detail below, the pumping cartridge is constructed to include a sealing component that is shaped to include a flared sealing flange portion, which is constructed and arranged to make contact with a surface within the pumping cartridge to create a seal. A "sealing component" as used herein refers to a component of a pumping cartridge configured and positioned to create a fluid-tight seal within the pumping cartridge. In certain embodiments, the sealing component is a component of a piston configured and positioned on the piston such that the component, or at least a portion thereof, contacts an inner surface of a cylinder, when the piston is installed within the cylinder, and thereby creates a seal between the piston and the cylinder. In other embodiments, the sealing component is a component of a cylinder configured and positioned on the cylinder such that the component, or at least a portion thereof, contacts a surface of a piston and/or a surface of a piston rod, when the piston/piston rod is installed within the cylinder, and thereby creates a seal between the piston and the cylinder. A "seal" as used in the above context refers to a region of contact between two adjacent components, which region of contact separates the cylinder into a first and second region and provides an increased resistance to fluid flow through the seal from the first to the second region of the cylinder or vise versa.

A "flared sealing flange" or "flared sealing flange portion" of a sealing component of the piston refers to a portion of the piston shaped and configured to extend away from a main body portion of the piston axially and/or distally, and typically also radially. For example, a flared sealing flange as used herein would not encompass a piston utilizing a standard O-ring as a sealing component, since an O-ring generally is configured such that it extends from the main body of a piston, around which it forms a circumferential peripheral sealing element, only radially (i.e., toward the inner surface of the cylinder) and not axially or distally.

A "sealing component support element" is any structural support element to which the sealing component flared sealing flange portion is coupled (e.g., a piston main body, a cylinder-engaging main body portion of a cylinder sealing ring, or a valve poppet body).

The phrase "constructed and arranged to make contact with an inner surface of the cylinder," as used in the context above, refers to the piston being configured so that, upon assembly of the piston within the cylinder, a surface of the sealing component makes direct physical contact with at least a portion of the inner surface of the cylinder. As mentioned above, preferred pumping cartridges provided according to the invention are configured and designed so that, during operation, the piston can be slid within the cylinder of the pumping cartridge so as to increase the pressure of liquid within the cylinder to a pressure of at least about 1000 psig for subsequent delivery to an outlet line in fluid communication with the pumping cartridge.

Analogously, a "flared sealing flange", or "flared sealing flange portion" of a sealing component of the cylinder refers to a portion of the cylinder shaped and configured to extend away from a wall of the cylinder axially and/or distally, and typically also radially.

The phrase "constructed and arranged to make contact with a surface of the piston or constructed and arranged to make contact with a surface of the piston rod" as used in the context above, refers to the cylinder being configured so that, upon assembly of the piston/piston rod within the cylinder, a surface of the sealing component makes direct physical contact with at least a portion of the surface of the piston/piston rod.

In some preferred embodiments, where the piston/piston rod includes a sealing component and where it is desirable for the pumping cartridge to be able to generate relatively high fluid pumping pressures, for example pressures above 1000 psig, the piston is, preferably, coupled to a piston rod, which, in turn, is coupled to a mechanical pump drive unit for driving the piston and the rod in a reciprocating motion. In certain such embodiments, as described in more detail below, the piston can be configured as a cap, annular ring, or other type of component that is integrally formed with the sealing component as a single piece from, for example, a resilient material able to create a sliding seal, while the piston rod can comprise a rigid, structurally supportive component constructed and configured for supporting and driving the piston within the cylinder.

A "piston rod" as used herein refers to a component of the pumping cartridge, which may be mechanically connected to a piston (if present) and a source of force for driving the piston rod and any piston connected thereto. A "piston rod" can be a separate or separable element from the piston or, alternatively, the piston and the piston rod can be integrally formed as a single element. "Coupled to," when used in the context of the piston being coupled to the piston rod refers to the piston and piston rod being associated together such that the piston rod is able to assert a force upon the piston so as to move the piston within the cylinder. "Coupled to" includes connections comprising rigid attachment and integral formation, e.g. a single-piece piston and piston rod assembly would also be "coupled" together, wherein the piston and piston rod move together at the same speed at all times during the pumping cycle, and also encompasses connections allowing relative motion to occur between the piston and piston rod during the pumping cycle, or a portion thereof. It should be understood that the piston may be "coupled to" the piston rod even without direct contact between the piston and the piston rod. For example, various spacers, washers, spanning elements, etc. can, if desired or advantageous, be interposed between the piston and the piston rod within the meaning of "coupled to" given above.

As mentioned previously, preferred embodiments of the pumping cartridges provided according to the present invention are configured to permit detachable coupling of the pumping cartridge to a reusable pump drive unit, for example, a reciprocating pump drive unit. "Detachably coupled" as used herein in the context of the association between the pumping cartridge and the mechanical pump drive unit of the pumping system refers to the pumping cartridge being able to be installed and removed from the pump drive unit by an operator of the system without requiring disassembly of the pump drive unit and, most preferably, without the need for the use of any tools.

In such configurations, it is preferable that any piston rod of the pumping cartridge be constructed and arranged for operative association with the mechanical pump drive unit. The phrase "constructed and arranged for operative association with a mechanical pump drive unit" as used in the above context refers to the piston rod being coupled to the pump drive unit so as to enable the pump drive unit to apply a force to, and move the piston rod, and, if present, piston within the cylinder to effect pumping and delivery of fluids from the pumping cartridge.

In some especially preferred embodiments, the pumping cartridge is detachably coupled to the pump drive unit and the pump drive unit supports and immobilizes the pumping cartridge during operation of the system. "Supports and immobilizes" as used in the above context refers to the pump drive unit, or pumping cartridge supporting and/or nesting component, or at least some portion thereof, enabling the pumping cartridge to withstand forces/pressures asserted upon the pumping cartridge during operation by absorbing, resisting, and/or redirecting at least a portion of such forces, thereby preventing relative motion between at least one component of the pumping cartridge and the pump drive unit, as well as, in certain embodiments, preventing failure or leakage of fluid from the pumping cartridge.

In some preferred embodiments of the inventive pumping systems providing detachably coupled pumping cartridges, the pumping cartridge, or certain components thereof, are configured and constructed for a single use only, such that methods for pumping or infusing fluids/liquids utilizing such pumping cartridges will include a final step of disposing of at a portion of the pumping cartridge after a single use. As discussed in more detail below, pumping cartridges can be constructed and configured for single use only by, for example, including pistons or cylinders having sealing components that are sacrificial and subject to wear during operation so that they will fail after operation for a period of time equal to, or somewhat but not very much greater than, a desired service life for a particular single-use application. For example, when the pumping cartridge is utilized for a surgical procedure (e.g. for delivering a high pressure liquid to a liquid jet-powered surgical cutting device), the sealing component of the piston or cylinder can be constructed so that the pumping cartridge is able to generate a desirable fluid delivery pressure with an acceptable leakage rate for a period of at least about an hour but not, for example, exceeding 24 hours, so that the pumping cartridge will need to be replaced after a single surgical procedure.

In other embodiments, the pumping cartridge could, instead, include a sealing component constructed of more durable materials so that the pumping cartridge could be utilized for more extended periods and/or for several surgical procedures. In such embodiments, it is desirable that the pumping cartridge be configured for easy disassembly to allow for cleaning and sterilization of the pumping cartridge between uses. In addition, in some such embodiments, a component subject to a particularly high rate of wear, for example the sealing component, can be configured to be easily and readily replaceable within the pumping cartridge. Accordingly, in some such embodiments, a portion of the pumping cartridge, as opposed to the entire pumping cartridge, can be constructed and provided for replacement after a single use. For such embodiments, preferably, portions of the pumping cartridge which are configured for multiple uses will comprise non-fluid-wetted components so as to minimize any cross contamination between uses.

In any event, for embodiments wherein the detachably coupled pumping cartridges are utilized as part of a method for pumping or infusing a liquid for delivery to the body of a patient or surgical or medical instrument to perform a medical treatment, the pumping cartridge should, after manufacturing but prior to utilization for pumping, be sterilized, for example by heat sterilization, radiation sterilization, chemical sterilization, or the like, as would be apparent to those of ordinary skill in the art. In general, embodiments of the pumping cartridge described as being "constructed and configured to be disposed of after a single use" are characterized as being constructed of relatively low-cost materials and including at least one component therein having a useful service life not greatly exceeding a maximum contemplated period of single use for an intended application.

The pumping cartridges provided according to the present invention can be configured in a variety of ways, as discussed in more detail below. For example, in some embodiments, the pumping cartridge can be configured with a "T-shaped" flow path configuration, having a coaxial inlet flow path and outlet flow path, each in fluid communication with a cylinder forming a pump chamber, which has a longitudinal axis essentially perpendicular to the longitudinal axis of the inlet and outlet flow path. In another configuration, the pumping cartridge includes a "Y-shaped" flow path, in which the pumping cartridge has a main body including two parallel flow paths therein "an inlet and an outlet", disposed side-by-side and distal to the pump chamber with parallel longitudinal axes that are also parallel to the longitudinal axis of the cylinder forming the pump chamber.

In some preferred embodiments, the pumping cartridge has an axially-aligned configuration, and is formed, at least in part, from an elongated tube/thin-walled tubing. In such embodiments, the cylinder forming the pumping chamber in which the piston and/or piston rod reciprocates and at least one of an inlet and outlet flow path of the pumping cartridge are coaxially aligned and/or formed by, or contained within, a common bore of the elongated tube/thin-wall tubing. The terms "elongated tube" and "thin-wall tubing," when used to describe a main body portion of a pumping cartridge provided according to the invention refer to the pumping cartridge main body being formed from an annular tube having a wall thickness that is substantially less than the outer diameter of the tube and an outer diameter that is substantially less than the length of the tube. In certain preferred embodiments, such pumping cartridges can be constructed of low-cost, readily-available, biologically-compatible thin-wall tubing, for example stainless steel tubing, enabling such embodiments of the pumping cartridge to be manufactured at a very low per-unit cost. In some embodiments, a supporting tube (disposable or non-disposable) may be used to help support the thin-wall tubing.

Generally, the inlet and outlet flow paths of the pumping cartridges provided according to the invention will each include at least one valve therein to provide flow control and/or to enable one or both of the lines to be selectively opened and closed. Preferably, at least one of such valves is configured as a check valve, and most preferably, each of the inlet and the outlet flow paths includes therein a check valve for controlling the direction of the fluid flow through the pumping cartridge. A "check valve" as used herein refers to a valve that is constructed and configured to prevent or restrict fluid flow in one direction along a flow path and permit fluid flow along a different fluid flow direction, without, or with substantially less, restriction to fluid flow than along the first direction. While, in some embodiments, the inlet and outlet check valves may be located in the inlet line and outlet line, respectively, at a position remote from the pumping cartridge, in more preferred embodiments, the pumping cartridge contains therein at least a portion of at least one of the outlet check valve and inlet check valves, and, more preferably, includes therein at least a portion of each check valve.

Embodiments of the present invention also provide a variety of check valve configurations preferred for use in the pumping cartridges of the invention. The valves provided according to the invention are generally configured to include a sealing element and a valve seat, with sealing contact between the sealing element and the valve seat defining a closed configuration of the valve. A "valve sealing element" or "sealing component" of a valve refers to the portion of a valve that makes contact with a valve seat and which is primarily responsible for transmitting fluid pressure-generated forces to the valve seat surface for forming a pressure-tight seal. In preferred embodiments, the sealing element of the valve, when in sealing contact with the valve seat with the valve positioned in a closed configuration, forms a seal capable of withstanding a pressure differential of at least about 1000 psi, without substantial leakage therethrough, in more preferred embodiments at least 5000 psi, in other preferred embodiments at least about 8000 psi, in other preferred embodiments at least about 15,000 psi, in other embodiments at least about 20,000 psi, in other embodiments at least about 30,000 psi, and in yet other embodiments at least about 50,000 psi. "Without substantial leakage" or "no substantial leakage" as used in the present context refers to a condition wherein there is essentially no leakage or where the leakage rate is within tolerable limits at desired operating pressures.

Leakage rates that are tolerable will, of course, vary with the particular pumping cartridge configuration and pumping or infusion application being performed; however, typically, during the main stage of operation, after any initial break-in period, leakage rates are preferably less than about 0.5% of an average pumping flow rate of the pumping cartridge in operation, more preferably less than about 0.1%, even more preferably less than about 0.05%, and most preferably less than about 0.02%. Leakage rates during any initial break-in stage of operation of the piston, for example during the first 1,000 strokes or so, can be higher, for example up to about 5% of an average pumping flow rate of the pumping cartridge in operation during this period.

In some preferred embodiments, pumping cartridges provided according to the invention include at least one valve comprising a valve seat and a sealing element, where the sealing element comprises a generally concave occluding surface positioned to face the valve seat, when the valve is assembled in an operative configuration. The structural details of such a configuration are discussed in more detail to follow. The term "concave" as used in the above context refers to the surface having an arch-like configuration that may be curved, partially curved, or formed of a series of interconnected straight or flat segments. In some preferred embodiments of valves having sealing elements comprising concave occluding surfaces, the sealing element is formed of a resilient material, which, in certain embodiments, can be the same resilient material from which the integral piston and/or sealing component of the piston and/or cylinder is formed. Such material can be, as described in more detail below, a polymeric material, preferably a non-elastomeric polymeric material. As discussed previously, in preferred embodiments, the valve of the pumping cartridge is configured as a check valve. In such embodiments, the sealing element described above can form at least a portion of a poppet of the check valve. The poppet, in some embodiments, includes a rigid insert, preferably metallic and preferably positioned in the center of the poppet, which may form a portion of the occluding surface that covers the hole in the valve seat. In this regard, the rigid insert resists extrusion into the hole when under pressure. The term "poppet" as used herein refers, broadly, to an axially moveable portion of a check valve including, carrying or connected to a sealing element of the valve.

In certain embodiments of the invention, particularly in embodiments involving pumping cartridges having an axial configuration, the piston and/or piston rod of the pumping cartridge is configured to include, or at least partially form at least one valve. The phrase "includes, or at least partially forms, a valve" or "including, or at least partially forming, a valve," when used to describe certain pistons and/or piston rods provided according to the invention, refers to configurations wherein one or more components forming the valve are either in contact with or at least partially contained within the piston and/or piston rod, or wherein at least a part of the valve is formed, at least partially, from a surface or component of the piston and/or piston rod. In some such embodiments, as described in more detail below, the piston may be configured as a floating piston that is movable relative to the piston rod, and which includes as part of its structure a secondary sealing component comprising the sealing component of a check valve of the pumping cartridge. As illustrated and described below, such floating piston-formed check valves are most conveniently and preferably configured as inlet check valves of the pumping cartridge, with valves seats for such valves being typically formed from a distal end surface of a piston rod to which the floating piston is coupled. In yet other embodiments, the piston and/or piston rod may include, or at least partially form more than one valve, for example two valves (e.g. both an inlet and an outlet check valve of the pumping cartridge).

The inventive pumping systems, pumping cartridges, and pumping methods will now be described in more detail in the context of several specific embodiments illustrated in the appended figures. It is to be understood that the embodiments described are for illustrative purposes only and that the novel features of the invention, as described in the appended claims can be practiced in other ways or utilized for systems and methods having other configurations, as apparent to those of ordinary skill in the art.

FIGS. 1, 2A-C, and 3 illustrate one embodiment of a pumping cartridge 100 provided according to the invention. Pumping cartridge 100 is configured with a "Y-shaped" fluid flow path. Specifically, the main body portion 102 of pumping cartridge 100 (seen most clearly in FIGS. 2A and 2B) includes therein three bores 104, 106 and 108 having longitudinal axes 110, 112 and 114, respectively, which are each essentially parallel to each other. Bore 104 comprises a cylinder forming pump chamber 114 of pumping cartridge 100. Cylinder 104 is disposed in the proximal part of main body portion 102, while bores 106 and 108 are disposed in distal surface 116 of main body portion 102, with each of their longitudinal axes displaced laterally from longitudinal axis 110 of cylinder 104, such that the overall configuration is similar to a "Y." Bores 106 and 108 are in fluid communication with pump chamber 114 via apertures 118 and 120 formed in main body portion 102, respectively. A "pump chamber" as used herein in the context of the pumping cartridges provided according to the invention, refers to a cylinder (preferably a circular cylinder, however, in other embodiments, the cylinder may have essentially any perimetric shape), or portion thereof, in which a piston and/or piston rod slides or reciprocates when the pumping cartridge is in operation.

Main body portion 102 of pumping cartridge 100 can be constructed of a wide variety of materials, as would be apparent to those of ordinary skill in the art. In preferred embodiments, the main body portion 102 is formed of a sterilizable, biologically compatible material that is suitable for use for medical/surgical pumping applications. In the illustrated embodiment, main body portion 102 is constructed of a surgical-grade stainless steel, which has been machined to form the various bores, grooves, and features illustrated in the figures. In the illustrated embodiment, main body portion 102 is constructed of materials and with dimensions and wall thicknesses selected to enable the pumping cartridge to withstand the maximum contemplated operating pressures of the pumping cartridge (e.g., at least 1000 psig) without the need for additional support to prevent mechanical failure of main body portion 102. However, in some embodiments, especially those where low cost and ease of manufacture are particularly critical, main body portion 102 can be constructed of materials and/or with dimensions and thicknesses, which render the main body portion incapable of withstanding contemplated operating pressures without additional means of external support. As will be explained in greater detail below in the context of FIGS. 6A and 6B, the invention also provides a support nest structure, for forming part of a reusable pump drive unit, for coupling to the pumping cartridge, which support nest structure can be configured to mate with and support the main body portion such that it is able to withstand much higher operating pressures, without failure, when supported by the support nest structure than the main body portion would be able to withstand without such support. In such embodiments, main body portion 102 can be constructed, for example, from a variety of lightweight inexpensive materials, for example, polymeric materials. For example, in some embodiments, main body portion 102 can be constructed, via injection molding, of a variety of well-known rigid or semi-rigid plastic materials. In preferred embodiments, involving pumping cartridge main body portions constructed of a non operating pressure-supporting polymeric materials, the cylinder in which the piston reciprocates, comprises a thin-walled section of metal tubing, for example, stainless steel tubing, which is press fit or molded into the main body portion of the pumping cartridge.

Pumping cartridge 100 also includes a piston 122 constructed and arranged for sliding motion and reciprocation within cylinder 104. Piston 122 is coupled to piston rod 124, which, in turn, is couplable to a mechanical pump drive unit (illustrated in FIGS. 6A-6B) via mechanical pump drive coupling region 126. The specific structure of piston 122 and piston rod 124 is described in more detail below in the context of FIG. 3. Piston 122, in the illustrated embodiment, comprises a one-piece, cap-like structure molded over distal end 128 of piston rod 124. As will be described in more detail below in the context of FIGS. 3 and 4A-B, the particular configuration and materials of construction of piston 122 can be varied within the scope of the invention.

As illustrated in FIG. 1, piston 122 comprises an integrally formed, preferably by injection molding, polymeric component including, as part of its structure, a circumferential sealing component 130, which includes a flared sealing flange portion 132 in contact with inner surface 134 of cylinder 104 during operation. In the embodiment illustrated, piston 122 is injection molded directly onto distal end 128 of piston rod 124, which includes a securing flange 136 and securing notch 138, around and into which piston 122 is molded, thereby securing piston 122 to piston rod 124 during operation. It should be understood that, in other embodiments, the piston can be secured to the piston rod in a variety of different ways. For example, in other embodiments, the piston may be secured to the piston rod via, for example, chemical and/or thermal bonding or welding, via use of various fasteners, for example, rivets, screws, barbs, pins, etc., as would be apparent to those of ordinary skill in the art, or, alternatively, the piston rod and piston can comprise a single integral component constructed of the same material. Also, the piston or the piston rod, or both, may be threaded to facilitate coupling and/or attachment.

Piston 122 can be formed of a wide variety of materials capable of withstanding the pressures contemplated, such as, for example, a variety of metals, ceramics, plastics, etc. As is described in more detail below in the context of FIGS. 3 and 4C, in preferred embodiments, piston 122 is formed of a non-elastomeric semi-rigid plastic that is dimensionally stable, but displays certain irreversible deformation properties within the range of operating pressures/conditions contemplated. Preferred plastics include crystalline polymers or semi-crystalline polymers, or amorphous polymers having a glass transition temperature higher than the operating temperature of the pumping cartridge. Piston 122 can potentially be constructed from a wide variety of engineering plastics, for example, including, but not limited to polytetrafluorethylene (PTFE), polypropylene, high-density polyethylene, polyvinylchloride, polyamides, polyimides, polyarylimides, polyacetals, polysulfone, polystyrene, mixtures thereof, etc., as apparent to those of ordinary skill in the art. Engineering plastics including fillers may also be used. In particularly preferred embodiments, piston 122 is constructed of plastics having certain desirable mechanical and materials properties, discussed below, which enable the piston to exhibit desirable deformation, sealing, and wear characteristics. Particularly useful plastics having these characteristics, which comprise a particularly preferred embodiment for use in forming piston 122, and the other pistons described below for other embodiments of the invention, are nylon 6-6, acetal polymers, for example, polyoxymethylene (DELRIN™), and polyimides.

In preferred embodiments, piston 122 is dimensioned and configured, as discussed below, such that, during at least a part of the operation of pumping cartridge 100, a seal formed between flared sealing flange 132 of piston 122 and inner surface 134 of the cylinder is able to withstand a pressure differential across the seal of at least about 1,000 psi without substantial leakage of fluid therethrough, more preferably at least about 5,000 psi, more preferably at least about 8,000 psi, even more preferably at least about 15,000 psi, in other embodiments at least about 20,000 psi, in other embodiments at least about 30,000 psi, and in yet other embodiments at least about 50,000 psi. As described above, in the illustrated embodiment, and preferably, piston 122 comprises an integrally formed one-piece component in which sealing component 130 and a main body portion 140 of the piston comprise a single piece element. However, in other embodiments, the sealing component and main body of the piston can be non-integrally formed, but, instead, the sealing component could comprise a separate or separable element connected to the piston, either rigidly (e.g., by gluing, welding, bonding, etc.), or non-rigidly and/or movably (e.g., the sealing component could comprise a circumferential flange or ring positioned at least partially within a groove, channel or other seating means within the piston). In preferred embodiments, as illustrated, flared sealing flange 132 of sealing component 130 extends away from main body portion 140 of piston 122 at least axially, and preferably axially, radially, and distally, and is preferably pivotally flexible with respect to the main body portion of the piston.

Piston rod 124 can be constructed of a wide variety of materials, for example, from the materials described above suitable for constructing main body portion 102 of pumping cartridge 100 and/or piston 122. The materials selected should have sufficient strength and durability to enable the piston rod to withstand and transmit the forces applied by a mechanical pump drive unit (not shown) to the piston for pumping fluids at the contemplated operating pressures of the pumping cartridge. In one embodiment, piston rod 124 is constructed of aluminum. In the illustrated embodiment, the mechanical pump drive coupling region 126 of piston rod 124 includes, at its distal end, a circumferential load bearing flange 142, which is configured to bear the majority of, and, preferably, essentially the entire, load applied by the mechanical pump drive unit during a discharge stroke of the pumping cartridge in operation. Region 126 further includes a coupling notch 144, which is configured to mate with a tab, ring, or other quick connect mechanism of the mechanical pump drive unit, in order to allow easy snap-in coupling of the piston rod and a reciprocating plunger of a mechanical pump drive unit (not shown). It should be understood that the shape and coupling mechanism selected for coupling piston rod 124 to a reciprocating plunger of the mechanical pump drive unit is not particularly critical and may, in other embodiments, take on an extremely wide variety of forms and configurations, as would be apparent to those of ordinary skill in the art. For example, instead of including the quick-connect coupling means illustrated, the piston rod could be connected to a reciprocating plunger via a more permanent connection, such as a connection comprising a threaded coupling, nuts and bolts coupling, etc., or, alternatively, the piston rod could be permanently connected to the reciprocating plunger, for example, by welding, etc. In yet another embodiment, the piston rod and the reciprocating plunger of the mechanical pump drive unit may comprise a single, integral element, which element is removable from the pumping cartridge and, in some embodiments, the piston, and which comprises part of the reusable system (e.g. see FIGS. 7, 8A, and 8B).

Pumping cartridge 100 further includes an optional flexible skirt 146 provided to prevent material from the external environment from contaminating pump chamber 114 and the fluid flow paths within the pumping cartridge via entry into cylinder 104 through the moving seal created between the piston, or in some embodiments the piston rod, and inner surface 134 of the cylinder. Provision of such a flexible skirt or "bioseal" is especially desirable when the pumping cartridge is utilized for medical or surgical pumping applications. As illustrated in FIG. 1, flexible skirt 146 includes a first sealing ring 148 positioned in sealing contact with notch 150 of piston rod 124. In the illustrated embodiment, sealing ring 148 of flexible skirt 146 is sealed within notch 150 via an adhesive seal 152. In other embodiments, sealing ring 148 could be positioned in sealing contact with a portion of the piston rod proximal to the cylinder of the pumping cartridge via any of a wide variety of well-known sealing means known to those of ordinary skill in the art. At its proximal end, flexible skirt 146 includes a flange 154 positioned within groove 156 of main body portion 102 of pumping cartridge 100. Flange 154 is compressed into sealing contact with notch 156 upon coupling with a complementarily shaped support nest of the reusable mechanical pump drive (see FIGS. 6A and 6B). As illustrated, an O-ring 158 is provided, which can be integral with flange 154 or separate, to further increase the compression forces tending to seal flange 154 within notch 156 of main body portion 102 of pumping cartridge 100. Flexible skirt 146, providing a static bioseal to prevent contamination of pump chamber 114, can be constructed of a wide variety of flexible and/or elastomeric materials, for example of a variety of natural rubbers and synthetic polymers, as would be apparent to those of ordinary skill in the art. In one preferred embodiment, the flexible skirt is constructed of an injection molded thermoplastic elastomer, such as KRATON®G polymer (e.g. DYNAFLEX®G2712 with a Shore A hardness of about 43).

Preferred pumping cartridges, according to the invention, when assembled and configured for operation, comprise a main body portion of the pumping cartridge having an outer surface including at least one bore therein that contains at least a portion of a body portion of a valve that is in fluid communication with the pump chamber. A "body portion of a valve," as used herein, refers to a support structure of the valve that contains or at least partially surrounds at least a portion of the moving parts of the valve, or that provides a valve seat of the valve, or which acts to positions and directly supports one or more of the moving parts of the valve within a bore of the pumping cartridge.

In the embodiment illustrated in FIG. 1, bores 106 and 108 house inlet check valve 159 and outlet check valve 160, respectively. Inlet check valve 159 includes body portion 162 of the valve, a portion of which is positioned within port 106. Body portion 162 of inlet check valve 159 comprises a portion of inlet fitting 164, which is connected to inlet tubing 166 via a low pressure tubing connection 168. Similarly, outlet check valve 160 includes a body portion 170 comprising a portion of outlet fitting 172, which is connected to high pressure outlet line 174 via a high pressure tubing connection 176 including a ferrule 178. As illustrated, both inlet fitting 164 and outlet fitting 172 form a pressure-tight seal with the inner surface of the bores in which they are inserted via inclusion of an O-ring (180, 182 for the inlet and outlet fitting, respectively). Because the seals, especially the seal provided on outlet fitting 172, are potentially subjected to high pressure differentials, for example outlet pressure differentials exceeding 1,000 psi for the outlet seal, in preferred embodiments, the O-rings (180, 182) are oversized and are differently shaped than the grooves 184, 185 in the inlet fitting 164 and outlet fitting 172, respectively, in which they are inserted and, in addition, have a different unstressed cross-sectional shape than that of the grooves (e.g., in the illustrated embodiments, the O-rings have a circular cross-sectional shape, whereas the grooves have a square or rectangular cross-sectional shape), such that when compressed into the grooves, the O-rings display an effective elastic modulus approaching that of hard plastic or soft metal, thus providing an effective high-pressure seal. Such high-pressure O-ring seals are described in greater detail in the applicants' U.S. Pat. Nos. 5,713,878 and 6,216,573, both incorporated herein by reference.

Inlet fitting 164 and outlet fitting 172 can be secured within main body portion 102 of pumping cartridge 100 by a variety of means as would be apparent to those of ordinary skill in the art. In some embodiments, for example, the fittings may be secured via threaded connection, welded in place, press fit, etc. In the illustrated embodiment, however, as described in more detail below in the context of FIGS. 6A-B, the inlet and outlet fittings are not rigidly or permanently attached to the main body portion 102 of pumping cartridge 100, but rather, each is shaped to include a shoulder flange 185, which, upon coupling of the pumping cartridge with the support nest structure illustrated in FIGS. 6A-B, becomes pressed against the distal surface 116 of main body portion 102, thus preventing the fittings from becoming extruded by the fluid pressure in pump chamber 114 and creating and maintaining a pressure-tight seal between the fittings and the inner surface of the bore in which they are inserted. Accordingly, it should be noted that prior to coupling of pumping cartridge 100 with the support nest structure, inlet check valve 159 and outlet check valve 160 are, in this embodiment, incapable of supporting the typical operating pressures generated by the pumping cartridge during operation.

Inlet check valve 159 and outlet check valve 160 each further include a poppet 186 providing the sealing element 188 of each of the valves. Poppet 186 and sealing element 188 are described in much greater detail below in the context of FIGS. 5A-C. Inlet check valve 159 and outlet check valve 160 are similar in design and configuration, except that the poppets and sealing elements are reversed in their configuration such that inlet check valve 159 permits flow in the direction of arrow 190 but prevents flow in a direction opposite arrow 190. Conversely, outlet check valve 160 is configured to permit fluid flow in a direction of arrow 192, but prevent fluid flow in a direction opposite arrow 192. Inlet check valve 159 includes a valve seat 194 formed from the distal surface of body portion 162 of the valve. Poppet 186 of inlet check valve 159 is normally biased by biasing element 196 so that its sealing element 188 is pressed in sealing contact against inlet valve seat 194. Similarly, outlet check valve 160 includes an outlet valve seat 198 comprising a proximal surface of bore 108 that further includes a poppet 186 and a biasing element 196 configured to force sealing element 188 of the poppet against the outlet valve seat. Sealing elements 188 of poppets 186 each include an occluding surface 200 positioned adjacent to and facing the valve seats. Sealing elements 188 also include a circumferential sealing lip 202 (seen more clearly in FIGS. 5A-C) projecting from a portion of the occluding surface towards the valve seat. A "circumferential sealing lip," as used herein, refers to a surface of a sealing element of a valve circumscribing the perimeter of a planar area, which area completely overlays a region of a valve seat forming an aperture(s), when the sealing element is in contact with the valve seat. Biasing elements 196, as illustrated, are coil springs; however, as would be apparent to those of ordinary skill in the art, a wide variety of other biasing elements capable of performing essentially the same function could, alternatively, be used in place of the illustrated coil springs.

Sealing elements 188, in preferred embodiments, when positioned in sealing contact with a valve seat in a closed configuration, form a seal that is capable of withstanding a pressure differential of at least about 1,000 psi without substantial fluid leakage therethrough, in more preferred embodiments at least about 5,000 psi, in more preferred embodiments at least about 8,000 psi, in other preferred embodiments at least about 15,000 psi, in other embodiments at least about 20,000 psi, in other embodiments at least about 30,000 psi, and in yet other embodiments at least about 50,000 psi.

Figure 2A:
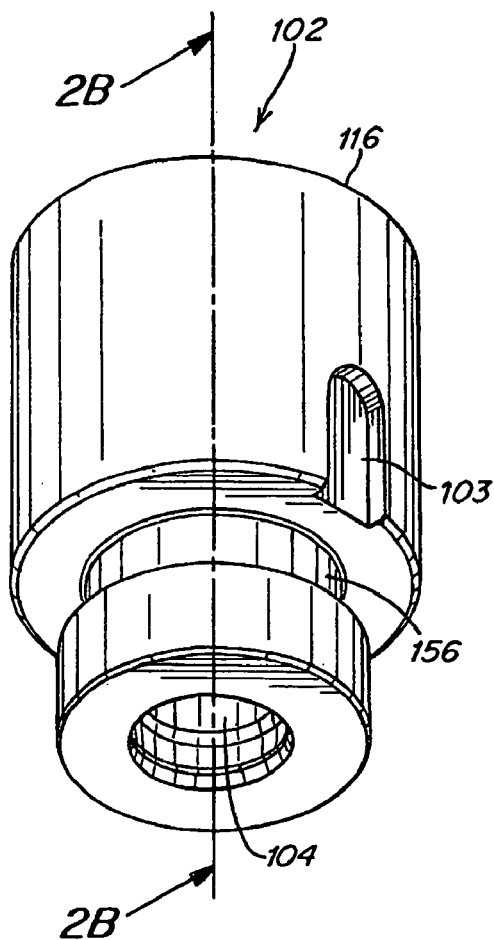
FIG. 2A is a schematic, perspective illustration of the main body portion of the pumping cartridge of FIG. 1.
Figure 2B:
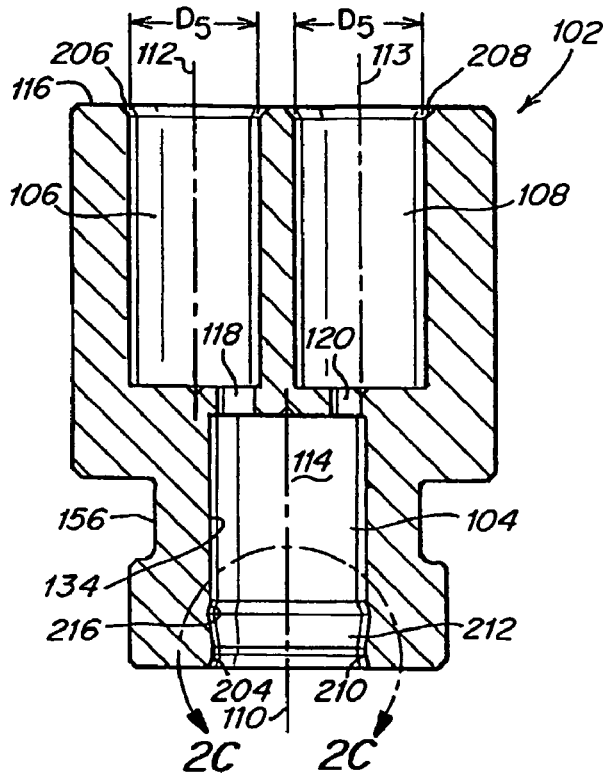
FIG. 2B is a cross-sectional illustration of the main body of the pumping cartridge shown in FIG. 2A along line B-B.
Figure 2C:
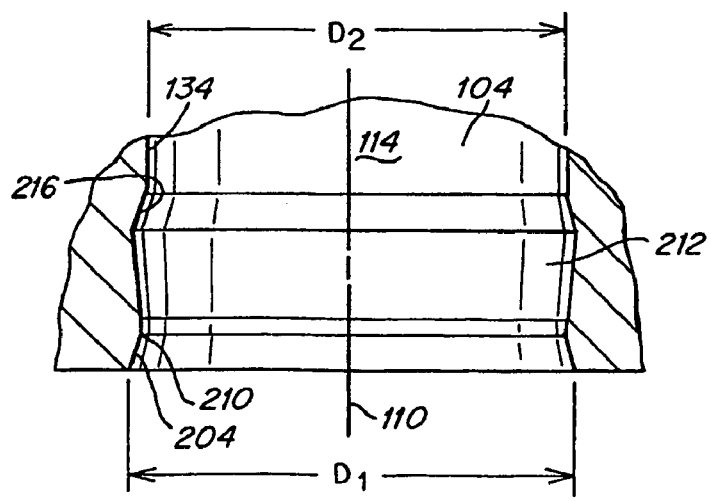
FIG. 2C is a cross-sectional, detailed illustration of section C of the pumping cartridge main body illustrated in FIG. 2B.

Referring now to FIGS. 2A-C, FIG. 2A is a three-dimensional perspective view of main body portion 102 of pumping cartridge 100, shown without the inlet and outlet check valves, flexible skirt, and the piston/piston rod assembly for clarity. FIG. 2A shows most clearly the shape and contour of the main body portion 102 of pumping cartridge 100. As described in more detail below in the context of FIGS. 6A-B, in preferred embodiments, the support nest structure provided by the mechanical pump drive unit and the pumping cartridge are shaped and configured so that they can be coupled in operative association when the pumping cartridge is installed in only a single, predetermined orientation. As described below, main body portion 102 includes on a peripheral surface thereof an orientation notch 203 that is shaped and positioned to mate with the support nest structure only when the pumping cartridge is oriented in a single, predetermined operative configuration.

FIGS. 2B-C illustrate main body portion 102 of FIG. 2A in cross-section. As shown in FIG. 2B, each of bores 104, 106 and 108 preferably include beveled inner surface regions 204, 206 and 208, respectively, which ease the insertion of components (i.e., piston 122, inlet fitting 170 and outlet fitting 172) upon assembly. Beveled inner surface 204 of cylinder 104 is located at a proximal end of the cylinder, into which end piston 122 is inserted upon assembly of the pumping cartridge. The maximum inner diameter $D_1$ of the beveled inner surface is sized to exceed the maximum outer diameter of piston 122, when the piston is in a relaxed configuration prior to insertion of the piston into the cylinder for the first time. The minimum inner diameter of the beveled inner surface at 210 (seen most clearly in FIG. 2C) preferably does not exceed the maximum outer diameter of the piston, when the piston is in a relaxed configuration prior to insertion in the cylinder for the first time, and, most preferably, is essentially the same diameter $D_2$ as the portion of cylinder 104 comprising pump chamber 114. As is most clearly illustrated in FIG. 2C, cylinder 104, at its proximal end, in preferred embodiments, includes a piston storage region 212 positioned distal to beveled inner surface 204 and proximal to pump chamber 114 of the cylinder.

A "piston storage region" as used herein refers to a region of the cylinder in which the piston is inserted and carried during shipment and storage, but prior to use of the pumping cartridge for pumping. In the preferred embodiment illustrated, piston storage region 212 comprises a circumferential indent in cylinder 104 having a shape and contour complementary to the shape and contour of an outer, cylinder wall-facing surface (e.g., surface 214) of the piston and having a maximum inner diameter (equal to $D_1$, as illustrated) exceeding the maximum outer diameter of the piston, when the piston is in a relaxed configuration prior to insertion in the cylinder for the first time. The piston storage region illustrated can serve two functions. First, the storage region can accommodate the flared sealing flange of the piston without exerting distorting pressure on it. This can allow the piston to be co-sterilized with the rest of the assembly and left in place during shipment without putting pressure on the flared sealing flange that might, over time, distort it. Furthermore, the narrowing of the piston storage region (in beveled region 216) to the inner diameter of the pump chamber provides some resistance to the initial entry of the piston into the pump chamber. This resistance can allow the piston rod mechanical pump drive coupling region (e.g., region 126 of piston rod 124) to be pushed into a reciprocating plunger of the mechanical pump drive unit and latch, without the need for special tools or handling to effect assembly.

Figure 3:
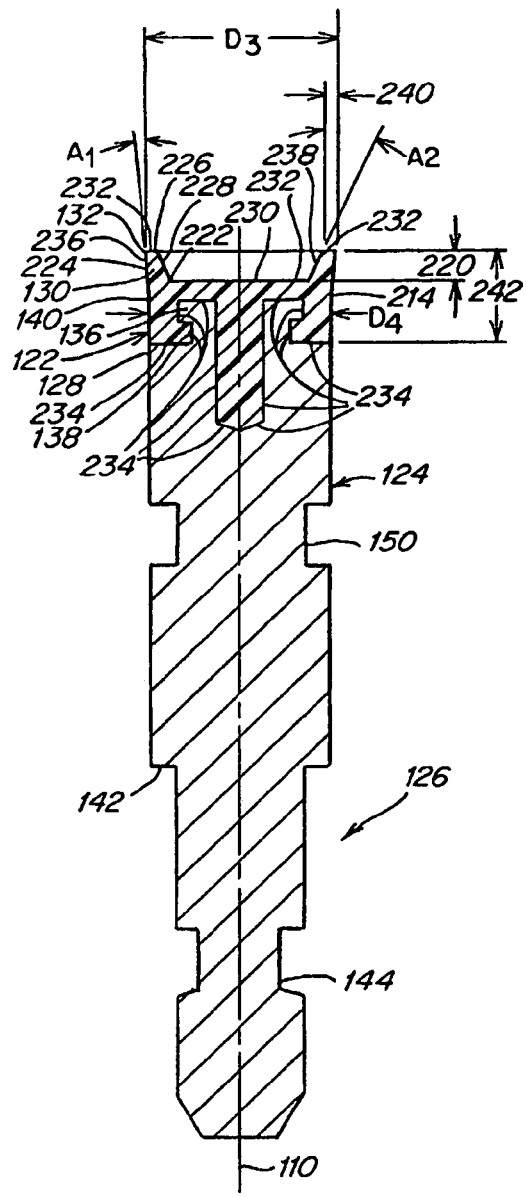
FIG. 3 is an enlarged, cross-sectional illustration of the piston/piston rod assembly of the pumping cartridge of FIG. 1.

Referring now to FIGS. 3 and 2B-C, some preferred dimensions and configurations of the pistons provided according to the invention are described. At the outset, it should be emphasized that functional or optimal dimensions and configurations for the piston are variable depending upon, for example, the materials from which the piston is formed, the inner diameter of the pump chamber, the desired operating pressure range, the degree of fluid leakage tolerable for the particular application, and the duration of operation/wear rate of the piston that is desirable. Accordingly, the selection of particular values for the various dimensions and features discussed for acceptable or optimal performance should be determined via routine screening tests involving the fabrication and testing of cartridges using pistons having various materials properties, configurations, dimensions, etc. under actual desired operating conditions to determine, for example, maximum pressures that can be generated, leakage rates, time to failure, etc for a specific piston design. Similar considerations are also relevant to the design and fabrication of sealing components configured to be positioned on a cylinder wall for embodiments employing such sealing components. Such screening tests involve only routine experimentation and optimization, which can be readily performed by those of ordinary skill in the art.

The particular dimensions and configurations discussed below are given in reference to a pumping cartridge having a pump chamber, in which the piston reciprocates, having a nominal internal diameter (I.D.) of about 0.375 inch. FIG. 3 illustrates a preferred embodiment in which the flared sealing flange portion 132 of piston 122 is integrally formed with the main body portion 140 of the piston. "Integrally formed" as used herein refers to the sealing flange portion and main body being a single, unitary structure, with each constructed of the same material. A "main body portion of the piston" refers to a centrally disposed structural component of the piston to which the sealing component (e.g., 130) is connected. As discussed previously in the context of FIG. 1, in preferred embodiments, piston 122 and flared sealing flange 132 are formed of semi-rigid, non-elastomeric polymeric materials. It has been discovered, within the context of the present invention, that preferred materials for use in forming piston 122, which provide desirable deformation properties, possess several specific materials property falling within preferred ranges, as discussed immediately below.

The sealing flange portion of the piston, and in preferred embodiments the entire piston, is preferably constructed of non-elastomeric polymeric materials exhibiting certain ranges of materials properties. The tensile strength is preferred to fall in a range of between about 3,000 psi (about 21 MPa) to about 50,000 psi (about 350 MPa), more preferably between about 8,000 psi to about 35,000 psi (about 56 MPa to 245 MPa), and even more preferably between about 9,000 to about 20,000 psi (about 63 MPa to 140 MPa). The flexural modulus is preferably in the range of between about 100,000 psi to about 700,000 psi (about 700 MPa to 4900 MPa), more preferably in the range of between about 200,000 psi to about 550,000 psi (about 1400 MPa to 3850 MPa), and even more preferably in the range of between about 350,000 psi to about 450,000 psi (about 2450 MPa to 3150 Mpa). In addition, the material should have good abrasion resistance. The above properties should be present when the material is at about ambient temperature (e.g. 68-77 degrees F., 20-25 degrees C.), or whatever is the desired operating temperature of the piston. In general, the materials available for manufacture of the sealing component of the invention (i.e., those associated with the piston, cylinder, and/or valve poppet) include at least the materials discussed above for manufacture of the piston and its sealing component. The particular selection depends on structural and operational details of the particular system, including operating pressures and the relative size of the piston and/or sealing component(s) and the cylinder. Optional materials for a particular application may be readily selected from the list of candidate materials provided or other suitable materials by routine screening tests or optimization, as described previously and below. It is known that the apparent materials properties of polymeric materials can differ markedly from batch to batch/formulation to formulation, depending, for example, on the details of processing, and hence the above ranges of materials properties are to be taken as a guide to selection or formulation of potentially suitable materials. The actual suitability of a particular polymeric material formulation should be determined/confirmed by analytical testing/experimentation. Some polyamides (e.g. nylon 6,6) and acetals (e.g., DELRIN®) have been found to be suitable for use in creating formulations with the above-mentioned properties, and these may be used as model materials for guiding selection of other candidates for materials suitable or preferred for this use.

In the embodiment illustrated in FIG. 3, piston 122 includes a sealing component 130 shaped to include a flared sealing flange portion 132 that is constructed and arranged to make contact with an inner surface 134 of cylinder 104 during operation. In preferred embodiments, flared sealing flange portion 132 has a predefined length 220 and extends away from main body portion 140 of the piston so as to form a cantilevered circumferential flange thereon. In the illustrated embodiment, predefined length 220 of flange 132 is preferably between about 0.01 inch and about 0.2 inch, more preferably between about 0.02 inch and about 0.1 inch, and in some preferred embodiments is about 0.06 inch to about 0.08 inch. A "cantilevered circumferential flange," as used herein in the context of the piston/cylinder sealing components provided according to the invention, refers to a flange that circumscribes the entire outer perimeter of the main body portion of the piston, or the cylinder-engaging main body portion of a sealing component positioned on a cylinder (e.g., see FIGS. 17A-D) and is attached (e.g., at portion 222 of the main body of the piston) to the main body portion along one of its sides, while having at least two additional sides or faces (e.g., surfaces 224, 226 and 228) that are not attached to, or integral with, the main body portion of the piston or sealing component (e.g., the flange can have a triangular cross-sectional shape or a trapezoidal or rectangular cross-sectional shape).

In one preferred embodiment illustrated, flared sealing flange portion 132 of the piston extends axially away from portion 222 of the main body of the piston to which the flared sealing flange is attached, and is constructed and arranged to make contact with inner surface 134 of cylinder 104, thereby creating a seal between the sealing flange portion and the inner surface of the cylinder able to withstand desired operating pressure differentials (e.g., of at least about 1000 psi) without substantial leakage of fluid therethrough during operation of the pumping cartridge. As used herein, a flared sealing flange portion which "extends axially away" from a portion, to which it is attached of a main body portion of the piston or of a cylinder-engaging main body portion of a sealing component positioned on a pump cartridge cylinder refers to the distal-most and/or proximal-most surface of sealing flange portion being axially displaced from the point of attachment to such main body portion. Also in preferred embodiments, the flared sealing flange portion of the sealing component is configured to extend radially away from the portion, to which it is attached, of the main body portion of the piston/cylinder-engaging main body portion. A flared sealing flange portion of the piston which "extends radially away from" the portion, to which it is attached, of the main body portion of the piston, as used herein refers to the flared sealing flange portion having a largest outer diameter that exceeds the largest outer diameter of the main body portion of the piston. Analogously, a flared sealing flange portion of a sealing component positioned on a pump chamber cylinder which "extends radially inward of the cylinder-engaging main body portion", as used herein refers to the flared sealing flange portion having a smallest inner diameter that is less than the smallest inner diameter of the cylinder-engaging main body portion (see e.g., FIGS. 17A-B). In some preferred embodiments, as illustrated, the flared sealing flange portion also extends distally of a distal most portion 230 of the main body portion of the piston or of a cylinder-engaging portion of a sealing component positioned on a pumping chamber cylinder.

In some preferred embodiments of pistons provided according to the invention, for example as illustrated in FIG. 3, the piston is shaped and positioned within the cylinder, when assembled (see FIG. 1) so that all fluid contacting surfaces that are oriented essentially perpendicular to the longitudinal axis of the cylinder are directly supported by the piston rod. For embodiments where all such surfaces are not directly supported by the piston rod, for example as illustrated in FIGS. 12A and 12D-F, it is preferred that each fluid contacting surface that is oriented essentially perpendicular to the longitudinal axis of the cylinder that is not directly supported by the piston rod has minimum cross-sectional thickness exceeding the minimum cross-sectional thickness of the cylinder sealing flange portion of the sealing component of the piston, preferably by at least about a factor of about 2, more preferably by at least about a factor of about 5, and even more preferably by at least about a factor of about 7.

As illustrated in FIG. 3, piston 122 includes a variety of fluid contacting surfaces 232 that are oriented essentially perpendicular to longitudinal axis 110 of cylinder 104, when the piston assembly is installed in an operative configuration with the pumping cartridge, as illustrated in FIG. 1. Surfaces of the piston are "directly supported" by the piston rod when a line drawn through the surface in a direction essentially parallel to the longitudinal axis of the piston rod/cylinder directly intersects the piston rod or a solid support member carried by the piston rod. "Directly intersects," as used herein, refers to such line passing from the piston to the rod and/or support member without first passing through any intermediate, non-supportive layers, void spaces, etc. In the embodiment illustrated in FIG. 3, all of fluid contacting surfaces 232 that are oriented essentially perpendicular to longitudinal axis 110 are "directly supported" by piston rod 124.

In some preferred embodiments, as illustrated in FIG. 3, all inner, piston rod-facing surfaces of the piston are shaped and arranged such that upon coupling of the piston to the piston rod, essentially all of the such surfaces of the piston are in direct contact with the piston rod or a securing member that is "carried by" the piston rod. In other words, referring to FIG. 3, inner piston rod facing surfaces 234 of piston 122 are each in direct contact with piston rod 124. "Inner, piston rod-facing surfaces" of the piston as used herein refers to non-fluid-wetted surfaces of the piston that are in contact with the surface of the piston rod or a support member carried thereby. "Carried by" as used in the above context refers to such support member being in direct contact with the piston rod or in contact with one or more members at least one of which is in direct contact with the piston rod (e.g., in contact with one of a series of spacers at least one of which is in direct contact with the piston rod).

As discussed above in the context of FIG. 1, piston 122 can be coupled to piston rod 124 via a wide variety of coupling means. As illustrated in FIG. 3, piston 122 is over molded onto the distal end of piston rod 124. Alternative means for coupling the piston to the piston rod, for embodiments wherein the piston is not integrally formed with the piston rod, include, but are not limited to, press-fitting or snap-fitting of the piston onto the end of the piston rod, attachment of the piston to the piston rod by means of screws, pins, rivets, etc., use of an interference fit between, for example, a barb and a hole; and, potentially, a wide variety of other coupling means that would be apparent to those of ordinary skill in the art.

Preferably, the sealing flange portion 132 of the piston 122 has a maximum outer diameter $D_3$ that is large enough to enable at least a portion of the sealing flange to be in essentially continuous contact with inner surface 134 of pump chamber 114 during reciprocation of the piston. This arrangement can be accomplished by forming the sealing flange portion 132 so that maximum outer diameter $D_3$, when the sealing flange is in a relaxed, unstressed configuration (i.e., prior to insertion into the cylinder upon assembly of the pumping cartridge) exceeds the inner diameter $D_2$ (see FIGS. 2B-C) of pump chamber 114. Because flared sealing flange portion 132 is pivotally flexible with respect to main body portion 140 of piston 122, upon insertion of the piston into pump chamber 114, the piston will deform such that it has a maximum, fluid-wetted diameter that is essentially equal to inner diameter $D_2$ of pump chamber 114. "When relaxed" or "in an unstressed configuration" or "unstressed" or "relaxed configuration" or the like, as used herein to describe a condition of various components of the invention (e.g. the flared sealing flange of the piston, the flared sealing flange of the cylinder-positioned sealing components, valve sealing elements, proximal sealing flanges of floating pistons, etc.) refers to such components as configured without forces applied to the components tending to reduce the maximum outer diameter or increase the minimum inner diameter in the case of cylinder-positioned sealing components, of the components, or otherwise distort their configuration and/or dimensions. A "maximum, fluid-wetted diameter" of the piston, as used herein, refers to the maximum diameter of all distally-facing fluid-wetted surfaces of the piston as projected onto a plane essentially perpendicular to the longitudinal axis of the cylinder.

Also, in preferred embodiments, sealing flange portion 132 of piston 122 has a maximum outer diameter $D_3$ that exceeds the maximum outer diameter $D_4$ of main body portion 140 of the piston. In addition, the maximum outer diameter $D_4$ of the main body portion 140 of the piston is less than the inner diameter $D_2$ of pump chamber 114. In preferred embodiments, the sealing flange portion 132 of the piston 122 has a maximum outer diameter $D_3$, when in a relaxed configuration prior to insertion into the cylinder upon assembly of the pumping cartridge, that exceeds the maximum outer diameter $D_4$ of the main body 140 of the piston by at least about 1%, in other preferred embodiments by at least about 3%, in other preferred embodiments by at least about 5%, in other preferred embodiments by at least about 10%, and in one preferred embodiment by about 6%. The particular preferred excess diameter depends on the material, operating pressure, the intended lifespan of the piston, and other engineering parameters. Also, in preferred embodiments, pump chamber 114 has an inner diameter $D_2$ that exceeds the maximum outer diameter $D_4$ of the main body 140 of the piston 122, but is no greater than, and in some embodiments is less than, the maximum outer diameter $D_3$ of the flared sealing flange portion 132 of the piston, when it is in a relaxed configuration prior to insertion into the cylinder upon assembly of the pumping cartridge. Pump chamber diameter $D_2$ can, in some embodiments, be essentially the same as the maximum outer diameter $D_3$ of the flared sealing flange portion, but is typically less by at least about 0.5%, in other preferred embodiments by at least about 1%, in other preferred embodiments by at least about 1.5%, in other preferred embodiments by at least about 2%, in other embodiments by at least about 3%, and in yet other embodiments by at least about 4% or greater.

In preferred embodiments, the diameter of the main body portion of the piston is less than the inner diameter of the cylinder. For example, in a cylinder having an inner diameter of 0.375 inch, the clearance between the main body portion of the cylinder and the inner surface of the cylinder is at least about 0.002 inch, or about 1%. Depending on the particulars of the system, preferred clearances may be larger, such as 1.5%, 2%, 2.5% or 3% or more.

In preferred embodiments, the flared sealing flange is configured such that a first surface 236 of the flared sealing flange portion adjacent to and facing inner surface 134 of pump chamber 114 forms a first angle $A_1$ with respect to the longitudinal axis 110 of the cylinder and a second, cylinder bore-facing surface 238 of the flared sealing flange portion forms a second angle $A_2$ with respect to the longitudinal axis of the cylinder, where the first angle $A_1$ exceeds 0 degrees, the second angle $A_2$ does not exceed 90 degrees, and the second angle $A_2$ exceeds the first angle $A_1$. In some particularly preferred embodiments, the first angle $A_1$ is between about 1 degree and about 20 degrees, and the second angle $A_2$ is between about 10 degrees and about 90 degrees. In even more preferred embodiments, the first angle $A_1$ is between about 3 degrees and about 12 degrees, and the second angle $A_2$ is between about 15 degrees and about 30 degrees. In some especially preferred embodiments, the first angle $A_1$ is between about 6 degrees and about 8 degrees, and the second angle $A_2$ is between about 20 degrees and about 25 degrees.

Flared sealing flange portion 132 has a minimum cross-sectional thickness 240 selected depending on the size of pump chamber 114 and the operating pressures contemplated for use of the pumping cartridge. Flared sealing flange cross-sectional thickness 240 and the predefined length 220 of flared sealing flange 132 tend to vary approximately linearly with the diameter of pump chamber 114 in which piston 122 reciprocates during operation of the pump cartridge. For a pump chamber having an inner diameter $D_2$ of about 0.375 inch, as previously illustrated, the minimum cross-sectional thickness 240 of flared sealing flange 132, for operating pressures of at least about 1000 psig (66 bar), is preferably at least about 0.005 inch, more preferably between about 0.005 inch and about 0.05 inch, even more preferably between about 0.01 inch and about 0.025 inch, and in one preferred embodiment is about 0.021 inch. In preferred embodiments, the minimum cross-sectional thickness 240 of flared sealing flange 132 is between about 1% and about 15% of the maximum outer diameter $D_3$ of the sealing flange portion of the piston, when it is in a relaxed configuration prior to insertion into the cylinder upon assembly of the pumping cartridge, in other preferred embodiments is between about 2% and about 7%, and in one particularly preferred embodiment is between about 2.5% and about 3% of maximum outer diameter $D_3$.

Also, in preferred embodiments, the maximum axial thickness 242 of piston 122, for the conditions discussed immediately above, is between about 0.04 inch and about 0.32 inch, in other preferred embodiments it is between about 0.08 inch and about 0.25 inch, and in one preferred embodiment is between about 0.10 inch and about 0.16 inch. A "maximum axial thickness" of the piston, as used herein, refers to the maximum dimension of non-piston rod-facing surfaces of the piston measured along the axial direction (i.e. parallel to axis 110). It should be noted that the optimal maximum axial dimension of the piston will tend to vary depending upon the operating pressure of the pumping cartridge for which the piston will be utilized. In general, for higher pressures, the maximum axial thickness should be relatively smaller than for lower pressures to prevent the main body portion of the piston from bulging and expanding excessively during use creating undue resistance to motion and excess wear of the piston during operation.

Figure 4A:
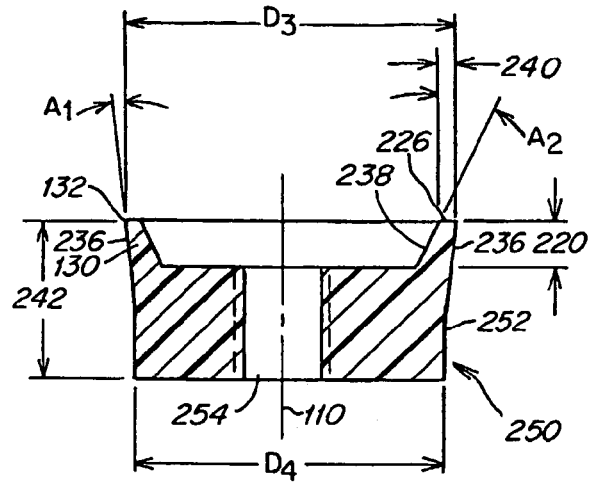
FIG. 4A is a schematic, cross-sectional illustration of one embodiment of a piston.

FIG. 4A shows a cross-sectional view of a piston 250 that is substantially similar in design to piston 122, illustrated previously, except that piston 250 has a main body portion 252 the entirety of which is positioned essentially completely distally of the distal-most portion of a piston rod to which piston 250 is coupled. Thus, piston 250, when installed in an operative configuration onto a piston rod is positioned entirely distally of the piston rod. Main body portion 252 of piston 250 includes a centrally disposed aperture 254, optionally threaded, through which a coupling element can pass, which serves to couple piston 250 to the piston rod. As previously discussed, such coupling element can comprise a wide variety of well-known coupling means, including, for example, a screw, pin, rivet, plug, barb, etc. Dimensions and components that can be substantially similar to those discussed previously for piston 122 are given the same figure labels.

Figure 4B:
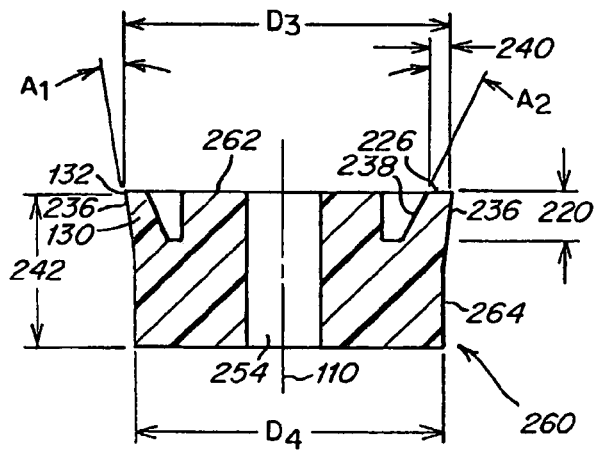
FIG. 4B is a schematic, cross-sectional illustration of another embodiment of a piston.
Figure 4C:
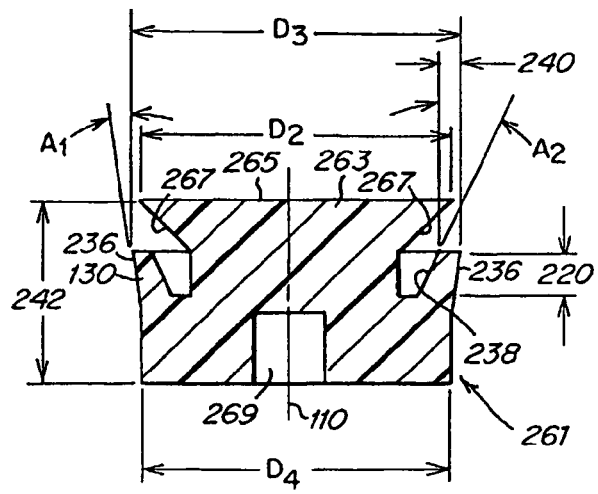
FIG. 4C is a schematic, cross-sectional illustration of yet another embodiment of a piston.

An alternative embodiment to piston 250 illustrated in FIG. 4A is represented by piston 260 shown in FIG. 4B. Piston 260 is substantially similar to previously described piston 250, except that a distal, centrally disposed portion 262 of main body portion 264 is configured to extend distally to a location essentially coplanar with distal most surface 226 of flared sealing flange 132. The configuration of piston 260 can be particularly useful for applications involving small volumetric displacements and/or small pump stroke lengths, since the dead volume of unpumped fluid, when piston 260 is positioned at its end-of-stroke position distal-most in the pump chamber at the end of its delivery stroke is reduced over that of previously illustrated and described pistons 250 and 122.

In a further embodiment (FIG. 4C), the piston 261 can have an additional pressure-distributing element 263 distal to the flared sealing flange 236. The distributor preferably has a flat cylindrical top 265 having a diameter that is nominally equal to the diameter of the cylinder in which the piston reciprocates (e.g. $D_2$, see FIG. 2C). This distal distributor 263 preferably tapers inward at 267, and a sealing component 130, essentially identical to those shown in FIG. 4A or 4B is proximal to the distributor. In the embodiment shown, the piston is configured for coupling to a metal piston carrier, having a central pin (not shown) extending into bore 269 of the piston. The carrier can then be connected to the piston rod. The entire piston can be made of a material of the type used for the other versions of the flanged piston. In operation, it is believed that the pressure distributor rapidly abrades to have a diameter slightly less than that of the cylinder of the pumping cartridge, while the flange (i.e. 236) continues to make sealing contact with the cylinder. Because there can be a significant pressure drop across the distributor, there can be less pressure on the flange resulting in lower amounts of sliding friction such that it does not wear out as rapidly. The flared sealing flange can also potentially, in the present embodiment, sustain/generate a higher pressure for a giving type of material of construction.

In operation, in some embodiments, during an initial "break-in" period, some amount of fluid leakage past the seal formed between the pump chamber cylinder and piston/piston rod by the sealing component may occur. The extent of such leakage in the break-in phase is variable and may be nearly absent. When such a stage is present, it typically will last only for a few seconds, and less typically up to a few minutes. Preferably, the break-in period does not exceed about 1,000 reciprocations of the piston.

During typical operation of pumping cartridges that include piston having sealing components thereon, the piston begins to deform under pressure, any leakage rate during break-in decreases and the maximum pressure able to be generated increases. During a second interval of time (main stage of operation), it is believed that in at least some embodiments, the sealing flange portion and main body portion of the piston will deformed such that at least a portion of the main body portion of the piston proximal to the sealing flange will have radially expanded to make sealing, sliding contact with the inner surface of the pump chamber cylinder. It is believed that when the piston is integrally formed from the above-mentioned preferred non-elastomeric polymeric materials, that this deformation may be essentially irreversible.

Eventually, after a sufficient period of operation, the material comprising the sealing components of the inventive pumping cartridges will wear to the point where the degree of sealing between the piston/piston rod and the inner surface of the cylinder is substantially decreased so that the leakage rate through the seal increases and the maximum pressure able to be generated by the pumping cartridge decreases. Typically, the useful life of the pumping cartridge is defined as the point where the leakage rate through the seal becomes unacceptable and the maximum pressure able to be generated by the pumping cartridge at a particular set of operating conditions becomes reduced beyond a desired level.

The useful lifetime of the pumping cartridge may vary widely, depending on the demands of the particular application. For use in disposable medical devices, the useful lifetime may be as short as about a minute, but is more typically at least about 3 to 10 minutes, preferably at least about 15 to 30 minutes, and, for use in prolonged surgical operations or for repeated use (for example, in debridement), the useful lifetime is preferably at least about one hour of actual pumping time. For other uses of the pump, longer lifetimes, ranging from about 1 hour to 24 or 48 hours or more, can be desirable, and long (days to weeks or months) pump lifetimes can be useful in some cases. Techniques for extending seal life are described below.

Also, in preferred embodiments, the useful life of the pumping cartridge, under operating conditions involving pumped liquid pressures of at least about 1,000 psig, is between about 1 hour and about 24 hours. Also, in preferred embodiments, the piston and/or piston rod is reciprocated within the cylinder at a relatively high rate of speed during operation of the pumping cartridge. In preferred embodiments, the maximum velocity of the piston and/or piston rod during reciprocation is at least about 4 feet per minute, in other embodiments at least about 8 feet per minute, in other embodiments is at least about 12 feet per minute, in other embodiments is at least about 16 feet per minute, in other embodiments is at least about 24 feet per minute, in other embodiments is at least about 32 feet per minute, in other embodiments is at least about 52 feet per minute, in other embodiments is at least about 64 feet per minute, and in yet other embodiments is at least about 128 feet per minute. Some typical examples of pumping cartridges provided according to the invention and configured for medical or surgical pumping applications have velocities falling within the range of about 16 to about 64 feet per minute; however, the particular velocity utilized can vary widely depending, for example, on the diameter of the pump chamber, the stroke length, and the desired delivery rate of fluid. The actual piston/piston rod velocity for a given desired delivery rate can be calculated in a straightforward fashion from the above-mentioned parameters, as is apparent to those of ordinary skill in the art.

Figure 5A:
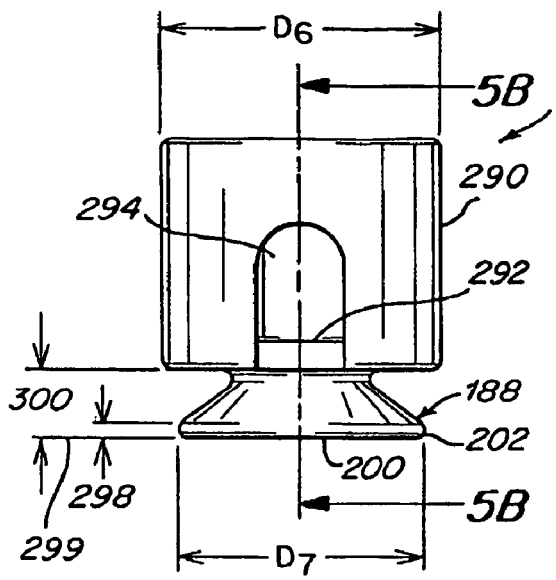
FIG. 5A is an enlarged, schematic illustration of a valve poppet of the pumping cartridge illustrated in FIG. 1.
Figure 5B:
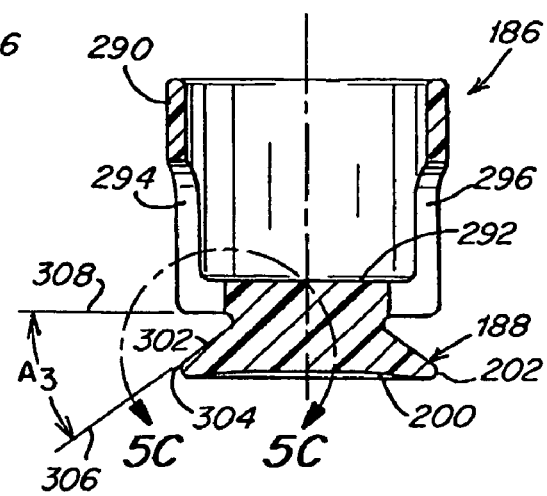
FIG. 5B is a schematic, cross-sectional illustration of the valve poppet of FIG. 5A along line B-B.
Figure 5C:
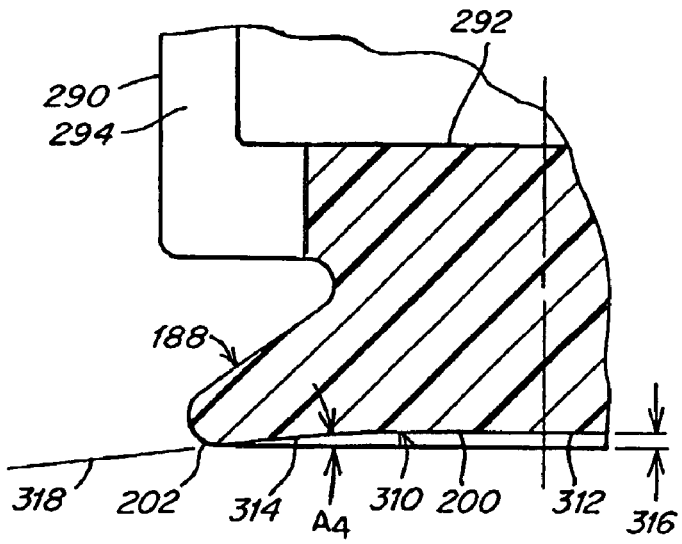
FIG. 5C is a schematic, cross-sectional detail illustration of a portion C of the valve poppet of FIG. 5B.

FIGS. 5A-5C present more detailed views of one embodiment of a valve poppet 186 (previously illustrated in FIG. 1), provided according to one embodiment of the invention. Poppet 186 includes a flared sealing element 188 including an occluding surface 200 positioned to face a valve seat, when a valve incorporating the poppet is assembled in an operative configuration, for example as illustrated previously in FIG. 1. In preferred embodiments, occluding surface 200 is constructed and positioned to make sealing contact with a valve seat, thereby creating a seal, when a valve incorporating the poppet is in a closed configuration, where the seal formed is capable of withstanding a pressure differential of at least about 1,000 psi without substantial leakage therethrough, more preferably at least about 5,000 psi, more preferably at least about 8,000 psi, in other preferred embodiments at least about 15,000 psi, in other embodiments at least about 20,000 psi, in other embodiments at least about 30,000 psi, and in yet other embodiments at least about 50,000 psi.

Preferably, sealing element 188 is formed of a resilient material. Also, in preferred embodiments and as discussed below, the occluding surface of the sealing element is concave in shape and is shaped and dimensioned so that a pressure applied against the sealing element in a direction tending to force the occluding surface against the valve seat deforms the occluding surface so as to increase the maximum circumference of the occluding surface and the area of contact between the occluding surface and the valve seat, thereby creating a mechanical advantage to improve sealing performance. Typically, this occurs via pressure that is applied against the sealing element in a direction tending to force the occluding surface against the valve seat tending to flatten the concave surface against the valve seat. While poppet 186 and/or sealing element 188 can potentially be constructed of a wide variety of materials, for example essentially all those materials previously discussed with respect to forming the pistons and piston/cylinder sealing components provided according to the invention, in preferred embodiments, the sealing element is formed of a polymeric material, preferably by injection molding. In particularly preferred embodiments, the polymeric material is non-elastomeric. In some preferred embodiments, the material can comprise the same material from which the piston and/or piston/cylinder sealing components of the pumping cartridge are formed. Occluding surface 200 of sealing element 188 is preferably configured to include a fluid-impermeable circumferential flange 202 having a configuration and geometry somewhat similar to the flared sealing flange portions 132 of the above-described pistons 122, 250 and 260.

Poppet 186 further comprises an optional body portion 290 to which sealing element 188 and fluid-impermeable circumferential flange or lip 202 are connected so as to extend away therefrom towards the valve seat, when the poppet is assembled in an operative valve configuration. Poppet 186 includes a surface 292 positioned to face away from the valve seat, when the poppet is installed in an operative configuration, and configured to support a biasing element, for example, coil springs 196 shown previously in FIG. 1, which tends to force concave occluding surface 200 against a valve seat. In preferred embodiments, body portion 290 of poppet 186, and sealing element 188, including fluid-impermeable circumferential flange 202, are integrally formed as a single element, for example by injection molding of polymeric material.

Referring also to FIG. 2B, in preferred embodiments, the bore of the pumping cartridge into which the poppet is inserted (e.g. bores 106 and 108 of pumping cartridge 100) have an inner diameter $D_5$, which is slightly greater than the maximum outer diameter $D_6$ of the body portion 290 of poppet 186, in order to provide a close sliding fit and prevent excessive lateral movement within the bore. In the illustrated embodiment, for example, inner diameter $D_5$ is about 0.312 inch, while the maximum outer diameter $D_6$ of body portion 290 of poppet 186 is about 0.298 inch. In this case, $D_6$ is about 95% of $D_5$. Other ranges can be suitable, depending on the details of construction and, in particular, on the length of the poppet. Preferably, $D_6$ is at least about 80% of $D_5$, more preferably $D_6$ is at least about 90% of $D_5$. Also, in preferred embodiments, $D_6$ is no more than about 99% of $D_5$, and, more preferably, $D_6$ is no more than about 98% of $D_5$.

Preferably, to decrease resistance to fluid flow past the poppet when the check valves incorporating the poppet are in an open configuration, the body portion of the poppet includes at least one aperture therethrough defining a fluid flow path. As illustrated, body portion 290 of poppet 186 includes therethrough two apertures 294 and 296, positioned on opposite sides of the body portion and extending through both the side and bottom walls of the body portion of the poppet.

Also, in preferred embodiments, to allow for flattening and expansion of the sealing element within the bore, sealing element 188, when in a relaxed configuration, has a maximum diameter $D_7$, which is less than the maximum outer diameter $D_6$ of body portion 290 of poppet 186. In more preferred embodiments, diameter $D_7$ is between about 60% and about 95% of diameter $D_6$, in even more preferred embodiments is between about 75% and about 90%, and in a particularly preferred embodiment diameter $D_7$ is about 88% of diameter $D_6$.

Fluid-impenetrable circumferential flange portion 202 of sealing element 188 preferably comprises the region having the minimum cross-sectional thickness 298 of the sealing element. Sealing element 188 is also characterized by a maximum dimension, as measured along a direction essentially perpendicular to the plane 299 defined by a tangent plane to occluding surface 200 (i.e., a plane coplanar with the plane of the valve seat upon which the occluding surface impinges, when the poppet is assembled in an operative configuration within the pumping cartridge). This maximum dimension is shown as distance 300 in FIG. 5A. In the particular embodiment illustrated, distance 300 is about 0.072 inch, or about 20% of diameter D7. Subject to the limitations on the value of thickness 300 relative to the thicknesses 298 and 316 (see FIG. 5C), described below, the exact ratio of the distance 300 to diameter D7 is not critical, and can range from about 10% to about 50% or more. The preferred values, which can be found based on the teaching herein via routine testing and optimization, will depend on the modulus/moduli of the polymeric or other material used to make the part, and on the maximum applied force to be resisted.

Preferably, the minimum cross-sectional thickness 298 of sealing element 188 is less than about 25% of distance 300, more preferably less than about 17%. This thickness will also depend on the properties of the material, and on the thickness 300 of sealing element 188 and should be selected via routine testing and optimization.

Referring now to FIG. 5B, sealing element 188 includes a downstream surface 302 positioned facing away from the valve seat when the poppet is assembled in an operative configuration in the pumping cartridge. Downstream surface 302 includes a circumferential periphery 304. Line 306 comprises a line drawn tangent to a point at or near (cumulatively referred to herein as "near") periphery 304 of downstream surface 302, when the sealing element is in a relaxed, unstressed configuration. Angle $A_3$ represents the angle of intersection of tangent line 306 with the valve seat, or, equivalently a line 308 parallel to the valve seat. In preferred embodiments, angle $A_3$ is between about 20 degrees and about 50 degrees, in more preferred embodiments between about 30 degrees and about 40 degrees, and in one preferred embodiment is about 36 degrees.

Referring now to the enlarged, detail cross-sectional view of FIG. 5C, the contour of occluding surface 200 is more readily apparent. Occluding surface 200, as illustrated, comprises a concave surface 310 comprising a combination of three linear segments. Concave surface 310 includes central linear segment 312, having an orientation essentially parallel to plane 299, and two angled linear sections (i.e., section 314 and an equivalent section located on the opposite side of sealing element 188, not shown), which are adjacent to the periphery of fluid-impermeable circumferential flange 202. In alternative embodiments, as opposed to concave surface 310 being formed of a series of interconnected linear segments, the concave surface may instead have at least a portion thereof formed of a curved surface. It should be understood that for embodiments wherein concave surface 310 is curved, that upon forcing occluding surface 200 in the direction of the valve seat, the radius of curvature of the concave surface will tend to increase as the sealing element flattens out upon the valve seat.

In general, as a force is applied to sealing element 188 tending to force the sealing element against the valve seat, for example, a force generated by fluid pressure impinging upon downstream surface 302 of the sealing element, the maximum separation distance between concave surface 310 and the valve seat will tend to decrease. As illustrated, with sealing element 188 in a relaxed, unstressed configuration, the maximum separation distance between the occluding surface and the plane (e.g., plane 299) defined by a valve seat in contact with the occluding surface is shown as distance 316 in FIG. 5C. While distance 316 can potentially be range over a wide range of values, non-zero values are preferred. The particular value that is most preferable will depend, at least in part, on the material properties of the sealing element and the level of applied force during operation and is found by routine testing and optimization, as described previously. In some typical preferred embodiments, separation distance 316 does not exceed about 25% of previously defined dimension 300 of sealing element 188, more preferably does not exceed about 20%, more preferably does not exceed about 15%, more preferably does not exceed about 12%, more preferably does not exceed about 8%, in some embodiments does not exceed about 4%, and in one preferred embodiment is about 8% of distance 300.

In addition, in preferred embodiments, a line drawn tangent to a point near the periphery of concave surface 310 of the sealing element, when the sealing element is in a relaxed, unstressed configuration (e.g., line 318 as shown in FIG. 5c) intersects plane 299/line 308 at an angle $A_4$ of between about 1 degree and about 12 degrees. In more preferred embodiments, $A_4$ is between about 3 degrees and about 9 degrees, and in one preferred embodiment, angle $A_4$ is about 6 degrees.

Figure 5D:
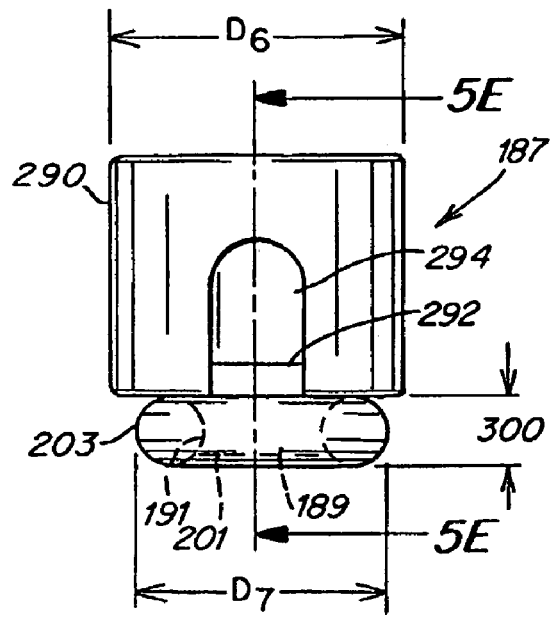
FIG. 5D is an enlarged, schematic illustration of an another embodiment of a valve poppet.
Figure 5E:
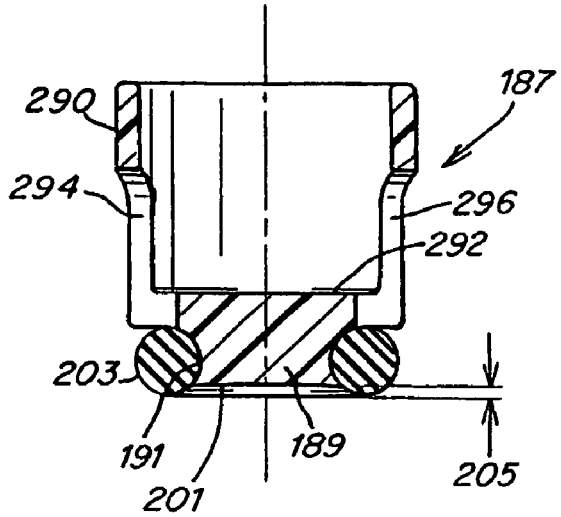
FIG. 5E is a schematic, cross-sectional illustration of the valve poppet of FIG. 5D along line E-E.

An alternative check valve poppet 187, as illustrated in FIGS. 5D and 5E, particularly suited for very high pressures, comprises a main body 290 and a fluid-impermeable circumferential sealing lip 203 comprising an O-ring (shown in phantom for clarity). The poppet is preferably made of a hard, minimally flexible material, such as metal or a high strength engineering plastic. The shape of poppet 187 is generally similar as that of the poppet of FIGS. 5A-C, except that the fluid-impermeable circumferential flange 202 of sealing element 188 previously illustrated is replaced by a sealing element 189, extending from body 290, including a circumferential groove 191 therein, into which is placed the O-ring 203 forming the circumferential sealing lip portion of the sealing element. The remaining inner part of the occluding surface 201 is preferably slightly concave, and the O-ring projects a short distance 205 therefrom. When pressure/force is applied to the sealing element, the O-ring yields and the occluding surface 201 again covers the hole in the valve seat. The use of a stronger, less-flexible material for poppet 187 can allow higher maximum pressures to be sustained by the check valves including the poppet, and use of this design can be especially effective when the operating pressure exceeds 10,000 psig.

Figure 5F:
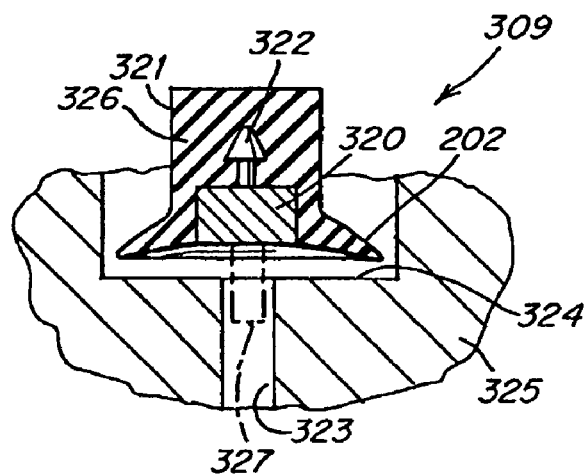
FIG. 5F is a schematic, cross-sectional illustration of another embodiment of a valve poppet.

An alternative embodiment of a high pressure poppet is shown in FIG. 5F. The poppet 290 comprises two subcomponents, a metal core 320 comprising a rigid insert, and a polymeric portion 321 that provides the sealing function. The metal core has a barb 322 or similar device to retain it in the polymeric portion 321. The poppet seats on a hole 323 in a valve seat 324 which is machined or otherwise formed in structural component 325. Although the figure illustrates a preferred embodiment wherein the rigid insert is centrally disposed in the occluding surface of poppet 290, in other embodiments the rigid insert may be otherwise positioned, so long as at least a portion of the rigid insert overlies at least a portion of hole 323 in valve seat 324. Structural component 325 may be a spool, a piston, or a main body portion of a pumping cartridge as illustrated in FIG. 1. In use, a spring, or other biasing element (not shown) at least partially surrounds the upper part 326 of the poppet to provide a closing force. Alternatively, a spring or other biasing element may be attached to an optional tab 327 and may extend downward through the hole 323 to an attachment point elsewhere in the device. A further option, not shown, is to center the poppet on the seat by providing a hollow cylinder in place of tab 327. Such cylinder can be configured and positioned to project through the hole 323, and can be attached to an anchor point in the region beyond the hole by a spring or other biasing element. Under pressure, the resilient portion of the poppet deforms, as described above. However, the rigid insert 320 can help to prevent deformation to the extent that there is poppet deformation into hole 323. Various plastics can be used for the polymeric portion, for example those described above for forming the piston and sealing components. Softer polymers, such as certain nylons, may require O-ring or metal support for support above relatively low pressures.

Figure 6A:
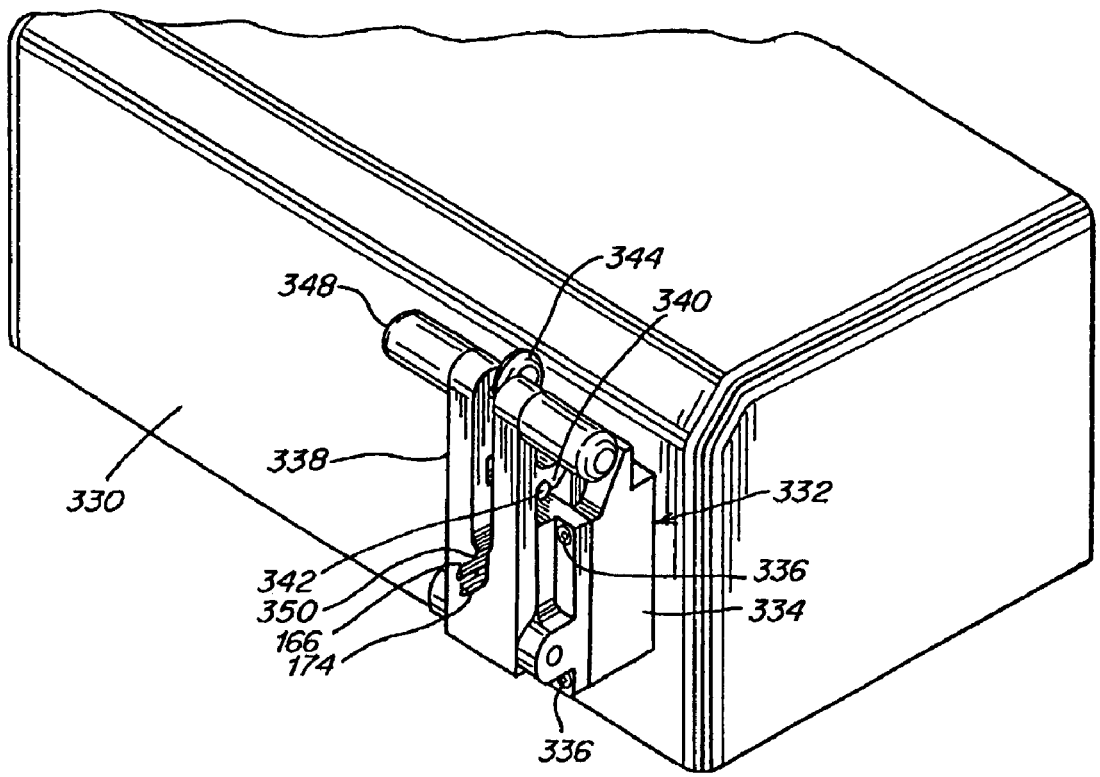
FIG. 6A is a schematic, perspective illustration of a mechanical pump drive unit and support nest structure in operative association with the pumping cartridge of FIG. 1.
Figure 6B:
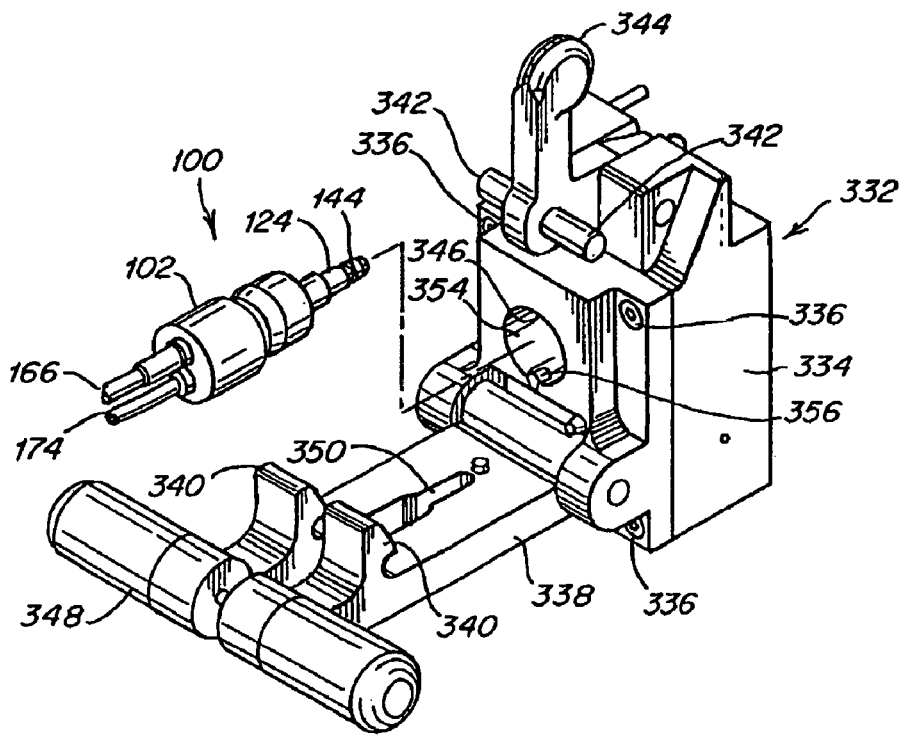
FIG. 6B is a schematic, perspective illustration of the support nest structure of FIG. 6A, shown in an open configuration prior to insertion of the pumping cartridge of FIG. 1.

FIG. 6A shows an exemplary mechanical drive unit 330 configured for coupling to pumping cartridge 100 (previously illustrated in FIGS. 1, and 2A-C) for driving piston rod 124 in reciprocating motion. As illustrated in FIG. 6A, support nest structure 332, which is configured to mate with and couple to pumping cartridge 100, is illustrated in its closed, operable configuration. FIG. 6B illustrates support nest structure 332 as configured in an open position prior to insertion pumping cartridge 100.

Mechanical pump drive unit 330 can comprise essentially any type of reciprocating mechanical pump drive known in the art. In some preferred embodiments, mechanical pump drive unit 330 is a variable speed and/or variable stroke length pump. Mechanical pump drive unit 330 can include a variety of manual and/or automatic controls for adjusting speed and/or stroke length as well as include a variety of other controls, alarms, displays, indicators, etc., typical of pump drive units utilized for commercial pumping purposes, particularly those utilized for medical and surgical pumping purposes. Nesting structure or support nest structure 332 can be modified or configured to be useable with a wide variety of commercially available mechanical pump drive units or with mechanical pump drive unit specifically designed and configured for use with the pumping cartridges provided according to the invention, as would be apparent to those of ordinary skill in the art.

Nesting structure 332 is constructed and arranged to support and immobilize pumping cartridge 100 during operation. The term "nesting structure" or "support nest structure," as used herein, refers to a structure or component of a mechanical pump drive unit or console that is configured for engaging in direct contact, the pumping cartridge, such that at least a portion of the structure at least partially surrounds at least a portion of the pumping cartridge. Specifically, support nest structure 332 is constructed to have a shape and configuration enabling it to couple the pumping cartridge in operative association with the pump drive unit, as illustrated in FIG. 6A.

Support nest structure 332 is preferably constructed of a sturdy material, such as a metal, for example stainless steel. As illustrated, nesting structure 332 includes a base component 334, configured for attachment to mechanical pump drive unit 330, for example via bolts 336. Pivotally connected to base 334 is a valve securing component 338 including notched catches 340 thereon, which are configured to engage pins 342 of the spring-loaded, pivotally-mounted latch 344 on base 334. Upon insertion of pumping cartridge 100 into pump cartridge receiving bore 346 of the nesting structure, valve securing component 338 is pivoted upward using handle 348 until notched catches 340 engage with pins 342, thus closing the nesting structure as illustrated in FIG. 6A.

Upon securing pumping cartridge 100 into the nesting structure as illustrated in FIG. 6A, as previously discussed, coupling notch 144 of piston rod 124 preferably engages a complementary latching mechanism (not shown, but see FIG. 14) within a reciprocating piston plunger (not shown, but see FIG. 14) of mechanical pump drive unit 330. In some embodiments, support nest structure 332 can include mechanical and/or electrical means for indicating to a control system of the mechanical pump drive unit and/or an operator of the mechanical pump drive unit that pumping cartridge 100 is properly engaged for operation. Such indication can be used to enable operation of the mechanical pump drive unit when the pumping cartridge is properly engaged, and prevent operation when the pumping cartridge in not engaged or improperly engaged. Mechanical and/or electrical means for performing the above function are well known in the art or involve only straightforward modifications of technology known in the art.

Valve securing component 338 is constructed and arranged to secure body portions 162 and 170 of inlet check valve 159 and outlet check valve 160, respectively to main body portion 102 of pumping cartridge 100, when the pumping cartridge is coupled in operative association with support nest structure as illustrated in FIG. 6A (see also FIG. 1). In preferred embodiments, valve securing component 338 secures the valves, as described above, such that a fluid-tight seal capable of withstanding a difference of pressure of at least about 1000 psi without substantial fluid leakage therethrough is created between the body portion of the valve and the bore in which the valve is inserted (e.g., bores 106 and 108 for valve body portion 162 and 170, respectively) of the main body portion of the pumping cartridge only upon coupling of the pumping cartridge in operative association with the support nest structure. In more preferred embodiments the seal is capable of withstanding a difference in pressure of at least about 5000 psi, in more preferred embodiments at least about 8000 psi, in some preferred embodiments at least about 15,000 psi, in other embodiments at least about 20,000 psi, in other embodiments at least about 30,000 psi and in other embodiments at least about 50,000 psi. The valve securing component is able to secure the valve body portion within the main body portion of the pumping cartridge by holding the valve body within the bore of the pumping cartridge in which it is inserted, thereby preventing the valve body from being extruded under pressure and effecting a seal (e.g., via O-rings 186 as illustrated in FIG. 1). Valve securing component 338 includes an aperture 350 therethrough to allow passage of fluid conduits 166 and 174, which are in fluid communication with the valves. Aperture 350 has a width, in the portion adjacent to the body portion of the valves when the nest structure is in a closed configuration as illustrated in FIG. 6A, which is less than the diameter of the shoulder portions 352 of the inlet and outlet fittings providing body portions of the valves (see also FIG. 1). Thus, upon closing valve securing component 338 against base 334, the valve securing component will press against shoulders 352 of the fittings holding the body portions of the valves in sealing engagement with main body portion 102 of pumping cartridge 100.

In preferred embodiments, nesting structure 332 provides an inner, pumping cartridge-contacting surface 354 (FIG. 6B) having contours and dimensions selected to be complementary to the contours and dimensions of the exterior surfaces of the pumping cartridge, such that upon coupling of the pumping cartridge and the support nest structure, a substantial fraction of the exterior surfaces of the pumping cartridge are supported by direct contact with the nest. Such a configuration is especially preferred when the main body portion of the pumping cartridge is constructed from materials that are not capable of withstanding the desired operating pressures of the pumping cartridge without failure, for example by bursting, cracking, splitting, etc., of the main body portion. Also, in preferred embodiments, the support nest structure and the pumping cartridge are shaped and configured so that they can be coupled in operative association only when the pumping cartridge is installed in a single, predetermined orientation. In the illustrated embodiment, inner pumping cartridge-contacting surface 354 includes a tab 356 thereon (FIG. 6B) configured and positioned to mate with orientation notch 203 of main body portion 102 of the pumping cartridge (see FIG. 2A). Thus, pumping cartridge 100 can only be inserted into bore 346, so that the pumping cartridge is in operative association as illustrated in FIG. 6A, when pumping cartridge is oriented such that orientation notch 203 mates with tab 356.

Figures 7, 8A:
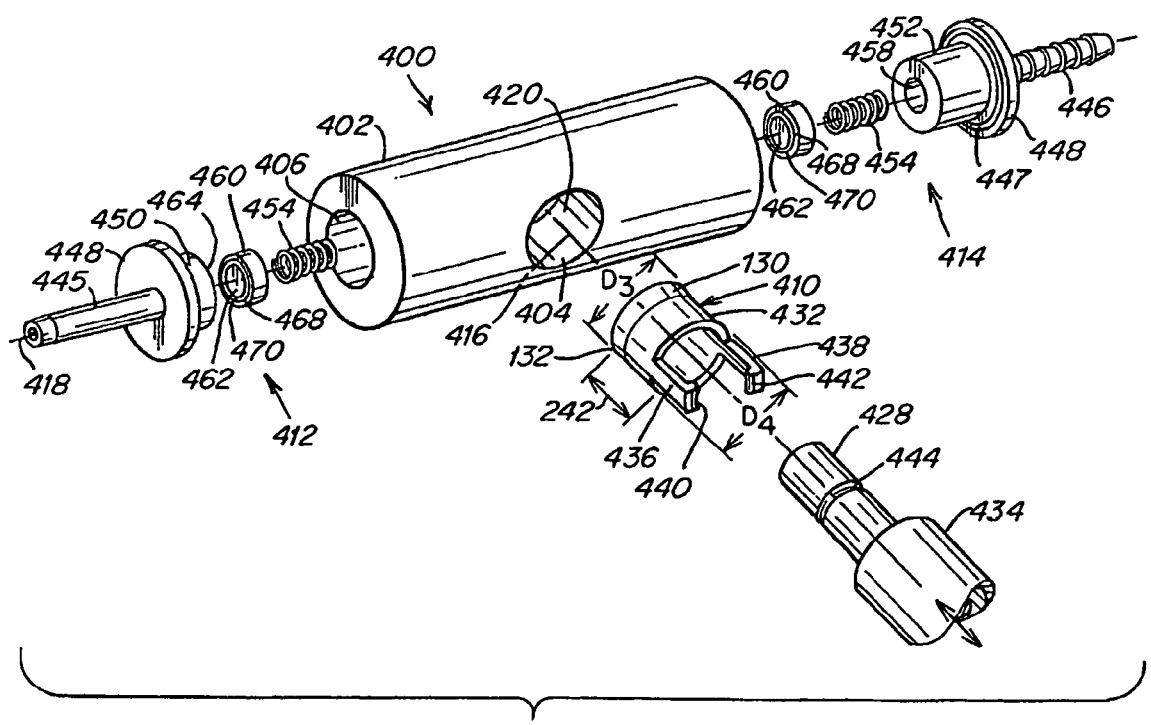
FIG. 7 is a schematic, exploded, perspective illustration of another embodiment of a pumping cartridge, having a T-shaped configuration, also illustrating a portion of a reusable pump drive system for use in operating the pumping cartridge.
FIG. 8A is a schematic, perspective illustration of a portion of a mechanical pump drive unit including a support nest designed for coupling the pumping cartridge of FIG. 7 in an operative configuration.

FIG. 7 illustrates an alternative embodiment of a pumping cartridge provided by the invention having a fluid flow path configuration essentially perpendicular to a centrally-disposed pump chamber, forming a "T-shaped" configuration. FIG. 8A illustrates a support nest structure and a portion of a mechanical pump drive unit for coupling the pumping cartridge in an operative configuration with a pump drive unit, and FIG. 8B illustrates a cross-sectional view of the pumping cartridge installed in the nesting structure in an operative configuration.

Figure 8B:
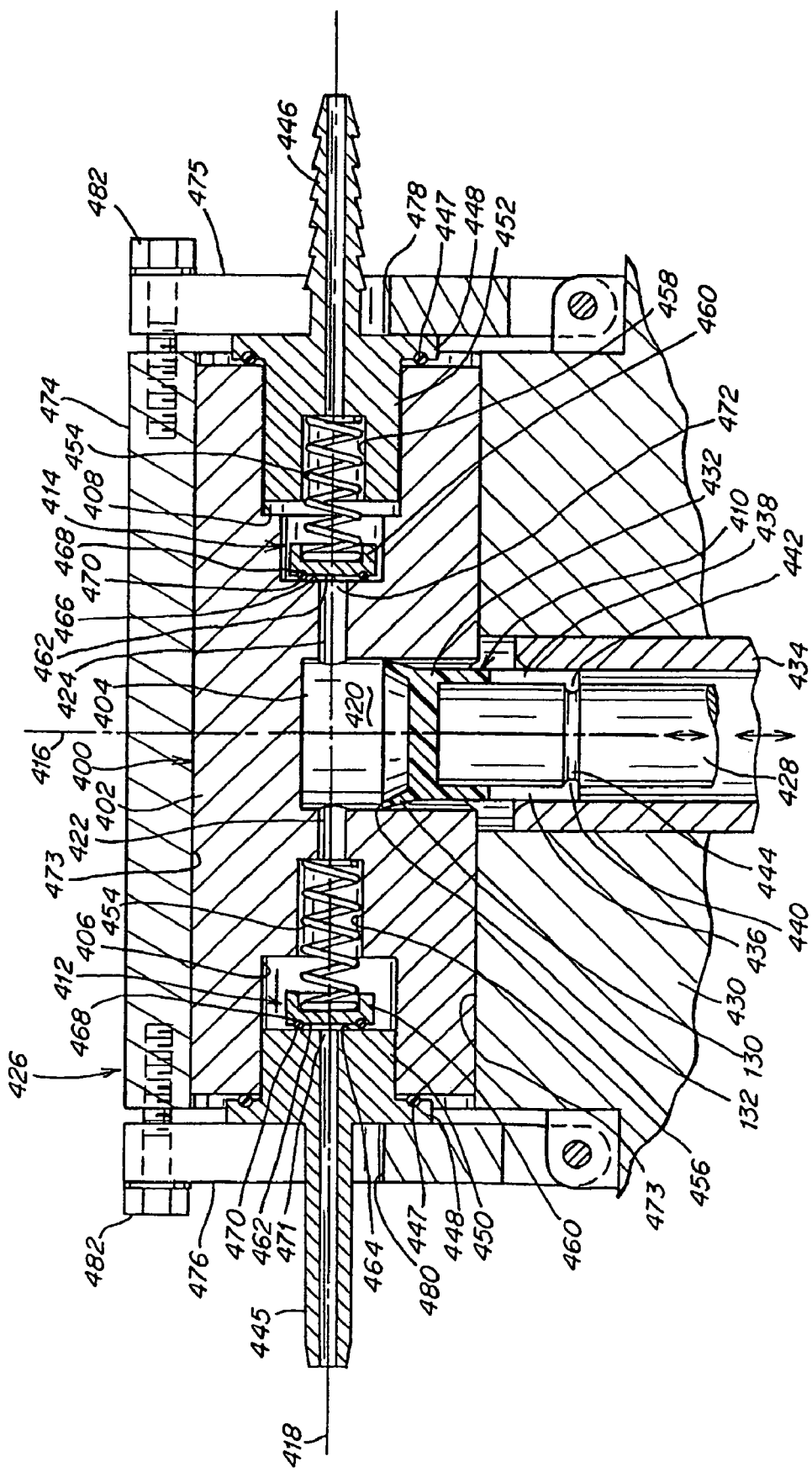
FIG. 8B is a schematic, cross-sectional illustration of the pumping cartridge of FIG. 7, when installed in operative association with the support nest structure of FIG. 8A.

Referring to FIGS. 7 and 8B, pumping cartridge 400 includes a main body portion 402, which is formed of three bores 404, 406, and 408. Bore 404 comprises a cylinder in which piston 410 reciprocates during operation. Bore 406 houses inlet check valve 412, and bore 408 houses outlet check valve 414. Cylinder 404 is essentially centrally disposed in main body portion 402 of pumping cartridge 400 and has a longitudinal axis 416. Bores 406 and 408 each have a longitudinal axis 418 oriented essentially perpendicular to the longitudinal axis 416 of cylinder 404, thereby creating a T-shaped flow path configuration of the pumping cartridge. Bores 406 and 408 are in fluid communication with pump chamber 420 of cylinder 404 via flow channels 422 and 424, respectively.

As with previously described pumping cartridge 100, the main body portion 402 of the pumping cartridge 400 can be formed by a wide variety of materials, essentially any of the materials previously mentioned for main body 102 of pumping cartridge 100. As previously discussed, in some embodiments, the main body portion can be formed of a rigid, pressure-supporting material, for example machined stainless steel, in which case the main body portion of the pumping cartridge can be resistant to operating pressures without the need for additional support from the nest structure. In alternative embodiments, for example embodiments where main body portion 402 is constructed of a material not capable of withstanding contemplated operating pressures, for example a molded polymeric material, the illustrated support nest structures 426 (see FIGS. 8A-B) can serve to surround and support the outer surfaces of the main body portion of the pumping cartridge to enable the pumping cartridge to withstand desired operating pressures, as discussed previously in the context of FIGS. 6A-B.

Pumping cartridge 400, as illustrated, does not include a flexible skirt forming a bioseal, as previously illustrated in pumping cartridge 100 of FIG. 1. It should be understood, that in alternative embodiments, pumping cartridge 400 could easily be configured to include such a flexible skirt, if desired.

Pumping cartridge 400 also illustrates an alternative means for providing a piston/piston rod coupling configuration. In contrast to the piston/piston rod configuration described above in the context of FIG. 1, piston rod 428 does not form part of the removable/detachable pumping cartridge assembly 400, but rather comprises part of the reusable mechanical pump drive unit 430. Piston 410 is configured as a removable, cap-like element which fits over the distal end of piston rod 428, upon coupling the pumping cartridge to support nest structure 426, and which is removable from the piston rod upon detachment and replacement of the pumping cartridge. Piston 410 preferably includes a main body portion 432 and sealing component 130, which are constructed of materials, and with dimensions, similar to those discussed above with regard to pistons 122, 250, 260. Mechanical pump drive unit 430 includes a retractable sheath 434 surrounding piston rod/reciprocating plunger 428. Prior to and/or upon installation of the pumping cartridge into support nest 426, retractable sheath 434 is retracted as illustrated in FIG. 7. Piston 410 can then be inserted upon the distal end of piston rod 428 so that proximally projecting arms 436 and 438, having engagement beads 440 and 442 thereon, respectively, engage notch 444 of piston rod/plunger 428. At this point, retractable sheath 434 is moved distally to at least partially surround arms 436 and 438 thereby securing beads 440 and 442 into notch 444, as illustrated in FIG. 8B. During operation, piston rod 428 and sheath 434 reciprocate as a unit, so that piston 410 is securely retained on the piston rod. The coupling mechanism described thus involves a snap-fit of piston 410 over and onto piston rod 428.

Inlet check valve 412 and outlet check valve 414 are also somewhat differently configured in pumping cartridge 400 than the check valves previously described in the context of pumping cartridge 100 of FIG. 1. Inlet fitting 445 and outlet fitting 446 are similar to those described previously in FIG. 1, except that the high pressure O-ring seals 447 are carried on shoulder portions 448, as opposed to body portions 450 and 452, as was previously the case in the embodiment described in FIG. 1. In addition, coil spring biasing elements 454 are somewhat smaller in diameter with respect to the diameter of bores 406 and 408 than the biasing elements previously described in FIG. 1. Accordingly, to prevent misalignment and undesirable lateral movement of springs 454 during operation, bore 406 of main body portion 402 and valve body portion 452 each include a relatively small diameter bore segment 456 and 458, respectively, to position and support springs 454.

Poppets 460 are also differently configured than those described above in the context of FIGS. 5A-C. Poppets 460 comprise sealing elements and have occluding surfaces 462 comprising essentially flat surfaces oriented essentially parallel to the planes defined by valve seats 464 of inlet check valve 412 and 466 of outlet check valve 414. Valve seat-facing occluding surfaces 462 include a circumferential groove 468 therein in which is disposed a circumferential lip element 470 comprising an elastomeric O-ring. The configuration and dimensional relationship between O-ring 470 and circumferential groove 468 is preferably similar to that discussed previously for high pressure O-ring seal 447 and the high pressure O-ring seals discussed above with respect to FIG. 1. In preferred embodiments, sealing elements 460 are constructed of a durable, rigid material, for example a metal. In alternative embodiments, instead of providing O-rings 470 as illustrated, the entire occluding surface of the poppet can be coated with or bonded to an elastomeric layer of material, or at least partially coated with such material in the region overlaying and/or surrounding apertures 471 and 472. In yet other alternative embodiments, the sealing element may be formed of an elastomeric or seal-forming resilient material able to form a pressure-tight seal with the valve seat without the need for O-rings. In other alternative embodiments, the sealing element may be substantially as shown, except not including circumferential groove 468. In such embodiments, the O-ring may be separate from the sealing element and simply positioned between the sealing element and the valve seat.

Support nest structure 426 is illustrated most clearly in FIGS. 8A and 8B. Support nest structure 426 is configured to serve essentially the same purposes as previously discussed with regard to support nest structure 332 illustrated previously in FIGS. 6A and 6B. As illustrated in FIG. 8A, support nest structure 426 provides inner pump cartridge-contacting surfaces 473 having contours and dimensions selected to be complementary to contours and dimensions of exterior surfaces of the pumping cartridge, so that upon coupling of the pumping cartridge and the support nest structure, as illustrated in FIG. 8B, a substantial fraction of the exterior surfaces of the pumping cartridge are supported by contact with the nest. Support nest structure 426 includes a main body supporting component 474 and two-hinged valve securing components 475 and 476. Each of the valve securing components includes an aperture 478 and 480 therethrough positioned and configured to press the inlet and outlet fittings into the main body portion of the pumping cartridge upon assembly, thus providing leak-tight support for the inlet and outlet check valves (see FIG. 8B), as similarly described in the context of FIGS. 6A and 6B above. As illustrated in FIG. 8B, components 474, 475, and 476 are secured to each other, upon coupling with pump cartridge 400 via bolt fasteners 482. It should be understood that in alternative embodiments, a wide variety of other well known fastening and securing means may be utilized as an alternative to bolt fasteners 482. For example, in another embodiment, a latch and release mechanism similar to that previously described in the context of FIGS. 6A and 6B could be employed, in which case the nesting structure could be assembled and disassembled by hand without the need for use of any tools.

Described below in FIGS. 9-13, and 16 are various configurations and embodiments of axially configured pumping cartridges provided according to the invention. "Axially configured," as used herein, refers to a pumping cartridge wherein the piston and at least one of an inlet and outlet check valve are both at least partially contained within one bore having an essentially continuous longitudinal axis, and where the longitudinal axis of the piston is essentially parallel to the longitudinal axis of the bore.

FIGS. 9A-C show a first embodiment of an axially configured pumping cartridge 500 having a main body portion 502 formed of a length of thin-walled tubing. While the main body portion of the piston can potentially be constructed of a wide variety of materials, for example those discussed above with regard to main body 102 of pumping cartridge 100, in preferred embodiments, the main body portion 502 comprises a length of a thin-walled metal, preferably stainless steel tubing. The particular wall thicknesses and inner diameters of the thin-wall tubing utilized to form main body portion 502 will, of course, depend on the needs of desired operating conditions of the pumping cartridge. In the illustrated embodiment, main body portion 502 comprises an about 3.5 inch to about 4 inch length of about 0.375 inch I.D. stainless steel tubing, with an outer diameter of about 0.5 inch. These configurations are also suitable for the axially-configured pumping cartridges described below as well. In preferred embodiments, main body portion 502 is constructed of tubing having a diameter and wall thickness sufficient to withstand the desired pumping pressures generated by the pumping cartridge during operation without bursting, splitting, or undue expansion that would be sufficient to cause or permit leakage or displacement of components positioned within the tubing during operation. (These are examples of "thin-walled" tubing as described above).

Contained within axial bore 504 of elongated tube 502 and aligned along a common longitudinal axis 506 are the various components comprising pumping cartridge 500, including piston rod 508, piston 510, inserts 512, 514 and 516, inlet check valve 518 and outlet check valve 520. The structure and configuration of central insert 514 is illustrated in greater detail in FIGS. 9B and 9C. In preferred embodiments, such as illustrated, each of the inlet and outlet check valves within the pumping cartridge is at least partially disposed within the axial bore of the tubing, such that essentially all moving parts of each valve are essentially completely contained within the axial bore. The moving parts of the check valve comprise the poppet and/or sealing element, as well as any biasing elements (for example, coil springs 196). In the illustrated embodiment, outlet check valve 520 is positioned at the distal end 522 of axial bore 504, piston 510 reciprocates proximally of the outlet valve, and inlet check valve 518 is positioned within insert 514 and is located between the outlet check valve and the piston.

Piston rod 508 and piston 510 are substantially similar to those described above in the context of FIGS. 1, 3 and 4, except that piston 510 is coupled to piston rod 508 via a barbed connection 524. Piston 510 is configured to reciprocate within cylinder 526 of axial bore 504 during operation. Check valves 518 and 520 are positioned within axial bore 504 by inserts 512, 514, and 516. Insert 514 includes two chambers 528 and 530 formed therein for surrounding the moving parts of inlet check valve 518 and outlet check valve 520, respectively. Insert 514 forms a body portion of each of check valves 518 and 520 as configured. The inserts also include channels formed therein (e.g. channels 532, 534, 536, 538, 540 and 541) providing inlet and/or outlet flow paths within pumping cartridge 500. The poppet, sealing elements and biasing elements of inlet check valve 518 and outlet check valve 520 are substantially equivalent to those described previously in the context of FIGS. 1 and 5.

As illustrated, inserts 512 and 514 comprise separate elements inserted and secured within axial bore 504. In alternative embodiments, the inserts can be formed as a single unit and/or can be formed as part of the main body portion of the pumping cartridge, for example, part of the structure of the main body can comprise channels and chambers machined therein (e.g. a main body portion of the pumping cartridge instead of being formed of a length of thin-walled tubing could be formed of a length of a solid piece of material that is machined to form the various chambers and flow paths illustrated). Though the inserts may be constructed of a wide variety of materials, including essentially all of the materials discussed above in the context of materials for forming main body portions of the pumping cartridges, in preferred embodiments, the inserts are preferably formed of a relatively rigid material, such as a hard, durable plastic or a metal, preferably stainless steel, and are machined or molded to form the various features, bores, channels, etc. illustrated by conventional machining or molding techniques.

The inserts can be secured within the axial bore of the pumping cartridge by a variety of means known to those of ordinary skill in the art. For example, inserts 514 and/or 516 can be sized to have an outer diameter somewhat larger than the inner diameter of the thin-wall tubing comprising the main body portion of the pumping cartridge and can be press fit into the axial bore, thus forming an interference fit sufficient to retain the inserts within the bore under pressure. Alternatively, one or both of the inserts can be retained within the bore via brazing, welding, adhesive bonding, etc., as would be apparent to those of ordinary skill in the art. Alternatively, as described in the context of FIGS. 6A-B and 8A-B, in alternative embodiments, inserts 514 and 516 could be retained within the axial bore under pressure only upon coupling of the pumping cartridge with a support nesting structure, which support nesting structure is configured to engage insert 516 holding it in place within the axial bore during operation.

Insert 512, as illustrated in FIG. 9A, is secured within the main body portion of the pumping cartridge via a crimp-seal method. This method involves positioning insert 512, which comprises a body portion of inlet check valve 518, within axial bore 504 and securing the insert within tubing 502 by forming a crimp 542 deforming the wall of the tubing into a channel or groove 544 of the insert, thereby creating a circumferential, essentially leak-tight seal between the tubing and the insert, without the need for any supplemental seals. In alternative embodiments, the insert may lack circumferential groove 544, and simply be slightly smaller in diameter than the axial bore, thereby permitting crimp 542 to be formed. However, this alternative configuration generally provides inferior sealing and leakage prevention and, therefore, is less preferred. In preferred embodiments, crimp 542 is formed around the circumference of the tubing such that it is essentially continuous. In an alternative embodiment, the crimp may comprise a series of discrete indentations around the circumference of the tubing and be discontinuous. In any crimp seal involving an insert having a circumferential groove(s), an O-ring may be placed in the groove before the tubing is crimped, if desired, to potentially improve sealing.

Somewhat similar crimp sealing methods are known in the art for use in other contexts; however, such crimp seals have not, it is believed, been employed for use in the manufacture or fabrication of a pumping cartridge from a length of thin-walled tubing, as provided by the present invention. The crimp seals provided according to the present invention can be formed using commercially-available equipment. For example, crimp seals as illustrated in FIG. 9A, as well as those in FIGS. 10A, 11A, 12A, 12B and 13A, were made utilizing standard radial crimping machinery (e.g., a six jaw UNI-FLEX™ radial crimper, type HM-150; Uniflex Hydraulic GMBH, Karben, Germany). The above examples use a stainless steel tube with a nominal outer diameter of 0.500 inch and a nominal inner diameter of 0.375 inch, with a wall thickness of about 0.0625 inch. The depth of the channel (e.g. 544) in the inserts within the tubing (e.g. insert 512) is formed to be preferably approximately equal to the thickness of the tubing wall, and the width of the channel is, in this example, about three times the wall thickness, while the maximal width of the crimp-forming projection on the crimping jaws (not shown) is about 1.3 times the wall thickness, and its depth is similar to the wall thickness. Portions (e.g. 545) of the insert (e.g. 512) beyond the groove (e.g. 544) should be significantly longer than the wall thickness, e.g. at least about 1.5 times longer, to prevent distortion. The final, total inward penetration of the crimp-forming die projections is adjusted to avoid significant distortion/collapse of the channel passing through the insert, (e.g., passage 532 or passage 740 in FIG. 11A), or of the tubing beyond the insert. Modifications of crimping dies and machinery, and of dimensions of the insert, can readily be accomplished by those familiar with radial crimping technology. Preferably, upon crimping of the tubing onto the insert, a circumferential, leak-tight seal is created between the tubing and the insert, optionally without the use of any supplemental seals, which is capable of withstanding a pressure difference across the seal at least about 1,000 psi, more preferably at least about 5,000 psi, more preferably at least about 8,000 psi, in some preferred embodiments at least about 15,000 psi, in other embodiments at least about 20,000 psi, in other embodiments at least about 30,000 psi, and in yet other embodiments at least about 50,000 psi.

Pumping cartridge 500 can be operated as follows. To fill the pump chamber 527 with fluid to be pumped, piston rod 508 and piston 510 are moved proximally in the direction of arrow 546. During this intake stroke, fluid to be pumped flows through inlet aperture 548 in the side wall of tubing 502, through channels 536 and 534 within insert 514, through inlet check valve 518 and flow channel 532 of insert 512, and into the pump chamber. During this filling step, inlet check valve 518 is configured in an open position, while outlet check valve 520 is configured in a closed position.

During the discharge stroke, piston rod 508 and piston 510 are moved distally in the direction of arrow 550 forcing fluid from the pump chamber through channel 532 and into inlet check valve chamber 528. Pressure of this fluid impinging upon sealing element 188 will tend to force the sealing element against valve seat 552, providing a pressure-tight seal. The fluid then flows out of chamber 528 via aperture 554, through channel 538 and channel 540, past open outlet check valve 520, and finally out of the pumping cartridge via flow path 541.

Insert 514 includes a circular groove 556 circumscribing the perimeter of inlet channel 536, which contains therein, when the insert is inserted in an operable configuration within the axial bore, an O-ring 558. The seal formed by contact of the O-ring with the inner surface of the axial bore prevents high pressure liquid generated during the discharge stroke of the piston from escaping from the pumping cartridge via inlet aperture 548. Insert 514 also includes a circumferential groove 560 which contains an O-ring 562, forming a seal, when assembled, preventing pumped liquid from leaking between the insert and the inner wall of the axial bore. Similarly, insert 516 includes a similar circumferential groove 562 containing O-ring 564, which create a seal performing essentially the same function as described immediately above. It should be noted that the configuration of the grooves and O-rings utilized for effecting the above-mentioned seals are preferably as described previously in the context of the high pressure O-ring seals of the pumping cartridge of FIG. 1. O-ring seals discussed in the remainder of the specification are also preferably of the high pressure configuration discussed in FIG. 1, unless otherwise specified in the discussion.

FIG. 10A illustrates an alternative embodiment of the pumping cartridge of FIG. 9A. For clarity, the piston rod and piston, which can be essentially the same as piston rod and piston of FIG. 9A, are not illustrated. Pumping cartridge 600 is similar in many ways to pumping cartridge 500 illustrated in FIG. 9A above. Accordingly, only the substantial differences are highlighted below. Centrally disposed insert 604 of pumping cartridge 600 (shown more clearly in FIGS. 10B-C) is configured somewhat differently than insert 514 previous described. Insert 604 includes chambers 606 and 608, which surround the moving parts of inlet check valve 610 and outlet check valve 612, respectively, which are displaced from the axial center line 506 of the pumping cartridge. This configuration permits a somewhat less complex and easier to machine fluid flow path configuration and eliminates the need for provision of a peripheral O-ring channel surrounding the inlet flow port (i.e., O-ring channel 556 previously illustrated).

In the present embodiment, the leakage of high pressure fluid past the insert can be effectively prevented by provision of two circumferential channels 614, 616 for containing O-rings 618 and 620, respectively. Insert 604 includes an inlet flow path 622 in fluid communication with an inlet aperture 624, which, in turn, is in fluid communication with inlet aperture 626 through the side wall of tubing 502. Inlet aperture 624, as illustrated in FIG. 10C, is positioned in a recessed portion 628 of spool region 630 of the insert. Insert 604 also includes an output channel 632 in fluid communication with outlet check valve chamber 608 and also in fluid communication with inlet check valve chamber 606 via aperture 634. Distal insert 636 provides a high pressure fluid connector 638, which has a different coupling configuration to the high pressure outlet fluid line (not shown) than that shown previously for insert 516 of FIG. 9A. In addition, insert 636 is secured within tubing 502 via a crimp 542, in a similar fashion as insert 512.

In addition, inlet check valve 610 and outlet check valve 612 include poppets 640, which are somewhat different in configuration than poppets 186 previously described. Specifically, poppets 640, instead of having a main body portion with an inner diameter somewhat larger than the spring biasing element as previously illustrated, have a main body portion 642 having a cylindrical upper portion 644 with an outer diameter slightly less than the inner diameter of coil springs 646, and a base portion 648 having a diameter larger than the outer diameter of the cylindrical portion and essentially the same as the outer diameter of spring 646. In this configuration, spring 646, instead of being positioned within the main body portion of the poppet as described previously, is positioned around the outside surface of the upper cylindrical portion 644 of the main body portion of the poppet.

FIG. 11A illustrates a first embodiment of an axially configured pumping cartridge including a valved piston. Piston 702 of pumping cartridge 700 is annular in shape with a centrally disposed flow path 704 therethrough. As will be explained in more detail below, during the filling step of the region 706 of cylinder 708 downstream of the piston, liquid or other fluid flows through the piston to fill the region of the cylinder downstream of the piston with the liquid/fluid. Piston 702 is coupled to the barbed distal end 710 of piston rod 712. Piston rod 712 includes a flow path 714 therein placing cylinder 708 in fluid communication with an inlet line (not shown) connected to inlet 716 of the piston rod. Piston rod 712 has a flared proximal end 718 configured for coupling to a reciprocating plunger of a mechanical pump drive unit (not shown).

Piston 702 together with poppet 720 and retaining mechanism 722 comprise an inlet valve 724 of the pumping cartridge. Poppet 720 is comprised of sealing element 726, which is substantially similar in configuration to the above-described valve sealing elements provided according to other embodiments of the invention. Poppet 720, however, does not include a main body portion as previously illustrated. Valve seat 728 is formed from the distal surface of main body portion 730 of piston 702. Sealing element 726 is retained against valve seat 728 via tension applied to wire 731 by coil spring 732, which is connected to the proximal end of the wire. The distal end of wire 731 is attached to sealing element 726. Coil spring 732 is anchored within chamber 734 of piston rod 712 via plate 736, which can be welded or otherwise secured in chamber 734.

Inlet check valve 724 operates as follows. During the filling stroke, piston rod 712 is retracted along direction 546. As a result of either or both of a vacuum created in region 706 and positive inlet pressure supplied to channel 730 in the piston rod, sealing element 726 tends to move distally, with respect to piston 702, into a position illustrated by dashed lines 738. In this configuration, sealing element 726 is not in sealing contact with valve seat 728, and inlet valve 724 is thus opened to permit fluid flow into region 706. During a discharge stroke, piston rod 712 is moved in direction 550 creating a fluid-induced force on sealing element 726 forcing it against valve seat 728, thereby forming a pressure-tight seal. The pressurized fluid then flows from region 706, through channel 740 of insert 512, past poppet 640 of outlet check valve 744 (positioned within insert 746), and out of pumping cartridge 700 through channel 748 of insert/outlet fitting 636.

FIG. 11B illustrates an alternative embodiment of an axially configured pumping cartridge including a valved piston, and having a differently configured piston rod and outlet valve assembly than the embodiment illustrated in FIG. 11A. Pumping cartridge 800 includes a piston rod 802, coupled to piston 702, which has a mechanical pump drive coupling region 126 of substantially the same configurations that were described previously for piston rod 124 of pumping cartridge 100. Piston rod 802 includes an inlet aperture 804 in fluid communication with inlet chamber 806 and inlet channel 808. Sealing element 726 is retained against valve seat 728 of piston 702 via a wire 810 attached to the sealing element at its distal end and attached to coil spring 812 at its proximal end. Coil spring 812 has a proximal-most coil 814 that circumscribes a diameter somewhat larger than the diameter circumscribed by coils 816 within flow channel 808, and larger than the diameter of channel 808, thus serving to position and retain spring 812 within flow channel 808 during operation.

Outlet valve 820 is also configured somewhat differently than outlet valve 744 previously illustrated in FIG. 11A. Specifically, outlet valve 820 utilizes a poppet 822 having a main body portion 824 with an outer diameter only slightly less than the inner diameter of tubing 502. Poppet 822 includes a main body portion 824 having a substantially solid cross-section, but including a centrally disposed bore 826 therein into which a tube 828 having a spring loaded pin 830 is inserted. Spring 832, contained within tube 828, is under compression, so that the spring exerts a force on pin 830 tending to force sealing element 188 and poppet 822 against valve seat 834. The distal end of tube 828 is contained within outlet flow channel 748 of outlet fitting/insert 636.

Figure 11C:
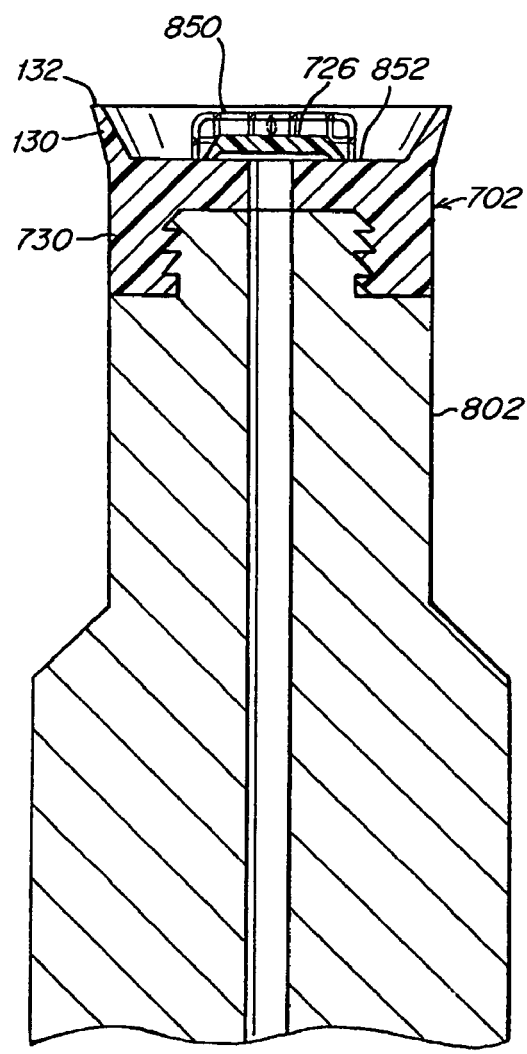
FIG. 11C is a schematic, cross-sectional illustration of a portion of an alternative embodiment of a piston and piston rod assembly comprising a valved piston.

FIG. 11C illustrates an alternative inlet valve configuration for valved piston 702. Instead of the spring/wire retaining mechanism previously illustrated, in the presently illustrated embodiment, sealing element 726 is retained by a screen or wire mesh 850 attached to distal surface 852 of main body portion 730 of piston 702. Retaining element 850 should be sized and positioned to prevent substantial lateral movement of retaining element 726, but should provide enough axial movement of element 726 to enable a relatively unrestricted flow of fluid past the element during filling of the pump chamber.

Figure 11D:
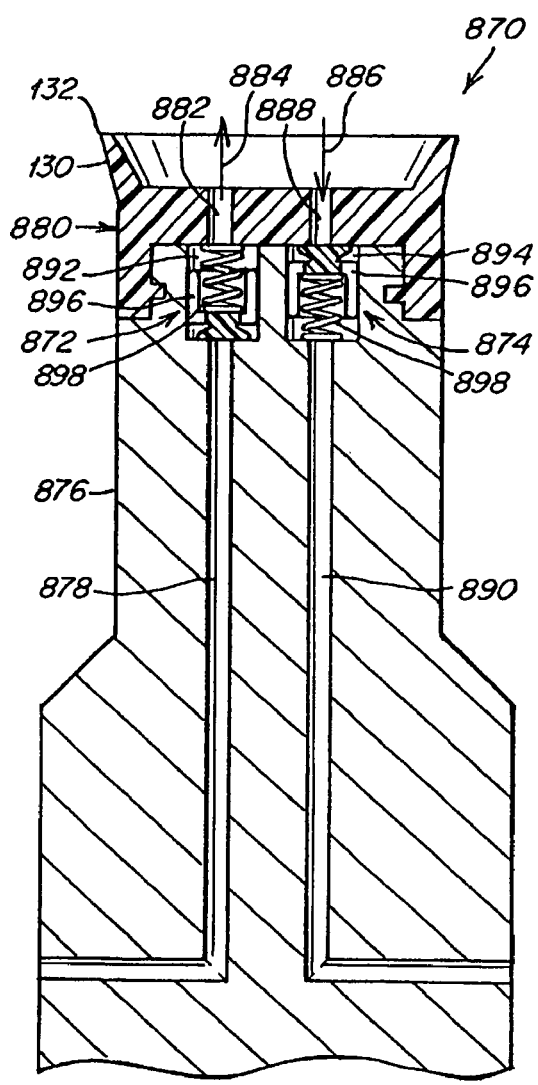
FIG. 11D is a schematic, cross-sectional illustration of a portion of an embodiment of a piston-piston rod assembly including two valves therein.

FIG. 11D illustrates an alternative valve piston assembly 870 including two valves 872 and 874 therein. Valve 872 is configured as an inlet check valve, permitting fluid flow through piston rod 876 along fluid flow path 878 and through piston 880 via flow channel 882 in the direction of arrow 884. Outlet valve 874 is configured to permit fluid flow in the direction of arrow 886 through outlet channel 888 of piston 880 and along outlet flow path 890 of piston rod 876. As illustrated, inlet check valve 872 is located within chamber 892 of piston rod 876 and outlet check valve 874 is located within chamber 894 of piston rod 876. In alternative embodiments, one or both of the check valves could be partially or completely contained within a chamber or bore formed in the piston, as opposed to the piston rod. Poppets 896 and biasing springs 898 can be substantially similar in design to those previously described in the context of FIGS. 1 and 5A-C, except that, typically, the outer diameter of the poppets and springs in the presently illustrated embodiment are somewhat less than that previously described, in order to enable them to fit within the confines of piston rod 876 as illustrated.

FIGS. 12A-12F illustrate various views and components of an axially configured pumping cartridge 900 including a valved piston comprising a floating piston, which is moveable relative to the piston rod to which it is connected. Pumping cartridge 900 has a main body portion 902 formed of thin-walled tubing 502, as previously described. Contained within the axial bore of elongated tube 502 is an outlet check valve assembly 904 comprising inserts 906, 908 and spring 910 biased poppet 912. Inserts 906 and 908 are retained within tube 502 via crimp seals 542, previously described. Insert 908, positioned at the distal end of pumping cartridge 900, forms an outlet fitting providing high pressure fluid connection 914 for attachment to high pressure outlet tubing (not shown). Each of inserts 906 and 908 include circumferential, high-pressure O-ring seals 916, essentially equivalent to those described above in previous embodiments.

Figure 12C:
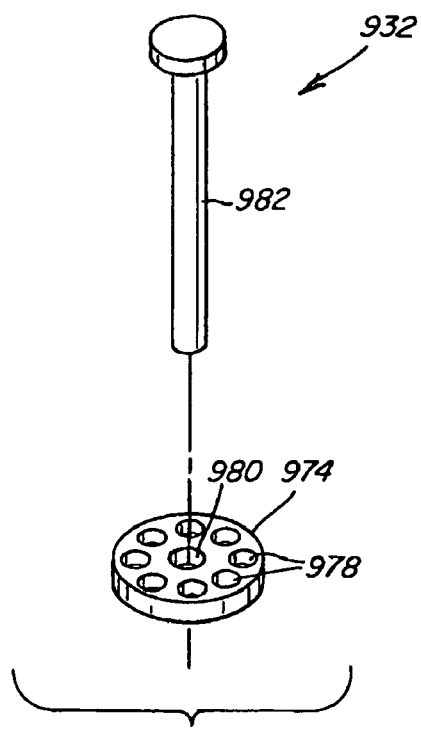
FIG. 12C is a schematic, exploded illustration of a piston retaining element and coupling pin of the pumping cartridge of FIG. 12A.
Figure 12D:
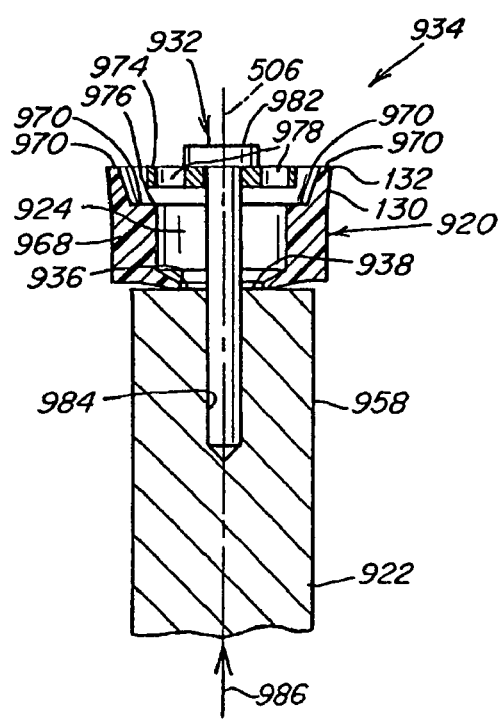
FIG. 12D is a schematic, cross-sectional illustration of a portion of the floating piston-piston rod assembly of the pumping cartridge of FIG. 12A, with the inlet valve in a closed configuration.
Figure 12E:
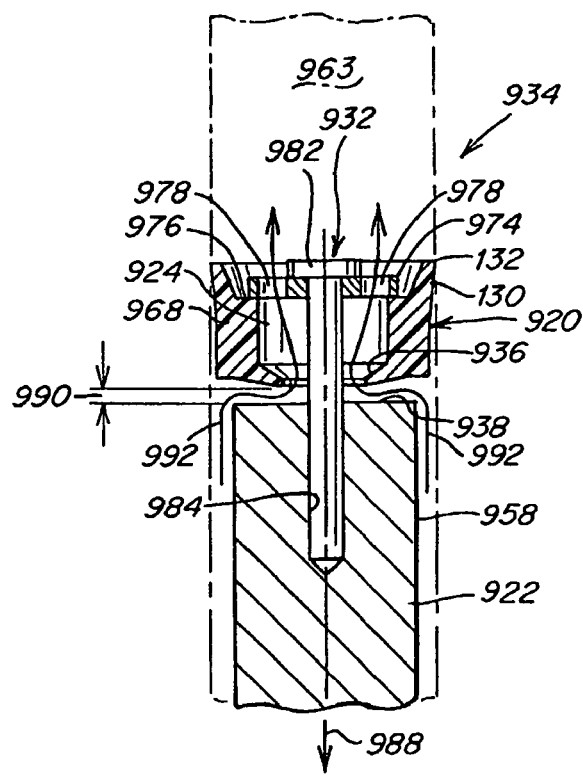
FIG. 12E is a schematic, cross-sectional illustration of the floating piston-piston rod assembly of FIG. 12D, with the inlet valve in an open configuration.
Figure 12F:
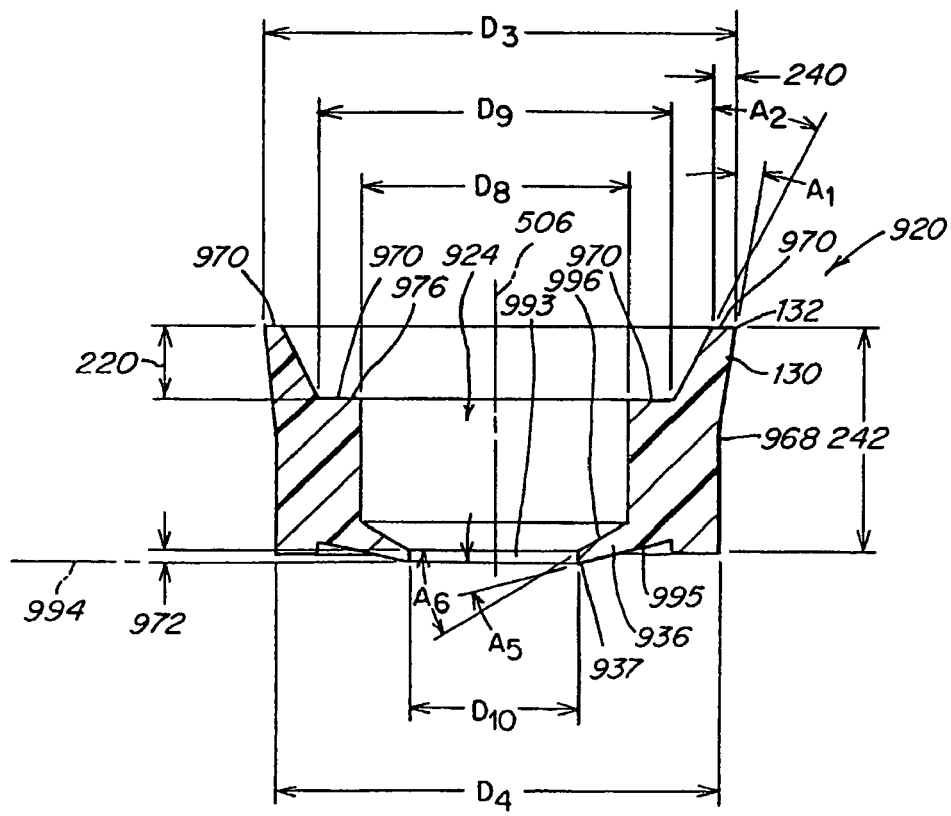
FIG. 12F is an enlarged, schematic, cross-sectional illustration of the floating piston of the pumping cartridge of FIG. 12A.

The most substantial differences differentiating the present embodiment from previously described axially configured pumping cartridges involve the configuration of floating piston 920 and piston rod 922 (see FIGS. 12D-F). As illustrated most clearly in FIG. 12F, piston 920 is annular in shape with a centrally disposed bore 924 therethrough defining a flow channel during a portion of the reciprocation of the piston in axial bore/cylinder 926.

In the illustrated embodiment, piston rod 922 has a proximal end including a mechanical pump drive coupling region 126, as previously described. In the embodiment illustrated, a flexible skirt 928, providing a bioseal, is attached, for example by an adhesive, to piston rod 922 and to a side wall 930 of tubing 502.

Piston rod 922 is constructed and positioned to apply force to floating piston 920 to drive the motion of the piston during operation. Floating piston 920 is coupled to piston rod 922 via a coupling 932 permitting relative motion between the piston and the piston rod during at least part of the reciprocating motion of the piston within the cylinder. Piston rod 922 and piston 920 together form an inlet check valve 934. As discussed in more detail below in the context of FIG. 12F, floating piston 920, in addition to including a first, cylinder wall sealing component 130 comprising a flared sealing flange 132, as previously described for the above-illustrated pistons, also includes a valve sealing element 936 comprising a proximal sealing flange/second sealing component, which is constructed and arranged to make sealing contact with a distal surface 938 of piston rod 922 (which distal surface comprises the valve seat of the inlet valve) during the pressure-generating stroke of the piston (see especially FIG. 12D). As used herein, a proximal sealing flange is "constructed and arranged to make sealing contact" with a distal surface of the piston rod when such sealing flange has a mechanical structure and material properties allowing the flange to contact the distal surface of the piston rod and create an interface of contact between the surfaces, thereby forming a seal that is able to maintain a hydrostatic pressure thereacross without substantial leakage therethrough. In preferred embodiments, such seal is able to withstand a pressure difference of at least about 1,000 psi, in more preferred embodiments at least about 5,000 psi, in even more preferred embodiments at least about 8,000 psi, in some preferred embodiments at least about 15,000 psi, in other embodiments at least about 20,000 psi, in other embodiments at least about 30,000 psi, and in yet other embodiments of at least about 50,000 psi. Floating piston 920 essentially combines both the cylinder sealing features described above in the context of previously illustrated pistons (e.g. piston 122 of pumping cartridge 100), as well as a valve sealing element similar in function to the sealing elements described above (e.g. see FIGS. 5A-C and associated discussion).

As seen most clearly in FIGS. 12D-F, the proximal sealing flange 936 comprises a circumferential flange projecting inwardly towards the center of bore 924 and proximally towards valve seat 938 of piston rod 922.

Fluid to be pumped enters pumping cartridge 900 via inlet line 940 which is connected to inlet clamp 942 (shown in greater detail in FIG. 12B. Inlet clamp 942 comprises a C-shaped spring clamp that is sized and configured to snap onto side wall 930 of tubing 502. Spring clamp 942 can be formed of a wide variety of resilient materials, and is preferably constructed of a semi-rigid plastic material, such as an epoxy polymer. Spring clamp 942 includes a shoulder section 944 having a tubing-facing surface with a peripheral groove 946 therein for housing an elastomeric O-ring 948. Shoulder component 944 includes a centrally disposed projecting tube 950 forming a terminal end of fluid flow path 952 through the spring clamp. Inlet aperture 953 through side wall 930 of tubing 902 is located proximally of piston 920. Tubular projection 950 has a diameter configured to snuggly fit within aperture 953 in side wall 930 of tubing 502 and a length sufficient to traverse at least a portion of the wall thickness of tubing 502. The natural resiliency of spring clamp 942 creates a compression force able to form a leak-tight seal between O-ring 948 and side wall 930 of tubing 502, thereby preventing any leakage of the inlet fluid. Because the fluid pressures in this region are relatively low (e.g. approximately atmospheric) this O-ring seal need not be of the previously-described high pressure variety.

Piston rod 922 has a proximal portion 956 having an outer diameter only slightly less than the inner diameter of tube 502 for providing a close sliding fit. By contrast, piston rod 922 includes a distal region 958 having a smaller inner diameter, thus providing an annular space 960 between the piston rod and inner surface 962 of cylinder 926, thereby forming an inlet flow path for fluid entering a region 963 of cylinder 926 downstream of piston 920 during the filling stroke (see FIG. 12E). To prevent leakage of fluid from the proximal end of tube 502, for example into the interior of flexible skirt 928, during operation, proximal end 956 of piston rod 922 preferably includes therein a circumferential grove 964 containing an elastomeric O-ring 966 therein, which provides a sliding seal between piston rod 922 and the inner surface of tubing 502 preventing leakage. Because fluid pressures proximal to the floating piston are relatively low during operation, as discussed above, this O-ring seal need not be of the high-pressure variety discussed above and in previous embodiments. Reference is now made specifically to FIG. 12C-D. FIG. 12C shows an exploded view of coupling mechanism 932 connecting floating piston 920 to piston rod 922. FIG. 12D is a detail view of the piston and piston rod as configured during a discharge stroke of pumping cartridge, when inlet check valve 934 is a closed configuration. It should be mentioned at this point, that while floating piston 920, as illustrated, comprises a single, unitary element, in other embodiment, the piston can be constructed as more than one element that are connected and/or attached together. In the preferred, illustrated embodiment, main body portion 968, first sealing component 130, and second sealing component 936 are integrally formed. In particularly preferred embodiments, the piston is formed of an injected molded polymeric material, most preferably of those materials described above as being preferable for forming the pistons of the above-illustrated pumping cartridge embodiments. In order to provide a structure able to withstand high pumping pressures, for example greater than 1000 psig, it is preferred that all fluid-contacting surfaces oriented essentially perpendicular to the longitudinal axis 506 of the cylinder/piston that are not directly supported by the piston rod (e.g. surfaces 970) have a minimum cross sectional thickness exceeding a minimal cross sectional thickness of the sealing flange portions of the piston (i.e. thickness 240 and 972, see FIG. 12F).

Coupling mechanism 932 includes a piston retaining element 974 coupled to, or, in alternative embodiments formed by, distal surface 938 of piston rod 922. Retaining element 974 is constructed and positioned to contact the distal of portion 976 of main body portion 968 of piston 920 during the filling stroke (see FIG. 12E), so as to pull the piston proximally within the cylinder. As illustrated, piston retaining element 974 comprises a perforated disk including a plurality of peripheral channels 978 formed therethrough providing fluid flow paths, and a centrally disposed channel 980 through which coupling pin 982 is inserted. Coupling pin 982 is attachably retained in bore 984 of piston rod 922. In the illustrated embodiment, the pin is retained by means of an adhesive. In alternative embodiments, the particular coupling configuration can be other than as shown. For example, pin 982 could be replaced with a screw, rivet, barbed fitting, or other securing means. Alternatively, the piston retaining element and coupling means can be integrally formed as part of the distal end of the piston rod. Also, piston retaining element 974 and pin 982 need not be separate components but can, in alternative embodiments, be integrally formed. When retaining element 974 and pin 982 are separate elements, as shown, it should be apparent that the outer diameter of pin 982 should be somewhat greater than the inner diameter of bore 980, so that retaining element 974 is securely retained on the pin by an interference fit, so as to prevent it from moving axially relative to the pin. In alternative embodiments, such interference fit may be replaced by alternative securing means, for example by an adhesive, retaining clamp, retaining flange on the pin, etc.

As illustrated in FIG. 12D, when the piston is moved in the direction of arrow 986 during a discharge stroke, friction forces between flared sealing flange 132 and the cylinder wall, and/or hydrodynamic forces will tend to move the piston proximally relative to the piston rod 922 forcing valve sealing element 936 against distal surface 938 of the piston rod, thereby creating a seal. As the pressure in the cylinder is increased, additional force is applied to valve sealing element 936, thereby increasing the tenacity of the seal formed between the piston and the piston rod.

Reference is now made to FIG. 12E illustrating the configuration of the piston rod and piston during the intake portion of the pump stroke. During the intake stroke, when piston rod 922 is moved proximally in the direction of 988, as above, frictional drag of sealing flange 132 against the inner surface of the cylinder and/or hydrodynamic drag causes floating piston 920 to move distally with respect to piston rod 922 creating a gap 990 defining a liquid flow path 992 through bore 924 of the piston and channels 978 of retaining element 974, thereby filling the region 963 of cylinder 926 downstream of the piston. In essence, what occurs is that piston 920, during intake, moves proximally through a reservoir of fluid contained in channels 960 surrounding distal portion of 958 of piston rod 922. In addition, additional fluid is drawn into cylinder 926 proximal to the piston during the intake stroke due to a slight vacuum created in region 963 during retraction of the piston. Thus, it is generally not required to supply fluid to inlet 952 under positive pressure, although this can be done, in some embodiments, if desired, to reduce the force required to retract the piston and piston rod and/or to reduce wear and stress on piston 920 and/or piston retaining element 974 and/or pin 982.

During retraction of piston rod 922, piston 920 moves distally with respect to the piston rod until distal surface 976 of main body portion 968 of the piston comes in contact with piston retaining element 974 and is retained from further distal movement with respect to the piston rod. The range of relative motion between the piston and piston rod 990 is equal to the difference between the stroke length of the piston rod and the piston during reciprocation. This distance may be adjusted, for example by adjusting the length of pin 982 projecting distally from piston rod 922, to provide a desired piston stroke length that is less than the stroke length of the piston rod.

An enlarged, detail view of floating piston 920 is illustrated in FIG. 12F. In preferred embodiments, the dimensions and configuration of portions of the piston configured to form a sliding seal with the inner cylinder surface of the pumping cartridge, for example first, cylinder sealing component 130 including flared sealing flange 132, in preferred embodiments, are substantially similar or equivalent to similar features discussed with regard to previously illustrated pistons. Features which are preferably substantially similar in configuration to those previously described are given the same figure labels as those previously used for the above-described pistons. Similarly, dimensions and angles which have values preferably falling within the ranges previously described are also called out by the same notation or figure labels (e.g. diameters $D_3$ and $D_4$, angles, $A_1$ and $A_2$, and dimensions 220, 240 and 242). It should be noted that the above-mentioned dimensions are given with regard to a piston designed for use in a pump chamber having an inner diameter of about 0.375 inch, as discussed above. As previously mentioned, the optimal dimensions, angles, and configuration will depend, to some extent, on the bore size in which the piston is designed to reciprocate, the materials of construction and the configuration of the piston, desired operating pressures, pump speed, and other operating conditions, etc. As previously discussed, the specific design and configuration of the piston for effective or optimal performance is typically and readily determinable by screening tests involving routine experimentation and optimization.

In the illustrated example, inner diameter $D_8$ of centrally disposed bore 924 of main body 968 of piston 920 is about 0.22 inch. Outer diameter $D_9$ of shoulder region 976 of main body portion 968 is about 0.29 inch, and inner diameter $D_{10}$ of bore 993, whose periphery is defined by second sealing component 936, is about 0.14 inch. A typical value of thickness 972 of second sealing component 936 is about 0.01 inch. It should be understood that each of these values can be varied both positively and negatively from the above-mentioned illustrative values while still providing adequate, and potentially superior function in comparison to a piston having the above dimensions, for many operating conditions. As emphasized previously, optimal values of each of the above-mentioned dimension will depend upon various previously-mentioned factors and are best determined via routine testing and optimization under desired operating conditions. As illustrated, $D_9$ is about 80% of $D_4$; $D_8$ is about 80% of $D_9$; and $D_{10}$ is about 40% of $D_4$, or about 50% of $D_9$. These ratios are operable and convenient for several exemplary configurations and operating conditions, but can be varied depending on the material of construction, the applied pressure, and system backpressure and flow requirements. As discussed previously, particular parameters should be determined based on routine testing and optimization under desired operating conditions. There are general considerations that typically apply to essentially any design. $D_9$ will be less than $D_4$ by an amount determined by the thickness 240, length 220, and the angle A2. $D_8$ will be less than $D_9$ by an amount sufficient to allow the shoulder to engage the piston retaining element 974 (see FIGS. 12C, 12D), and by an amount small enough (or with an absolute diameter large enough) to avoid blocking flow paths 978 in the retainer 974. $D_{10}$ will be smaller than $D_8$ by an amount essentially equal to the radial inward projection extent of sealing elements 936.

Circumferential, flared sealing flange portion 937 of second sealing component 936 is characterized by a valve seat-facing surface 995 forming a first angle $A_5$ with respect to a plane 994 essentially perpendicular to axis 506, and a distal facing surface 996 forming a second angle $A_6$ with respect to the plane. In preferred embodiments, angle $A_6$ is greater than angle $A_5$. In some preferred embodiments, angle $A_5$ is between about 6 degrees and about 25 degrees, in more preferred embodiments, angle $A_5$ is between about 10 degrees and about 15 degrees, and in one preferred embodiment angle $A_5$ is about 12 degrees. In preferred embodiments, angle $A_6$ is between about 15 degrees and about 60 degrees. In more preferred embodiments angle $A_6$ is between about 20 degrees and about 40 degrees, and in one preferred embodiment angle $A_6$ is about 30 degrees.

Figure 13:
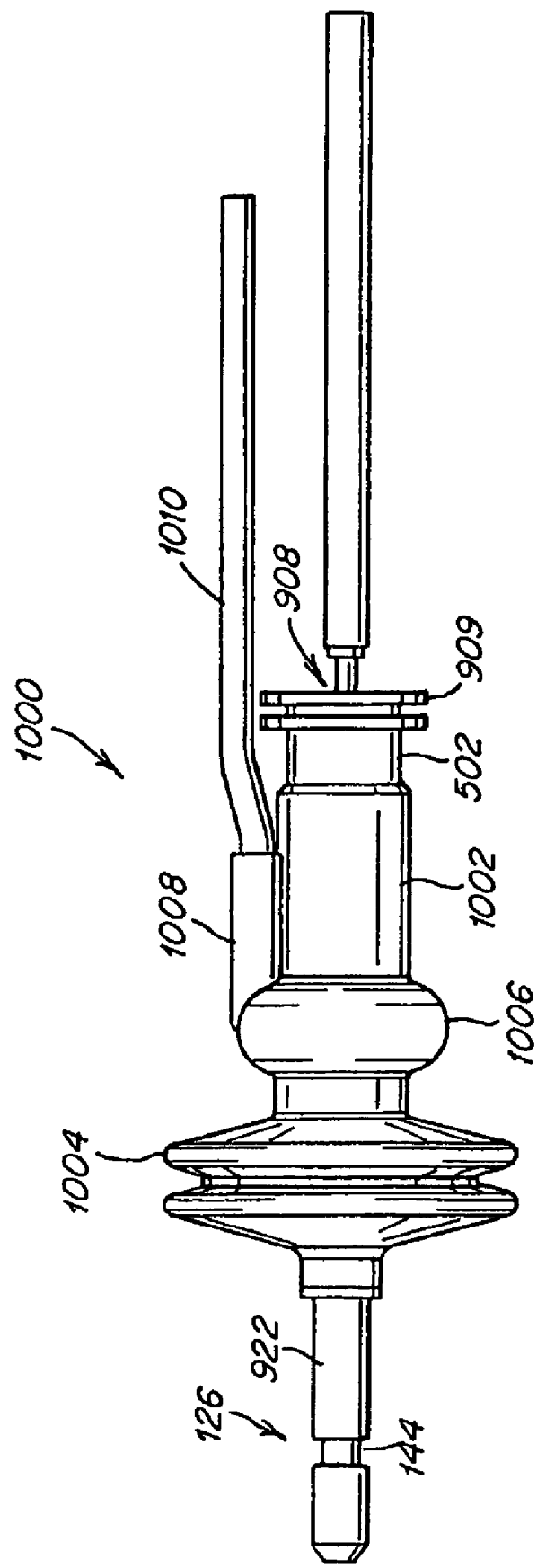
FIG. 13 is a schematic illustration of an alternative embodiment of the pumping cartridge of FIG. 12A.

FIG. 13 illustrates an alternative configuration 1000 of pumping cartridge 900 previously illustrated in FIG. 12A. Pumping cartridge 1000 is substantially equivalent to pumping cartridge 900, except that instead of having the inlet line being attached to the pumping cartridge via a spring clamp 942 and having a discrete flexible skirt component 928, pumping cartridge 1000 includes a resilient sheath or coating 1002, which performs both of the above functions. Resilient sheath or coating 1002 encapsulates elongated tube 502 from a region distal of inlet bore 953 (see FIG. 12A) to a region proximal of the tube, where sheath or coating 1002 is sealingly attached to piston rod 922. Sheath or coating 1002 includes an expandable bellows 1004 formed therein allowing piston rod 922 to be reciprocated during operation of the pumping cartridge and providing an effective bioseal preventing contamination of the pump chamber of the pumping cartridge. Sheath or coating 1002 also includes a hollow, circumferential bulge 1006 therein axially positioned along tube 502 so that its hollow interior is in fluid communication with inlet bore 953 (see FIG. 12A) of the elongated tube 502 forming the pumping cartridge. Hollow bulge 1006 includes and is in fluid communication with an inlet line connector 1008 configured to be connected and in fluid communication with inlet line 1010.

Sheath or coating 1002 can be formed from a wide variety of resilient materials and is preferably formed of an elastomeric material, for example an elastomeric polymeric material such as a natural or synthetic rubber. The sheath or coating can be formed via coating of tube 502 or by shrink wrapping the sheath onto elongated tube 502 and piston rod 922. Alternatively, a sheath may be preformed, for example by injection molding, and subsequently installed on the elongated tube and piston rod as illustrated. Fluid-tight sealing of coating/sheath 1002 to the outer surface of elongated tube 502 and piston road 922 can, in some embodiments, be improved by bonding the tube and/or piston rod contacting surfaces of sheath/coating 1002 to the tube and/or piston rod, or bonding selected portions of such surfaces, by a variety of well-known means, for example via various adhesives, solvent welding, ultrasonic welding, thermal bonding, etc.

Figure 14:
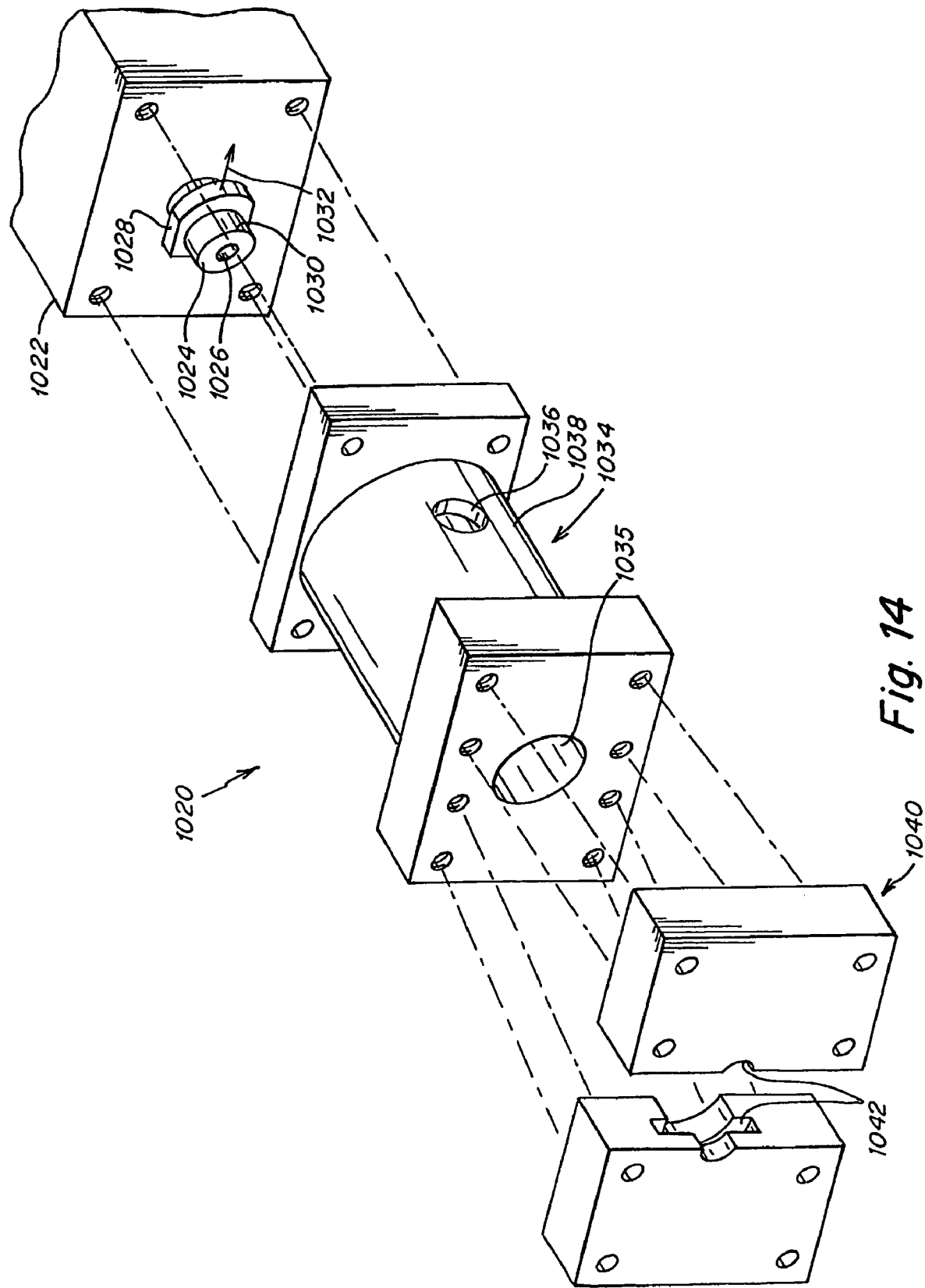
FIG. 14 is a schematic, exploded, perspective illustration of a support nest structure and a portion of a mechanical pump drive unit configured for coupling with an axially configured pumping cartridge.

FIG. 14 illustrates a disassembled view of a nesting structure 1020 and a portion of a mechanical pump drive unit 1022, to which it can be attached, which can be used, as illustrated or with slight modifications, with several of the previously-illustrated, axially configured pumping cartridges (e.g. pumping cartridges 900 and 1000). Mechanical pump drive unit 1022 includes a reciprocating pump plunger 1024 having a centrally disposed bore 1026 therein for receiving mechanical pump drive coupling region 126 of a piston rod. Attached to reciprocating plunger 1024 is a slidable engaging clamp 1028 configured to matingly engage coupling notch 144 of mechanical pump drive coupling region 126. Reciprocating plunger 1024 includes a slotted grove through a side wall thereof (not shown) positioned under coupling clamp 1028. Coupling clamp 1028 includes a notch engaging tab (not shown) extending from an inner surface thereof into the above-mentioned slot, which is configured to engage in coupling notch 144 of the piston rod when clamp 128 is positioned in contact with outer surface 1030 of plunger 1024. In preferred embodiments, clamp 1028 includes a spring or other biasing element tending to force its inner surface against surface 1030, thereby maintaining engagement of the tab in coupling notch 144, when the piston rod is installed in bore 1026. Upon disengagement, an operator can slide clamp 1028 in the direction shown by arrow 1032 displacing the tab sufficiently from bore 1026 to permit removal of the piston rod from the bore. In preferred embodiments, the coupling tab provided by clamp 1028 is be configured with a wedge shape allowing the tapered distal end of the piston rod (e.g. see FIG. 1 to automatically displace the tab upon insertion of the piston rod into bore 1026, permitting easy, automatic coupling during assembly of the pumping cartridge in operative configuration with mechanical pump drive unit 1022 and nesting structure 1020.

The body engaging component 1034 of nesting structure 1020 is connected to mechanical pump drive unit 1022, by for example, bolt fasteners (not shown). Body engaging component 1034 includes a bore 1035 for surrounding the elongated tube comprising the main body portion of the axially configured pumping cartridge, upon coupling, and a bore 1036 through a side wall 1038 of component 1034 to permit ingress of an inlet line, for example, inlet line 915 of pumping cartridge 900 or inlet line 1010 of pumping cartridge 1000. The pumping cartridge, upon coupling, is supported and immobilized within bore 1035 of the nesting structure, and axial movement of the pumping cartridge with respect to the mechanical pump drive unit is prevented via an outlet connector engaging portion 1040 of nesting structure 1020, which includes machined depressions 1042 therein having a shape and dimensions matingly complimentary to the shape and dimensions of shoulder regions 909 of outlet connectors 908 (see FIGS. 12A and 13). Outlet connector engaging component 1040 can be secured to body engaging component 1034 via connectors, for example bolt fasteners (not shown), thereby establishing the operative configuration.

Figure 15A:
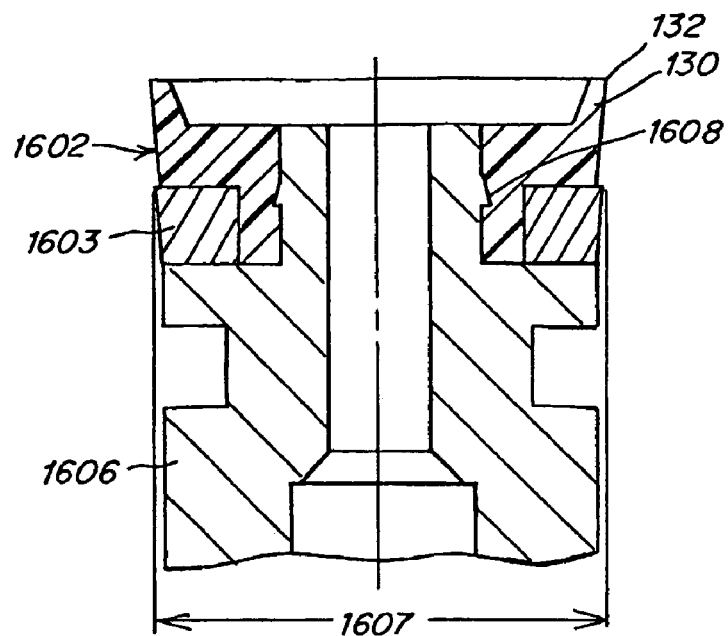
FIG. 15A is a schematic, cross-sectional illustration of another embodiment of a piston.

FIG. 15A illustrates an alternative configuration of a piston and piston rod assembly that includes a rigid support ring (e.g., made of metal or other strong, essentially rigid material). This configuration may be advantageously used in many of the non-floating sealing piston arrangements disclosed herein, such as that of FIGS. 3, 4A, 4B, 4C, 9A, 11A, 11B, 11C, and 11D, for extending the useful life of the piston. In the illustrated cross section, polymeric piston 1602, having a sealing component 130, is supported by a supporting ring 1603, having a tapered outer profile with its maximum projection at 1607. The piston 1602 and supporting ring 1603 are held onto the piston rod 1606 by barbs 1608, or by other retaining elements.

During operation, sealing component 130 bears on the cylinder wall, providing a seal. As described above, the sealing flange portion 132 of the sealing component may gradually erode during use. Without use of supporting ring 1603, after prolonged use, sealing component 130 may, under certain operating conditions, begin to erode preferentially at a particular spot and tilt piston 1602. The resulting forces could slightly deform piston 1602, permitting leakage past the piston or between the piston and the body.

Inclusion of supporting ring 1603 can prevent or postpone such preferential erosion and/or tilting of piston 1602. The maximum diameter of the ring, at 1607, is selected to have a small clearance from the wall of the cylinder. A nominal clearance of about 0.001 inch is typical. Under some operating conditions, the supporting ring may contact the wall. In such cases, the provision of a taper allows the ring to rapidly wear into conformance with the bore, while reducing the area of contact. Subsequently, in such embodiments, since supporting ring 1603 typically tends to erode more slowly than piston sealing component 130, supporting ring 1603 will tend to maintain the piston in a straight orientation to reduce preferential edge erosion and tilting of piston 1602. In tests, it has been found that supporting ring 1603 can, in certain situations substantially extend the life of the piston, for example, under some conditions the piston can be extended by a factor of at least about three, five, or even ten, for example, useful life may be extended from ten minutes to over an hour in some cases.

Figure 15B:
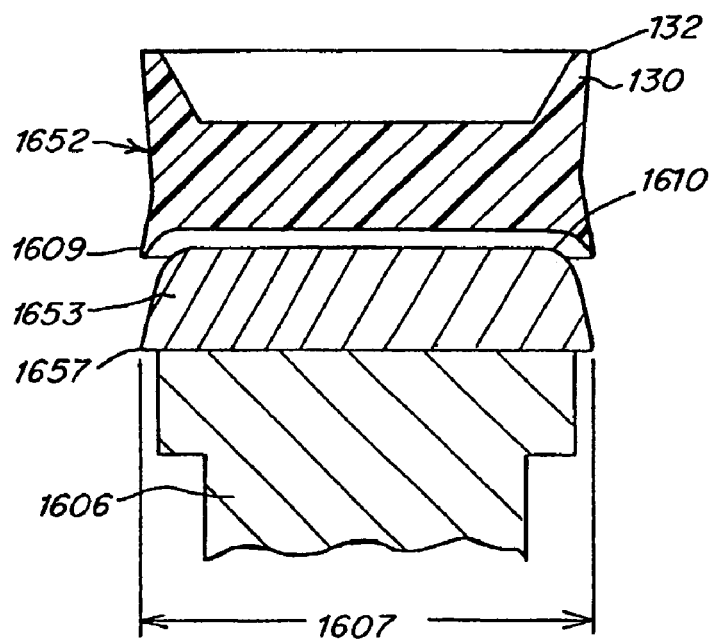
FIG. 15B is a schematic illustration of yet another embodiment of a piston.

An alternative embodiment for configuring the piston/support ring for providing beneficial ability to exclude external contaminants from the cylinder is illustrated in FIG. 15B. In this embodiment, a proximal flange 1609 is attached to piston 1652, or formed as a part of piston 1652. Supporting ring 1653 is contoured at 1610 so as to accommodate proximal flange 1609 and the maximum projection of supporting ring 1653, (i.e., maximum diameter 1657), is on the edge 1657 of supporting ring 1653. For clarity, piston 1652 and supporting ring 1653 are shown as separated in FIG. 15B, but the two components are attached or integrally formed. Proximal flange 1609 does not necessarily provide a seal, but it can be sized and configured to wipe the surface of the piston cylinder (not illustrated) on the back stroke, thereby confining contaminants to a zone that is proximal of the sealing flange 132. In other embodiments, instead of being positioned on the piston, the proximal flange can be positioned on the cylinder to help prevent contaminants from reaching the sealing component 130 or sealing flange 132.

Figure 16:
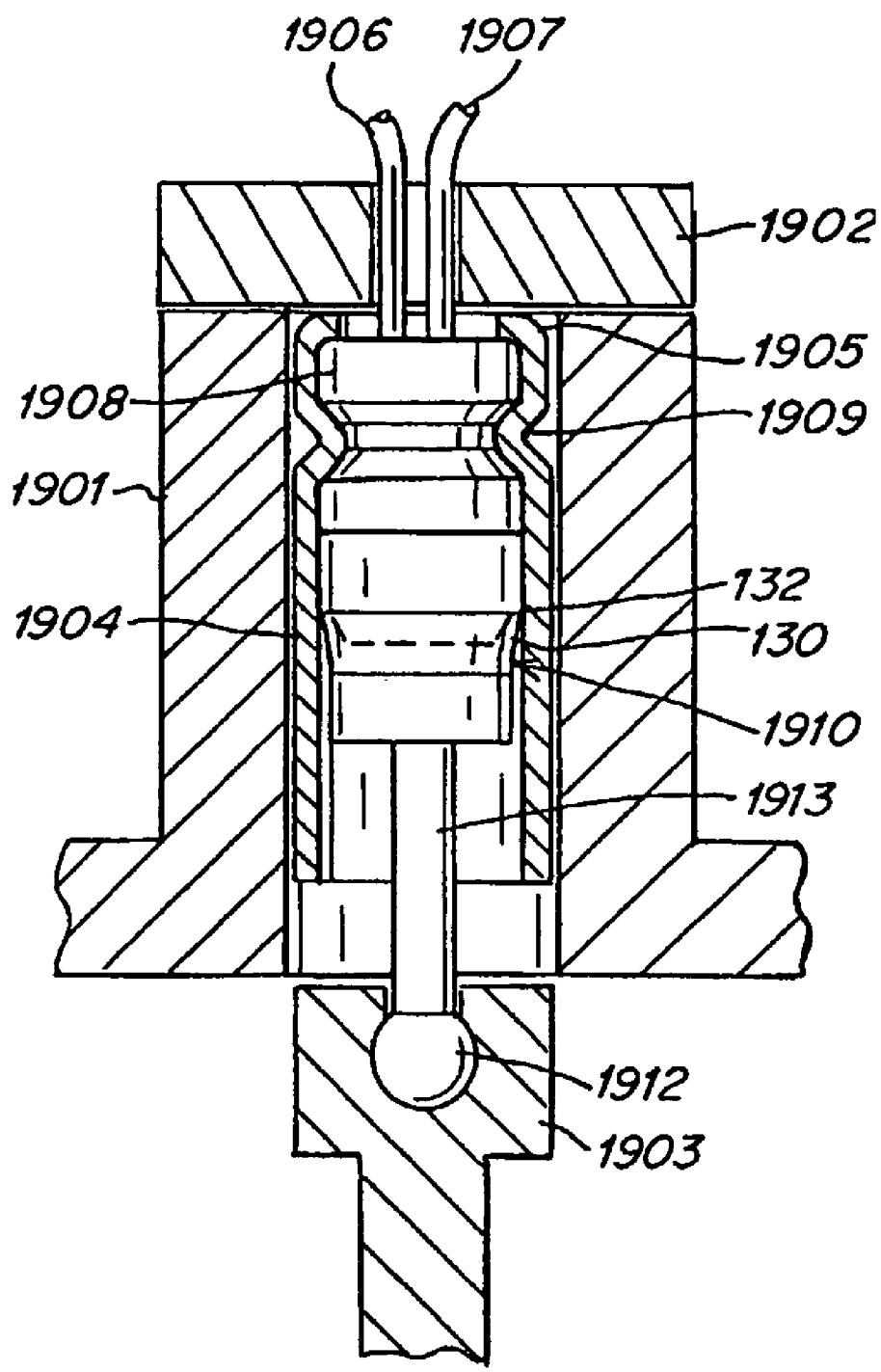
FIG. 16 is a schematic, cross-sectional illustration of a pumping cartridge partially formed of a thin-walled tube.

Another embodiment of an axial configuration pumping cartridge, assembled by crimping a tube, is illustrated in FIG. 16. In this configuration, the barrel of the cylinder is made of a thin-walled tubular cartridge which is not necessarily strong enough to withstand the pressure generated by the piston. To support the thin-walled tubular cartridge, the nesting mechanism of the pump drive unit has a robust cylinder 1901 that surrounds the cartridge 1904. The configuration may reduce the cost of the disposable portion. The pump drive unit as schematically illustrated includes: a robust cylinder 1901; a retaining block 1902 for a valve assembly 1908; and a drive element 1903 that attaches to an end 1912 of the piston rod 1913. A thin-walled tubular cartridge 1904 is positioned inside the cylinder 1901, and the piston assembly 1910 reciprocates within the cartridge 1904. The piston may be any of those described previously, but in this illustration a one-piece piston/piston rod assembly is shown having a main body portion 1910, a sealing component 130, and end 1912 of a rod portion 1913 for attachment to a drive element 1903. The piston/piston rod assembly may be injection molded, machined, or otherwise fabricated as a single piece. In other embodiments as previously described and illustrated, the piston may be fabricated as multiple pieces attached together. A valve block 1908, which contains inlet and outlet lines 1906, 1907 and inlet and outlet valves (not illustrated) similar to those previously described, can be retained in cylinder 1901 by retaining block 1902 or alternatively held by a crimp at 1909, and/or a distal crimp 1905. Retaining block 1902 may be secured to cylinder 1901 with a clamping device (not illustrated). Optionally, cylinder 1901 could be a disposable element instead of part of the drive mechanism.

Figure 17A:
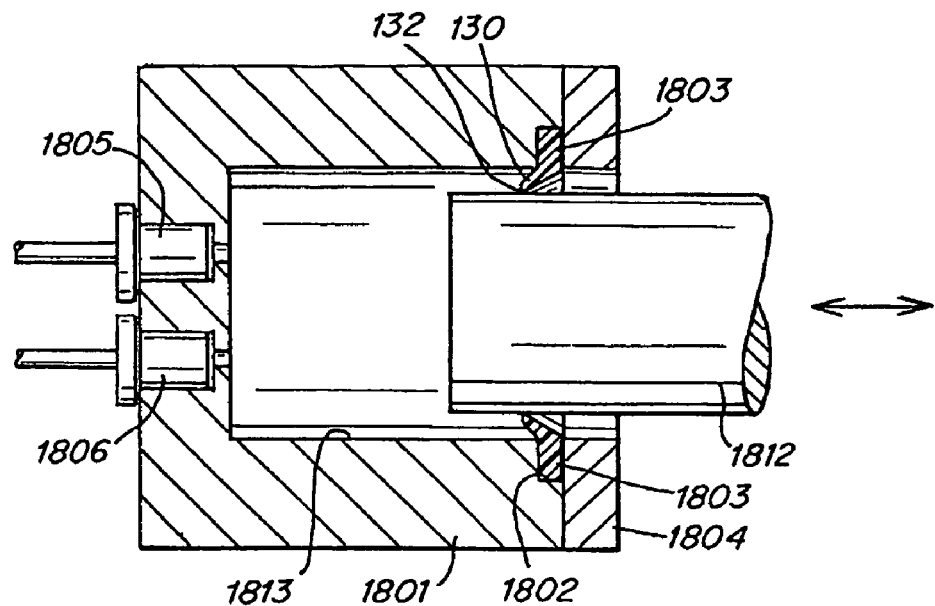
FIG. 17A is a schematic, cross-sectional illustration of a pumping cartridge with a sealing flange attached to a cylinder.

FIG. 17A illustrates an embodiment of a pumping cartridge provided by the invention with a piston rod not including a piston where a sealing component providing a seal between the piston rod and cylinder is carried by, included within, or part of the cylinder. In the embodiment illustrated, a cylinder 1801 has an annular recess 1802 within its inner surface 1813. A circumferential flared sealing ring 1803 providing a sealing component 130, which includes a flared sealing flange portion 132, is disposed within the annular recess 1802. A retaining element 1804 may be used to secure the sealing ring 1803 to the cylinder 1801. In preferred embodiments, the flared sealing flange portion 132 is dimensioned and configured such that during at least a part of the operation of the pumping cartridge, a seal formed between flared sealing flange 132 of cylinder 1801 and a surface of piston rod 1812 is able to withstand a pressure differential across the seal of at least about 1,000 psi without substantial leakage of fluid therethrough, more preferably at least about 8,000 psi, even more preferably at least about 15,000 psi, in other embodiments at least about 20,000 psi, in other embodiments at least about 30,000 psi, and in yet other embodiments at least about 50,000 psi. As discussed above in the context of the embodiment illustrated in FIG. 1, sealing component 130 and cylinder engaging main body portion 1804 of sealing ring 1803, can be integrally or non-integrally formed. Sealing ring 1803 can comprise a separate or separable element connected to cylinder 1801, either, rigidly (e.g., by gluing, welding, bonding, etc.), or non-rigidly and/or movably. In other embodiments, the cylinder could comprise an integrally formed one-piece sealing component. In such an embodiment, the cylinder, or at least a portion thereof, and the sealing component would comprise a single integral element.

FIG. 17A illustrates an embodiment of a pumping cartridge that includes a piston rod that constructed and arranged to reciprocate relative to a cylinder. Piston rod 1812 is couplable to a mechanical pump drive unit (illustrated in FIGS. 6A-6B). In such an embodiment, cylinder 1801 is held essentially stationary while piston rod 1812 reciprocates. In the present embodiment, valves 1805 and 1806 are positioned on the body of the cylinder.

Figure 17B:
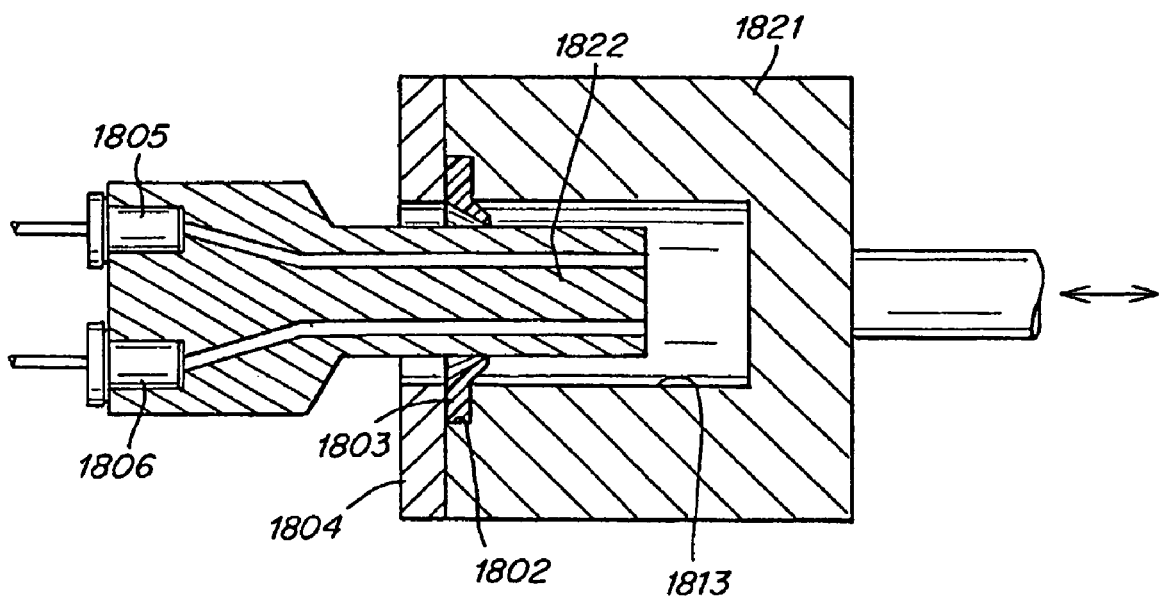
FIG. 17B is a schematic, cross-sectional illustration of another embodiment of a pumping cartridge with a sealing component attached to a cylinder.

In an alternative embodiment of a cartridge having a cylinder-associated sealing component, illustrated in FIG. 17B, the valves may be positioned on the piston rod instead of on the body of the cylinder as in FIG. 17A. In the present embodiment, the two valves 1805 and 1806 are positioned on piston rod 1822 and flared sealing ring 1803 is included within cylinder 1821. In other embodiments (not shown), one valve can be positioned on the body of the cartridge while the other valve is positioned on the piston rod. Further, sealing ring 1803 could be eliminated and replaced with a sealing component carried by a piston connected to the piston rod as previously described. In the embodiment illustrated in FIG. 17B, cylinder 1821 is constructed and arranged to reciprocate around an essentially stationary piston 1822. Of course, embodiments which include a piston rod and a cylinder that both move are also contemplated.

Figure 17C:
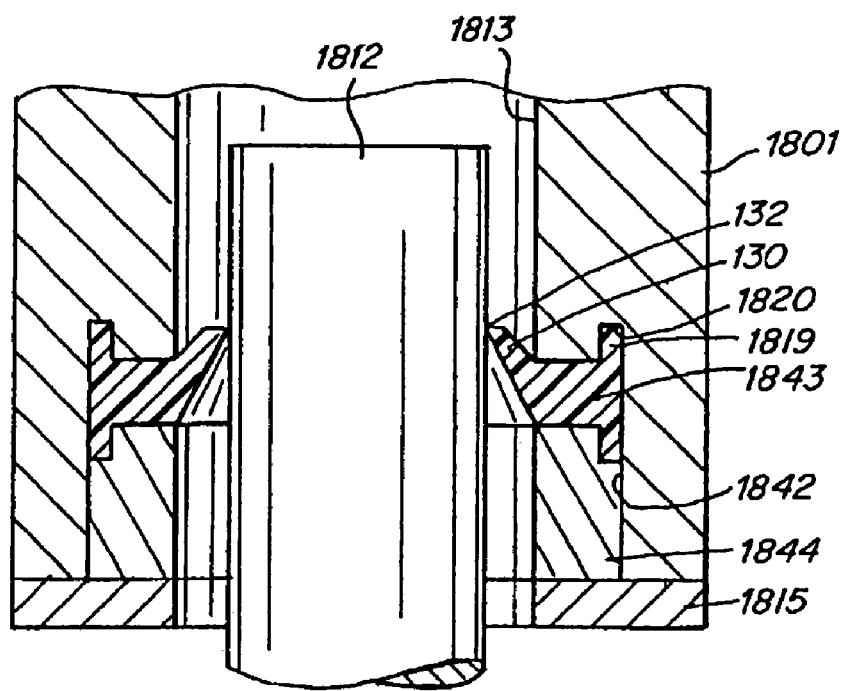
FIG. 17C is a schematic, cross-sectional illustration of a piston and cylinder wall including a sealing component.

FIG. 17C illustrates in more detail one embodiment (similar to that shown previously in FIG. 17A) of a cylinder including a sealing ring 1843 in more detail. Cartridge 1801 includes a cylinder 1813 with an annular recess 1842 within its surface. Annular recess 1842 includes undercuts 1820 to retain sealing ring extensions 1819 and thereby retain sealing ring 1843. As described above, flared sealing ring 1843 may be connected to cylinder 1813 by other methods. Retaining element 1844 and optional additional retaining element 1815 can be used to secure sealing ring 1843 to cylinder 1813. In this particular embodiment, the portion of sealing ring 1843 retained within cylinder 1801 acts as a sealing component support element for sealing component 130.

Figure 17D:
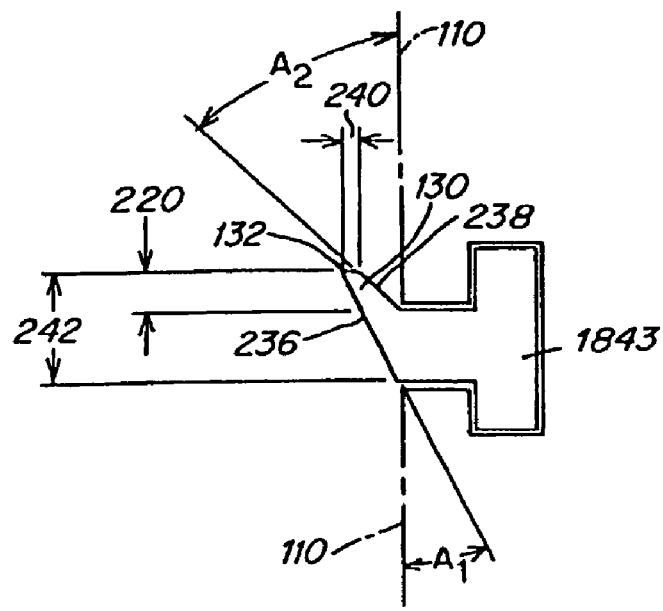
FIG. 17D is a schematic, cross-sectional illustration of a cylinder wall including a sealing component.

FIG. 17D shows one embodiment of flared sealing ring 1843 including sealing component 130 in more detail. Dimensions and angles which have values preferably falling within the ranges previously described for piston-associated sealing components are called out by the same notation (e.g., angles $A_1$ and $A_2$, and dimensions 220, 240 and 242). In preferred embodiments, the flared sealing flange 132 is configured such that the first surface 236 of the flared sealing flange portion adjacent to and facing a surface with which it is in sliding contact (e.g., a piston rod surface) forms a first angle $A_1$ with respect to the longitudinal axis 110 of the cylinder and a second surface 238, facing away from the surface with which it is in sliding contact, forms a second angle $A_2$ with respect to the longitudinal axis of the cylinder.

While several embodiments of pumping cartridges, components thereof, pumping systems, and methods for medical and surgical pumping/infusion have been illustrated herein, those of ordinary skill in the art will readily envision a variety of other means and structures for providing pumping cartridges, components thereof, pumping systems, and pumping methods to perform the functions and/or obtain the results or advantages described herein, and each of such variations or modifications is deemed to be within the scope of the present invention.

More generally, those skilled in the art would readily appreciate that all parameters, dimensions, materials, and configurations described herein are meant to be exemplary and that actual parameters, dimensions, materials, and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, or method described herein. In addition, any combination of two or more such features, systems, or methods, provided that such features, systems, or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively, as set forth in MPEP section 2111.03.

What is claimed is:

1. A pumping cartridge comprising:
a cylinder; and a piston rod constructed and arranged for reciprocating motion with respect to the cylinder, the pumping cartridge including therein a sealing component shaped to include a circumferential, flared sealing flange portion extending away from a portion to which it is attached, of a sealing component support element, such that a first surface of the flared sealing flange portion adjacent to and facing a surface with which it is in sliding contact forms a first angle with respect to the longitudinal axis of the cylinder and a second surface of the flared sealing flange portion facing away from the surface with which it is in sliding contact forms a second angle with respect to the longitudinal axis of the cylinder, where the first angle exceeds 0 degrees, the second angle does not exceed 90 degrees, the second angle exceeds the first angle, and the sealing flange portion of the sealing component is constructed of a non-elastomeric material, the flared sealing portion is essentially irreversibly deformed during sliding motion of the piston rod relative to the cylinder.

2. The pumping cartridge as in claim 1, further comprising a piston coupled to the piston rod, wherein the piston includes the sealing component shaped to include the circumferential, flared sealing flange portion, the flared sealing flange portion extending away from a portion, to which it is attached, of a main body of the piston, such that the first surface of the flared sealing flange portion is adjacent to and faces an inner surface of the cylinder to form the first angle with respect to the longitudinal axis of the cylinder and the second surface of the flared sealing flange portion faces the cylinder bore to form the second angle with respect to the longitudinal axis of the cylinder.

3. The pumping cartridge as in claim 1, wherein the cylinder includes the sealing component shaped to include the circumferential, flared sealing flange portion, the flared sealing flange portion extending away from a portion, to which it is attached, of a cylinder-engaging main body portion of a sealing ring coupled to the cylinder, such that the first surface of the flared sealing flange portion is adjacent to and faces the piston to form the first angle with respect to the longitudinal axis of the cylinder and the second surface of the flared sealing flange portion faces an inner surface of the cylinder to form the second angle with respect to the longitudinal axis of the cylinder.

4. The pumping cartridge as in claim 1, wherein the cylinder includes the sealing component shaped to include the circumferential, flared sealing flange portion, the flared sealing flange portion extending away from a portion, to which it is attached, of an inner surface of the cylinder, such that the first surface of the flared sealing flange portion is adjacent to and faces the piston to form the first angle with respect to the longitudinal axis of the cylinder and the second surface of the flared sealing flange portion faces an inner surface of the cylinder to form the second angle with respect to the longitudinal axis of the cylinder.

5. The pumping cartridge as in claim 2, wherein the piston includes at least part of a valve.

6. The pumping cartridge as in claim 5, wherein the valve included in the piston is constructed and positioned to act as an inlet valve to the cylinder of the fluid being pumped by the pumping cartridge when it is in operation.

7. The pumping cartridge as in claim 1, wherein a proximal end of the cylinder has a beveled inner surface.

8. The pumping cartridge as in claim 2, wherein the sealing component is integrally formed with the main body of the piston and both the main body of the piston and the sealing component are formed of the same polymeric material.

9. The pumping cartridge as in claim 8, wherein the sealing component and the main body of the piston are injection molded as one piece.

10. The pumping cartridge as in claim 1, wherein the flared sealing flange portion has a predefined length and extends both axially and radially away from the portion of the sealing component support element to which it is attached so as to form a cantilevered circumferential flange thereon.

11. The pumping cartridge as in claim 10, wherein the sealing flange portion extends axially away from the portion of the sealing component support element to which it is attached by a distance of between about 0.01 inch and about 0.2 inch.

12. The pumping cartridge as in claim 2, wherein the maximum axial thickness of the piston is between about 0.04 inch and about 0.32 inch.

13. The pumping cartridge as in claim 2, wherein the pumping cartridge is constructed and arranged so that the piston reciprocates within an essentially immobile cylinder.

14. The pumping cartridge as claimed in claim 13, wherein the flared sealing flange portion of the piston has a predefined length and extends both axially and radially away from the portion of the main body of the piston to which it is attached so as to form a cantilevered circumferential flange thereof, and wherein the sealing flange portion of the piston has a maximum outer diameter large enough to enable at least a portion of the sealing flange to be in essentially continuous contact with an inner surface of the cylinder during reciprocation of the piston.

15. The pumping cartridge as in claim 14, wherein the sealing flange portion of the piston has a maximum-outer diameter, when in a relaxed configuration prior to insertion into the cylinder upon assembly of the pumping cartridge, exceeding a maximum outer diameter of the main body of the piston.

16. The pumping cartridge as in claim 15, wherein the sealing flange portion of the piston has a maximum outer diameter, when in a relaxed configuration prior to insertion into the cylinder upon assembly of the pumping cartridge, exceeding a maximum outer diameter of the main body of the piston by at least about 1%.

17. The pumping cartridge as in claim 14, wherein a portion of the cylinder in which the piston reciprocates has an inner diameter exceeding the maximum outer diameter of the main body of the piston.

18. The pumping cartridge as in claim 17, wherein the portion of the cylinder in which the piston reciprocates has an inner diameter less than a maximum outer diameter of the sealing flange portion of the piston, by at least about 1% when it is in a relaxed configuration prior to insertion into the cylinder upon assembly of the pumping cartridge.

19. The pumping cartridge as in claim 14, wherein the piston is annular in shape with a centrally disposed bore therethrough defining a fluid flow path.

20. The pumping cartridge as in claim 1, where in the first angle is between about 1 degree and about 20 degrees.

21. The pumping cartridge as in claim 1, wherein the second angle is between about 10 degrees and about 80 degrees.

22. The pumping cartridge as in claim 20, wherein the second angle is between about 10 degrees and about 80 degrees.

23. The pumping cartridge as in claim 20, wherein the first angle is between 3 degrees and 12 degrees and the second angle is between 15 degrees and 30 degrees.

* * * * *